US011452772B2

(12) United States Patent
Vangelisti et al.

(10) Patent No.: US 11,452,772 B2
(45) Date of Patent: Sep. 27, 2022

(54) LIVE-ATTENUATED YELLOW FEVER VIRUS STRAIN ADAPTED TO GROW ON VERO CELLS AND VACCINE COMPOSITION COMPRISING THE SAME

(71) Applicant: Sanofi Pasteur, Lyons (FR)

(72) Inventors: Manuel Vangelisti, Lyons (FR); Nathalie Mantel, Lyons (FR); Yves Girerd-Chambaz, Messimy (FR); Fabienne Piras, Fleurieux sur l'Arbresle (FR)

(73) Assignee: Sanofi Pasteur, Lyons (FR)

( * ) Notice: Subject to any disclaimer, the term of this patent is extended or adjusted under 35 U.S.C. 154(b) by 0 days.

(21) Appl. No.: 17/453,758

(22) Filed: Nov. 5, 2021

(65) Prior Publication Data

US 2022/0047692 A1    Feb. 17, 2022

Related U.S. Application Data

(63) Continuation of application No. 17/045,322, filed as application No. PCT/EP2019/058268 on Apr. 2, 2019.

(30) Foreign Application Priority Data

Apr. 6, 2018    (EP) .................................... 18305405

(51) Int. Cl.
| A61K 39/12 | (2006.01) |
| C12N 7/04 | (2006.01) |
| A61K 39/00 | (2006.01) |

(52) U.S. Cl.
CPC ................ *A61K 39/12* (2013.01); *C12N 7/04* (2013.01); *A61K 2039/5254* (2013.01); *C12N 2770/24134* (2013.01)

(58) Field of Classification Search
None
See application file for complete search history.

(56) References Cited

U.S. PATENT DOCUMENTS

2011/0287519 A1* 11/2011 Lee .......................... C12N 7/00
                                                                    435/235.1
2021/0154289 A1    5/2021 Vangelisti et al.

FOREIGN PATENT DOCUMENTS

| WO | WO 2009/109550 | 9/2009 |
| WO | WO 2012/011969 | 1/2012 |
| WO | WO 2014/016360 | 1/2014 |

OTHER PUBLICATIONS

Moulin et al. (Biologicals. 2013; 41: 238-246).*
Beasley et al. (Virus Research. 2013; 176: 280-284).*
Galler et al. (Vaccine. 1998; 16 (9/10): 1024-1028).*
Xie et al. (Virus Research. 1998; 55: 93-99).*
Roukens et al. (Expert Opinion on Biological Therapy. 2008; 8 (11): 1787-1795).*
Palmer et al. (Journal of General Virology. 2007; 88: 148-156).*

(Continued)

*Primary Examiner* — Shanon A. Foley
(74) *Attorney, Agent, or Firm* — Fish & Richardson P.C.

(57) ABSTRACT

The invention relates to a live-attenuated yellow fever virus strain adapted to grow on Vero cells from a parent yellow fever virus 17D substrain that is not adapted to grow on Vero (Continued)

Figure 4:
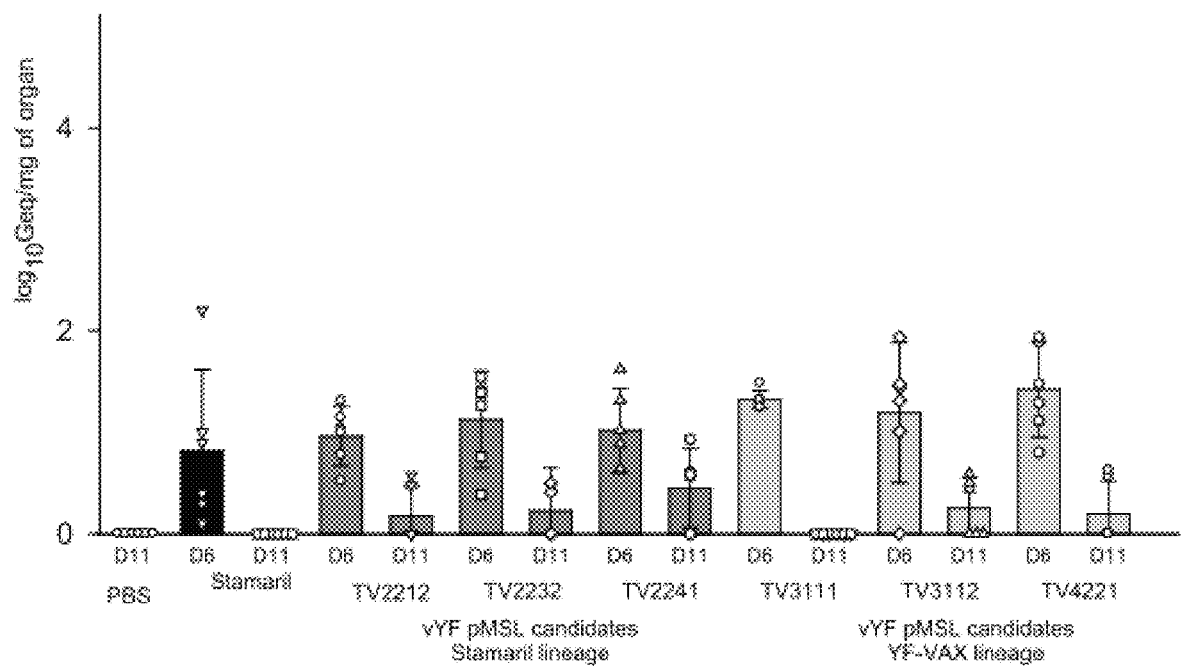

cells, wherein said live-attenuated yellow fever virus strain is less neurovirulent than said parent yellow fever virus 17D substrain.

15 Claims, 11 Drawing Sheets

Specification includes a Sequence Listing.

(56) References Cited

OTHER PUBLICATIONS

Hansen and Barrett. (Pharmaceuticals. 2021; 14; 891).*
Office Action in U.S. Appl. No. 17/045,322, dated Dec. 9, 2021, 16 pages.
Piras-Douce et al., "Next generation live-attenuated yellow fever vaccine candidate: Safety and immuno-efficacy in small animal models," Vaccine, 2021, 39:1846-1856.
Barrett, "Yellow fever live attenuated vaccine: A very successful live attenuated vaccine but still we have problems controlling the disease", Vaccine, 2017; 35(44): 5951-5955.
Beasley et al., "Adaptation of yellow fever virus 17D to Vero cells in associated with mutations in structural and non-structural protein genes", Virus Research, 2013, 176(1-2): 280-284.
Blaney et al., "Mutations which enhance the replication of dengue virus type 4 and an antigenic chimeric dengue virus type 2/4 vaccine candidate in Vero cells", Vaccine, 2003, 21(27-30): 4317-4327.
Dos Santos et al., "Complete nucleotide sequence of yellow fever virus vaccine strains 17DD and 17D-213", Virus Research, 1995, 35(1):35-41.
Dupuy et al., "Nucleotide sequence comparison of the genome of two 17D-204 yellow fever vaccines", Nucleic Acids Research, 1989, 17(10): 3989.
Erickson et al., "Spectrum of disease outcomes in mice infected with YFV-17D", Journal of General Virology, 2015, 96:1328-1339.
Hayes, "Is it time for a new yellow fever vaccine?", Vaccine, 2010, 28(51):8073-8076.
Julander, "Animal models of yellow fever and their application in clinical research", Current Opinion in Virology, 2016, 18:64-69.
Kolell et al., "Virus Production in Vero Cells Using a Serum-free Medium", Cell Technology for Cell Products, 2007, 583-585.
Mantel et al., "Standardized quantitative RT-PCR assays for quantitation of yellow fever and chimeric yellow fever-dengue vaccines", journal of Virological Methods, 2008, 151(1)40-6.
Mason et al., "Yellow fever vaccine: direct challenge of monkeys given graded doses of 17D vaccine", Applied Microbiology, 1973, 25(4):539-44.
Meier et al., "A mouse model for studying viscerotropic disease caused by yellow fever virus infection", PLoS Pathogens, 2019, 11 pages.
Monath et al., "Inactivated yellow fever 17D vaccine: development and nonclinical safety, immunogenicity and protective activity", Vaccine, 2010, 28(22):3827-3840.
Monath, "Yellow fever vaccine", Expert Review Vaccines, 2005, 4(4)553-574.
Moulin et al., "Yellow fever vaccine: comparison of the neurovirulence of new 17D-204 Stamaril™ seed lots and RK 168-73 strain", Biologicals, 2013, 41(4):238-246.
Needleman et al., "A General Method Applicable to the Search for Similarities in the Amino Acid Sequence of Two Proteins", Journal of Molecular Biology, 1970, 48(3):443-453.
PCT International Preliminary Report on Patentability in International Application No. PCT/EP2019/058268, dated Oct. 6, 2020, 11 pages.
PCT International Search Report and Written Opinion in International Application No. PCT/EP2019/058268, dated Jun. 24, 2019, 14 pages.
Pereira et al., "An inactivated yellow fever 17DD vaccine cultivated in Vero cell cultures", Vaccine, 2015, 33(35):4261-4268.
Rice et al., "Nucleotide Sequence of Yellow Fever Virus: Implications for Flavivirus Gene Expression and Evolution", Science, 1985, 229(4715):726-733.
Tang et al., "Molecular basis for adaptation of a chimeric dengue type-4/Japanese encephalitis virus to Vero cells", Microbiol. Immunol., 2005, 49(3): 285-294.
Tretyakova et al., "Plasmid DNA initiates replication of yellow fever vaccine in vitro and elicits virus-specific immune response in mice", Virology, 2014, 468: 28-35.
World Health Organization, "Recommendations to assure the quality, safety and efficacy of live attenuated yellow fever vaccines", WHO Technical report series, 2010, No. 978, Annex 5, 241-314.
World Health Organization, "Requirements for yellow fever vaccine", WHO Technical report series, 1998, No. 872, Annex 2, 30-68.

* cited by examiner

Stamaril® WSL

YF-VAX® Infectious clone
↓
*in vitro* transcription ➔ RNA or

RNA Purification
including phenol extraction steps: elimination of adventitious agents

↓

Transfection in SF Vero ➔ virus recovery = P1

↓

2 amplifications on SF-Vero:
= P2 & P3

↓

Viral cloning by 2 plaque purification cycles = P4 & P5
➔ 16 clones for each lineage

↓

2 Amplifications on SF-Vero = P6 & P7

↓

Selection of 3 strains for each lineage

↓

Amplification on SF-Vero = P8

↓

Selection of vYF-250 pMSL

LIVE-ATTENUATED YELLOW FEVER VIRUS STRAIN ADAPTED TO GROW ON VERO CELLS AND VACCINE COMPOSITION COMPRISING THE SAME

CROSS REFERENCE TO RELATED APPLICATIONS

The present application is a continuation of patent application Ser. No. 17/045,322, filed on Oct. 5, 2020, which is the national stage entry of International Patent Application No. PCT/EP2019/058268, filed on Apr. 2, 2019, and claims priority to Application No. EP 18305405.5, filed on Apr. 6, 2018, the disclosures of which are incorporated herein by reference.

SEQUENCE LISTING

This application contains a Sequence Listing that has been submitted electronically as an ASCII text file named "Sequence_Listing.txt." The ASCII text file, created on Oct. 29, 2021, is 123 KB in size. The material in the ASCII text file is hereby incorporated by reference in its entirety.

FIELD OF THE INVENTION

The present invention relates to a live-attenuated yellow fever virus (YFV) strain and uses thereof for the preparation of a vaccine composition against an infection by a YFV.

In particular, the live-attenuated YFV strain is adapted to grow on Vero cells, and has been obtained from a parent live-attenuated YFV strain that is not adapted to grow on Vero cells, but rather that is adapted to grow on embryonated eggs. The live-attenuated YFV strain is further characterized by a reduced neurovirulence, as compared to the parent live-attenuated YFV strain.

BACKGROUND OF THE INVENTION

The yellow fever is a virus-mediated and lethal disease that is spread over 50 countries in the tropical areas of Africa, Central and South America.

The yellow fever is an acute viral haemorrhagic disease, some patients being affected by a jaundice, which explains the use of the term "yellow". The featured symptoms of yellow fever may include fever, headache, jaundice, muscle pain, nausea, vomiting and fatigue. Moreover, a small proportion of patients who contract the virus develop severe symptoms and approximately half of those die within 7 to 10 days.

The yellow fever virus (YFV) belongs to the family of Flaviviruses, among which Dengue virus (DV), Japanese encephalitis virus (JEV), tick-borne encephalitis virus (TBEV), West Nile virus (WNV) and Zika virus (ZV) are other members. The YFV consists of a lipoprotein envelope surrounding a nucleocapsid composed of the capsid protein and a single-stranded, positive-sense RNA, which has a length of 10862 nucleotides. In between a 5' untranslated (5' UTR) and a 3' untranslated regions (3' UTR), the RNA encodes, from the 5' end to the 3' end, three structural proteins, namely a capsid protein (C protein), a premembrane/membrane protein (prM/M protein), an envelope protein (E protein) and eight non-structural (NS) proteins, namely NS1, NS2A, NS2B, NS3, NS4A, P2k peptide, NS4B and NS5 proteins.

Wild-type YFV is principally vectored by *Aedes* spp. mosquitoes in Africa and Haemogogus and Sabethes spp. in South America, and there are non-human primate hosts which differ by geographic region. The YFV transmission is mainly achieved according to two epidemiological patterns, (1) the urban pattern and (2) the forest pattern (also known as the jungle or sylvan cycle). Despite the two patterns of transmission, only one clinically relevant disease has been identified, which accounts for the same virus being involved. In the American continent, the YFV circulates today by means of an endemic, forest pattern that results in up to several hundred reports of infection in non-immune forest workers per year. In parallel, the virus circulates in Africa by means of both urban and forest patterns and periodically breaks out of its endemic pattern to infect large numbers of non-immune persons in the course of major epidemics.

Currently, there are no antivirals for yellow fever disease, and vaccination is critical in preventing the disease. In this regard, as early as in the 1930's, two kinds of live-attenuated YFV vaccines were developed.

The first one corresponds to the French neurotropic vaccine (FNV), that was prepared from the wild-type French viscerotropic virus (FVV, isolated from Françoise Mayali in Senegal in 1928) and was passaged in mouse brain. However, the FNV proved rapidly to be too neurovirulent, having an exacerbated incidence of post-vaccinal encephalitis in children, and was abandoned in the early 1980's (Barrett, 2017).

The second approach corresponds to the "17D" strain, that was prepared from the wild-type strain Asibi (isolated from a mild human case—"Mr. Asibi"—in Ghana in 1927) and was passaged in mouse and chicken tissues. The vaccine strain 17D has lost both viscerotropism and neurovirulence (Monath, 2005).

Currently, six countries are producing live-attenuated YFV vaccine compositions from substrains derived from the 17D strain, namely Brazil (17DD substrain), China (17D-204 substrain), France (17D-204 substrain Stamaril®), Russia (17D-213 substrain), Senegal (17D-204 substrain) and USA (17D-204 substrain YF-VAX®) (Barrett, 2017).

To date, all currently commercialized vaccines are produced in embryonated hen eggs, a production process that has been complicated by robustness issues in the past (Barrett, 2017). Particularly, there is often a shortage of YFV vaccines due to manufacturing issues. Indeed, during the 2016 epidemics in Angola and the Democratic Republic of Congo, a shortage of available vaccine lots resulted, for the first time, in the necessity of fractioning doses in order to adapt to the emergency context (Barrett; 2017). Further, YFV vaccine produced on embryonated hen eggs is contraindicated in people allergic to eggs.

An alternative to vaccine production on the basis of embryonated eggs is the use of suitable cell lines for passaging the virus, such as mammalian cell lines. Among the mammalian cell lines, the Vero cell line is one of the most studied, while providing stability and well-documented performance in quality and quantity of viral yield. The Vero cells have received FDA approval and are used throughout the world. For example, Vero cells have been used for the preparation of a vaccine against the Japanese encephalitis (commercialized under the brand IXIARO®), against Influenza virus, against poliovirus and against rabies.

Past and current strategies to take advantage of Vero cells to prepare YFV vaccines have emerged, and it is noteworthy to mention that these strategies are merely oriented towards the feasibility of preparing YFV vaccines on the basis of inactivated virus (Hayes, 2010; Beasley et al., 2013; Pereira et al., 2015). Nevertheless, while a yellow fever inactivated vaccine may theoretically seem safer, it is unlikely to fully match the long-term protection provided by a single dose of the current live-attenuated yellow fever vaccines (Hayes, 2010). Further, in the context of the recent yellow fever epidemics, live-attenuated vaccines seem better suited to provide high population coverage of long lasting protective immunity against yellow fever in endemic areas.

The specific constraints of a live-attenuated virus for use in a vaccine is to maintain its attenuation, i.e. for a yellow fever virus to be at least as attenuated in terms of neuro-virulence and viscerotropism as the current marketed live-attenuated yellow fever vaccines; while being immunogenic enough to protect patients from the corresponding disease. In this regard, achieving both characteristics, i.e. attenuation and immunogenicity, for a given yellow fever strain has not been easy as can be seen, for instance, in Monath, 2005.

Accordingly, due to the various drawbacks associated with producing live-attenuated YFV vaccines based on embryonated hen eggs, there remains a need for alternative production methods for providing live-attenuated YFV vaccines.

SUMMARY OF THE INVENTION

In one aspect, the invention relates to a live-attenuated yellow fever virus strain adapted to grow on Vero cells from a parent yellow fever virus 17D substrain that is not adapted to grow on Vero cells, wherein said live-attenuated yellow fever virus strain is less neurovirulent than said parent yellow fever virus 17D substrain.

In another aspect, the invention further relates to a live-attenuated yellow fever virus strain comprising a nucleic acid comprising:
  i) a mutation in the codon for the amino acid at position 480 of the envelope protein (E) which results in an amino acid change from valine to leucine, or
  ii) a mutation in the codon for the amino acid at position 65 of the non-structural protein 2A (NS2a) which results in an amino acid change from methionine to valine.

Another aspect of the invention relates to a live-attenuated yellow fever virus strain which comprises an envelope protein comprising a mutation at position 480 which results in an amino acid change from valine to leucine.

Another aspect of the invention relates to a live-attenuated yellow fever virus strain which comprises an envelope protein comprising a leucine residue at the position within the protein that corresponds to position 480 of SEQ ID NO. 15.

In another aspect, the invention further relates to a live-attenuated yellow fever virus strain comprising a nucleic acid molecule encoding:
  (i) an envelope protein comprising a mutation at position 480 which results in an amino acid change from valine to leucine, and
  (ii) a NS2a protein comprising a mutation at position 65 which results in an amino acid change from methionine to valine.

Another aspect of the invention relates to a live-attenuated yellow fever virus strain comprising a nucleic acid molecule encoding:
  (i) an envelope protein which comprises a leucine residue at the position within the protein that corresponds to position 480 of SEQ ID NO. 15, and
  (ii) an NS2a protein which comprises a valine residue at the position within the protein that corresponds to position 65 of SEQ ID NO. 16.

Another aspect of the invention also relates to an immunogenic composition comprising a live-attenuated yellow fever virus strain according to the present invention and a pharmaceutically acceptable vehicle.

In a still other aspect, the invention further relates to a method for obtaining a live-attenuated yellow fever virus strain adapted to grow on Vero cells, comprising the steps of:
  a) purifying the viral genomic RNA of a parent live-attenuated yellow fever virus strain that is not adapted to grow on Vero cells, and that is optionally adapted to grow on eggs;
  b) transfecting Vero cells with the viral genomic RNA purified in step a), whereby transfected Vero cells are obtained;
  c) growing the transfected Vero cells obtained in step b) in a culture medium, whereby a first yellow fever virus population is obtained and further recovered;
  d) amplifying the recovered first yellow fever virus population obtained at the end of step c) 2 times or more on fresh Vero cells, whereby a second yellow fever virus population is obtained;
  e) cloning the second yellow fever virus population obtained in step d) by two or more successive plaque purifications on Vero cells whereby a plurality of yellow fever virus clones is obtained;
  f) amplifying separately each of the recovered yellow fever virus clones obtained at the end of step e) 2 times or more on fresh Vero cells, whereby a plurality of yellow fever virus strains is obtained; and
  g) selecting from the said plurality of yellow fever virus strains recovered in step f) one or more live-attenuated yellow fever virus strain that is less neurovirulent than the parent live-attenuated yellow fever virus strain, in a mouse lethal dose 50 ($MLD_{50}$) test.

Another aspect of the invention also relates to a live-attenuated yellow fever virus strain obtainable by a method according to the present invention.

In another aspect, the invention also relates to a live-attenuated yellow fever virus strain according to the present invention for use in the preparation of a vaccine.

A further aspect of the invention relates to a vaccine comprising a live-attenuated yellow fever virus strain according to the present invention for use in preventing an infection by a yellow fever virus.

LEGENDS OF THE FIGURES

FIG. 1: Diagram illustrating the preparation of a live-attenuated yellow fever virus strain adapted to grow on Vero cells (vYF), at the pre Master Seed Lot (pMSL) stage.

Figures 2, 3:
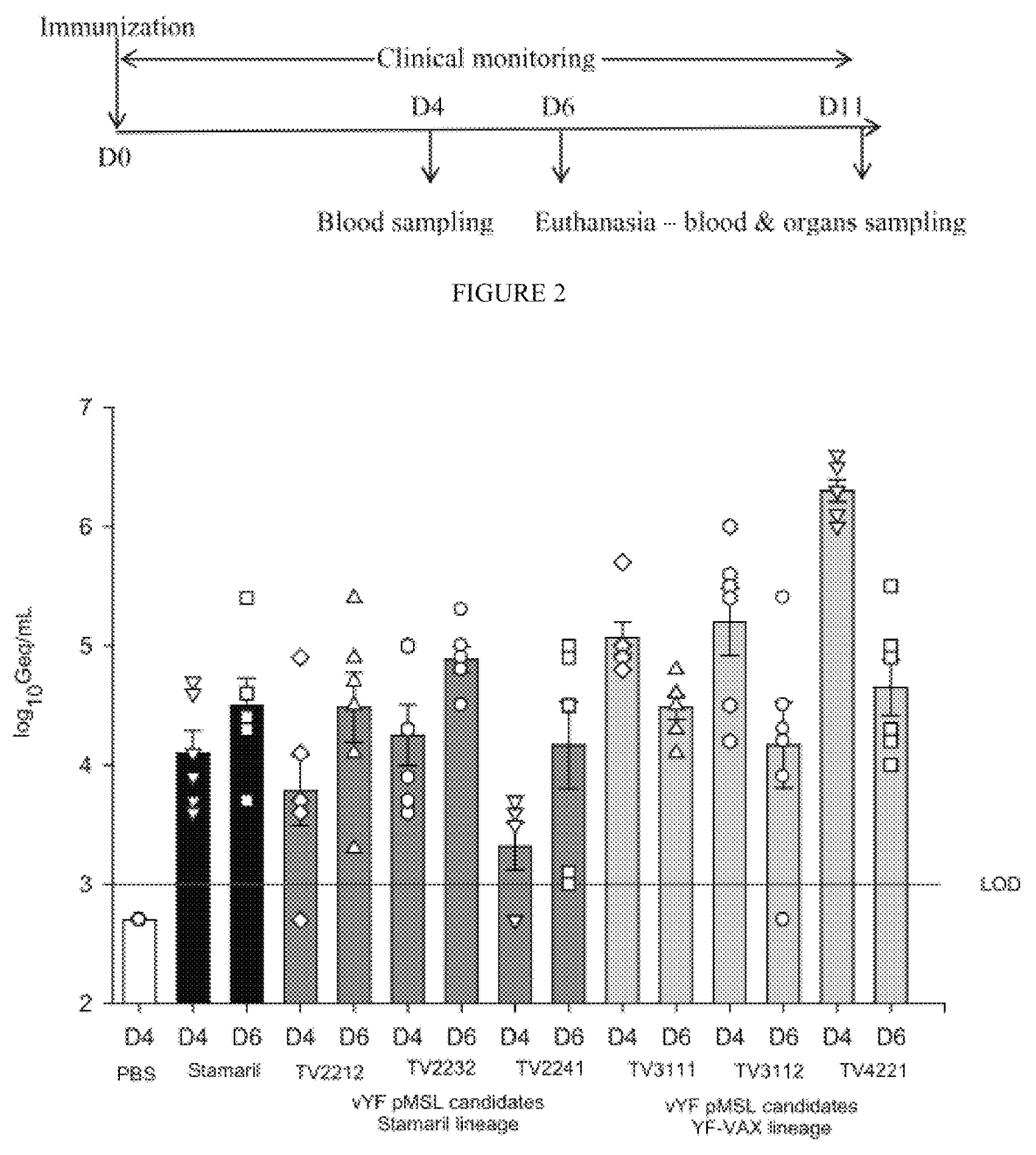

FIG. 2: Diagram illustrating the viscerotropism assay on an A129 mouse model.

FIG. 3: Plots illustrating the viremia measured by YF-NS5 qRT-PCR in sera collected at D4 and D6 from A129 mice immunized at D0 with PBS (white bar); Stamaril® reference (black bars) or with vYF pMSL candidates deriving from the Stamaril® lineage (TV2212, TV2232 and TV2241; dark grey bars) or from the YF-VAX® lineage (TV3111, TV3112 and TV4221; light grey bars).

FIG. 4: Plots illustrating the viral load measured by YF-NS5 qRT-PCR in liver samples collected at D6 and D11 from A129 mice immunized at D0 with PBS (white bar); Stamaril® reference (black bars) or with vYF pMSL candidates deriving from the Stamaril® lineage (TV2212, TV2232 and TV2241; dark grey bars) or from the YF-VAX® lineage (TV3111, TV3112 and TV4221; light grey bars).

Figure 5:
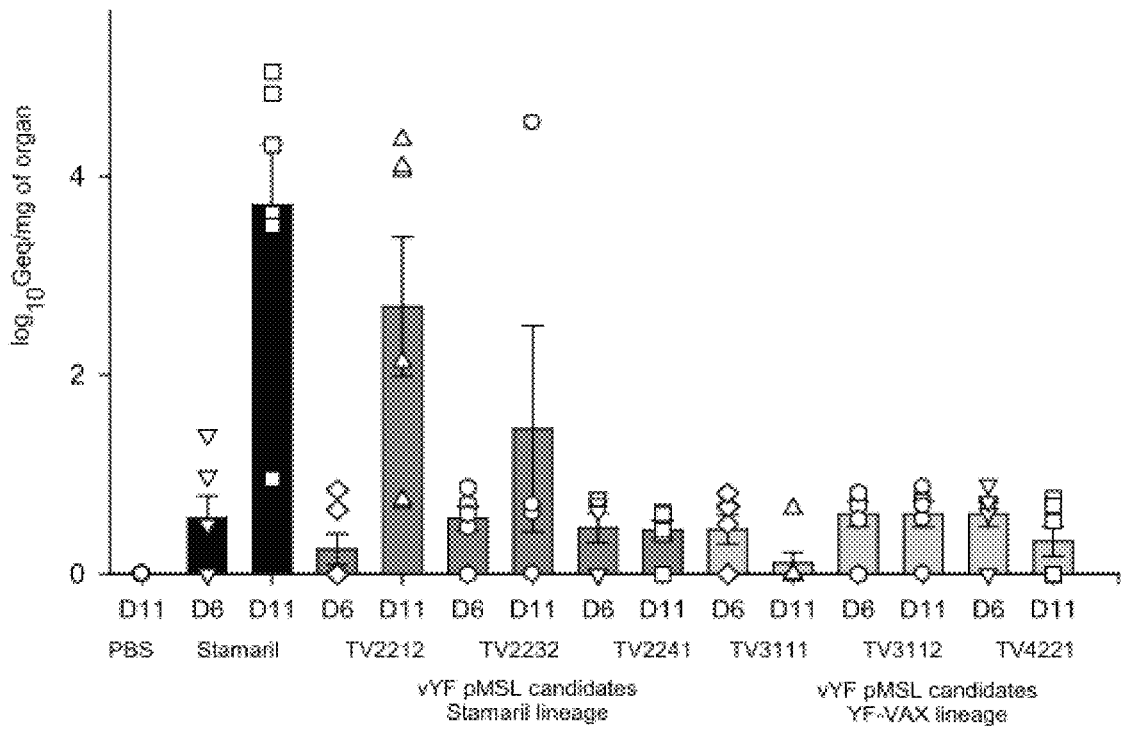

FIG. 5: Plots illustrating the viral load measured by YF-NS5 qRT-PCR in brain samples collected at D6 and D11 from A129 mice immunized at D0 with PBS (white bar); Stamaril® reference (black bars) or with vYF pMSL candidates deriving from the Stamaril® lineage (TV2212, TV2232 and TV2241; dark grey bars) or from the YF-VAX® lineage (TV3111, TV3112 and TV4221; light grey bars).

Figure 6:
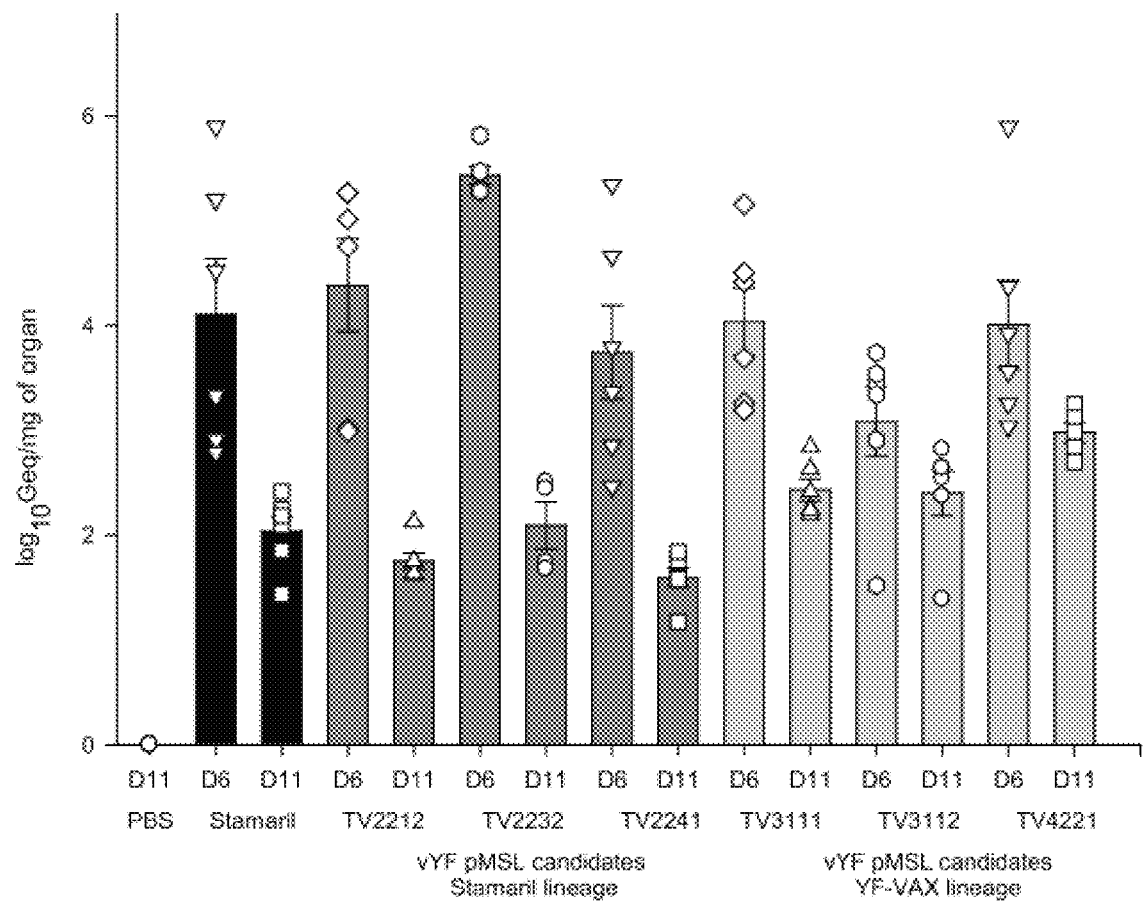

FIG. 6: Plots illustrating the viral load measured by YF-NS5 qRT-PCR in spleen samples collected at D6 and D11 from A129 mice immunized at D0 with PBS (white bar); Stamaril® reference (black bars) or with vYF pMSL candidates deriving from the Stamaril® lineage (TV2212, TV2232 and TV2241; dark grey bars) or from the YF-VAX® lineage (TV3111, TV3112 and TV4221; light grey bars).

Figure 7:
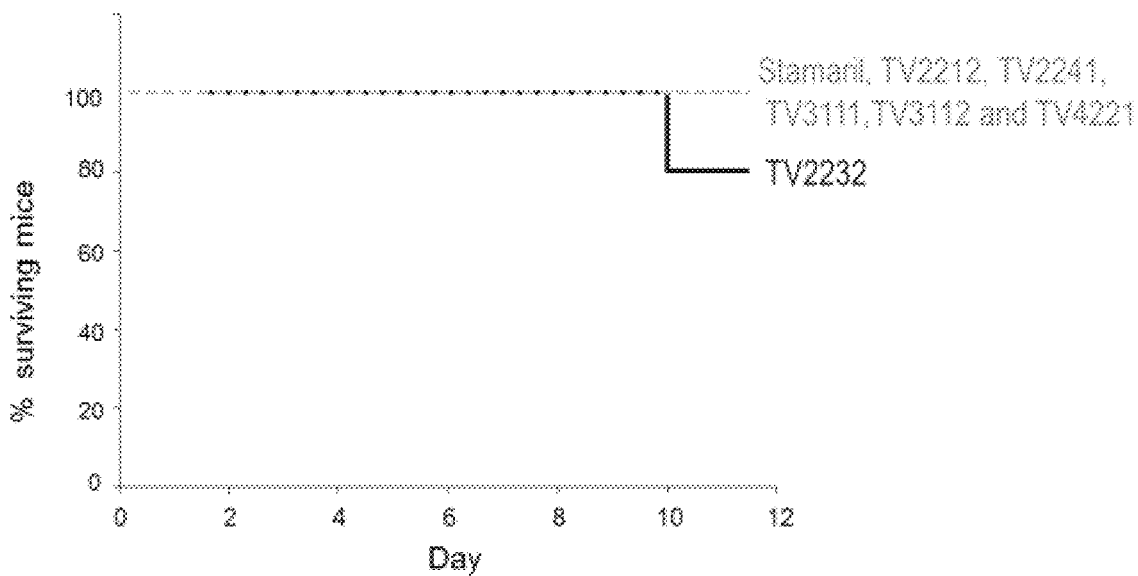

FIG. 7: Plots illustrating the Kaplan-Meier survival curves after a single immunization of A129 mice with Stamaril®, vYF strains TV221, TV2241, TV3111, TV3112, TV4221 (dotted lines) or TV2232 (plain line).

Figure 8:
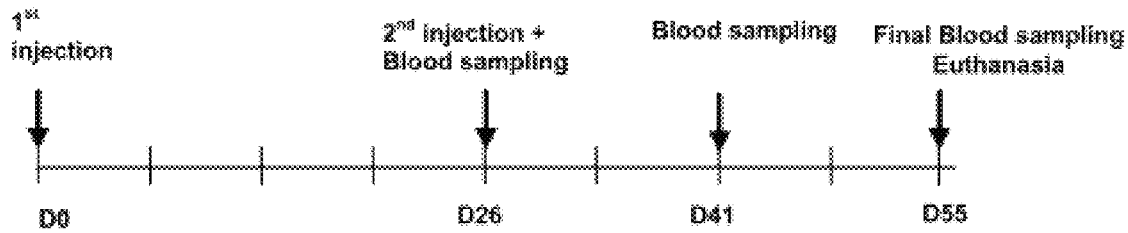

FIG. 8: Diagram illustrating the immunogenicity assay on a hamster model.

Figure 9:
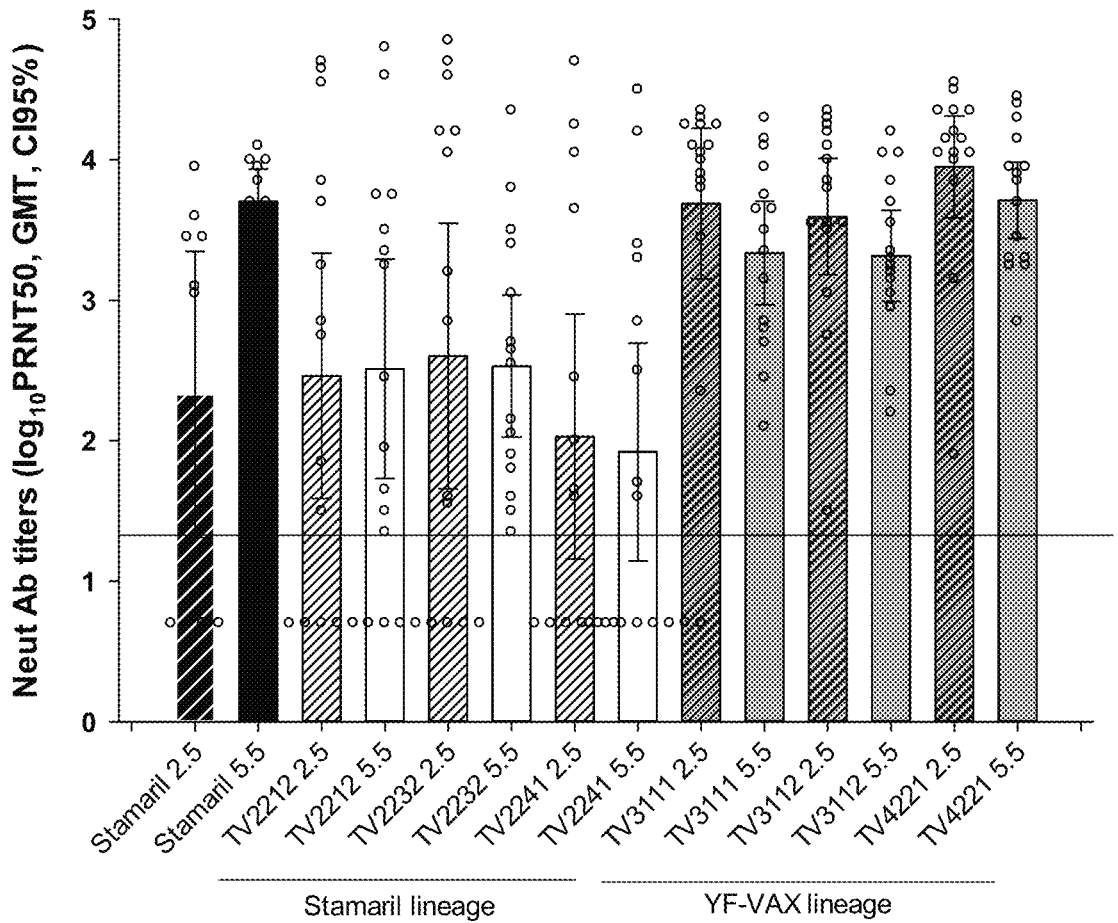

FIG. 9: Plots illustrating the neutralizing antibody titers specific to live-attenuated yellow fever virus strain measured by seroneutralization assay on Vero cells in sera collected at D26 from hamsters immunized at D0 with 2.5 or 5.5 $\log_{10}$ $CCID_{50}$/dose of vYF strains (TV2212, TV2232, TV2241, TV3111, TV3112 and TV4221) or Stamaril® reference vaccine. The horizontal line represents the responder threshold.

Figure 10:
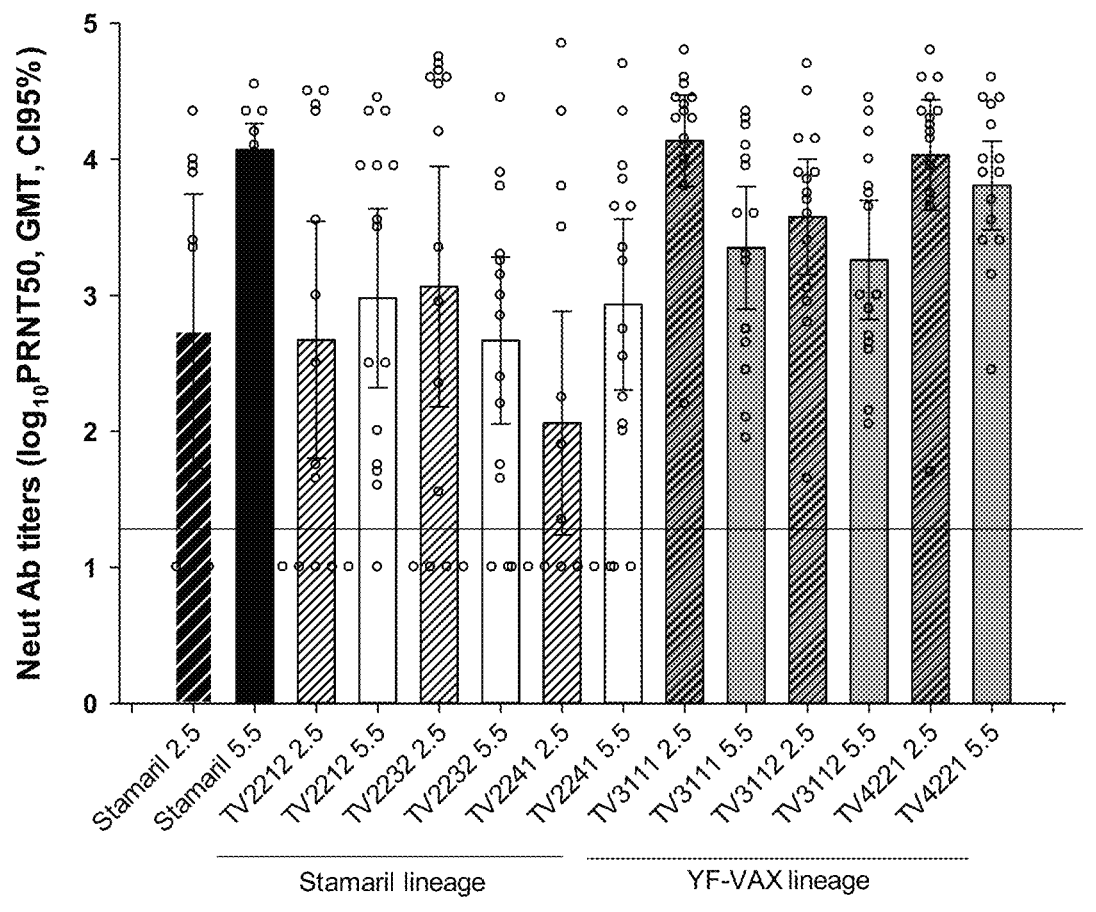

FIG. 10: Plots illustrating the neutralizing antibody titers specific to live-attenuated yellow fever virus strain measured by seroneutralization assay on Vero cells in sera collected at D41 from hamsters immunized at D0 and D26 with 2.5 or 5.5 $\log_{10}$ $CCID_{50}$/dose of vYF strains (TV2212, TV2232, TV2241, TV3111, TV3112 and TV4221) or Stamaril® reference vaccine. The horizontal line represents the responder threshold.

Figure 11:
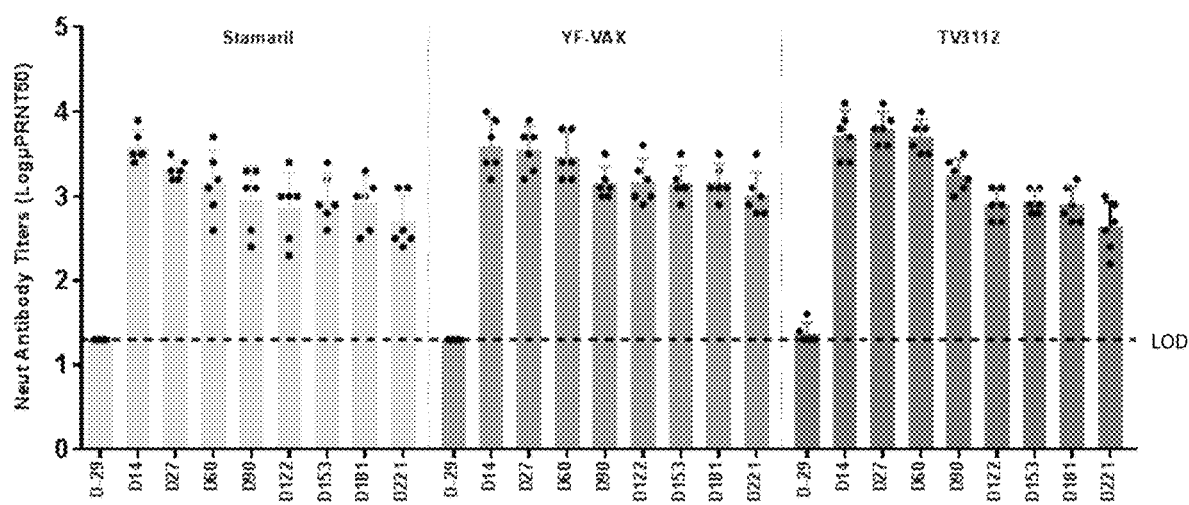

FIG. 11: Plots illustrating the neutralizing antibody response in monkeys vaccinated with vYF strain TV3112 in comparison with current vaccines Stamaril® and YF-VAX®. The horizontal line represents the limit of detection.

Figure 12:
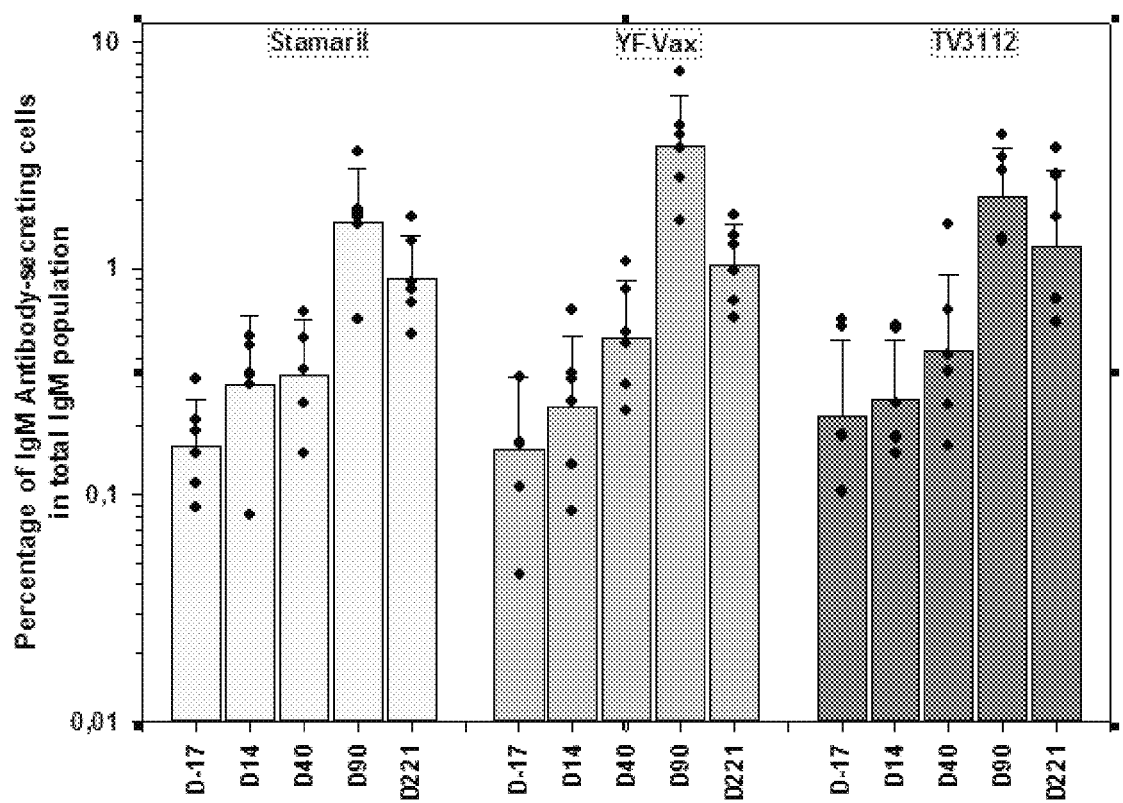

FIG. 12: Plots illustrating the YF-specific IgM responses from the B memory cells, in peripheral blood from monkeys vaccinated with the live-attenuated vYF strain TV3112 in comparison with the current reference vaccines Stamaril® and YF-VAX®. The results are expressed as the percentage of IgM antibody-secreting cells in total IgM population.

Figure 13:
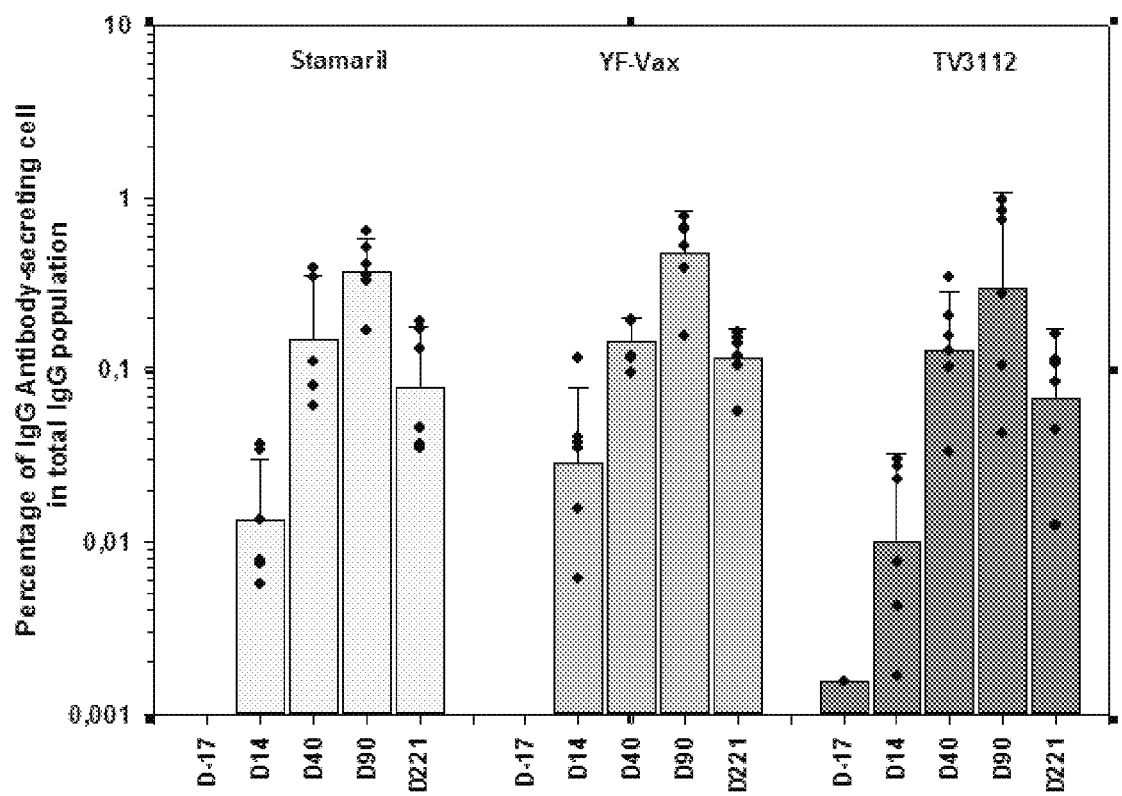

FIG. 13: Plots illustrating the YF-specific IgG responses from the B memory cells, in peripheral blood from monkeys vaccinated with the live-attenuated vYF strain TV3112 in comparison with the current reference vaccines Stamaril® and YF-VAX®. The results are expressed as the percentage of IgG antibody-secreting cells in total IgG population.

Figure 14:
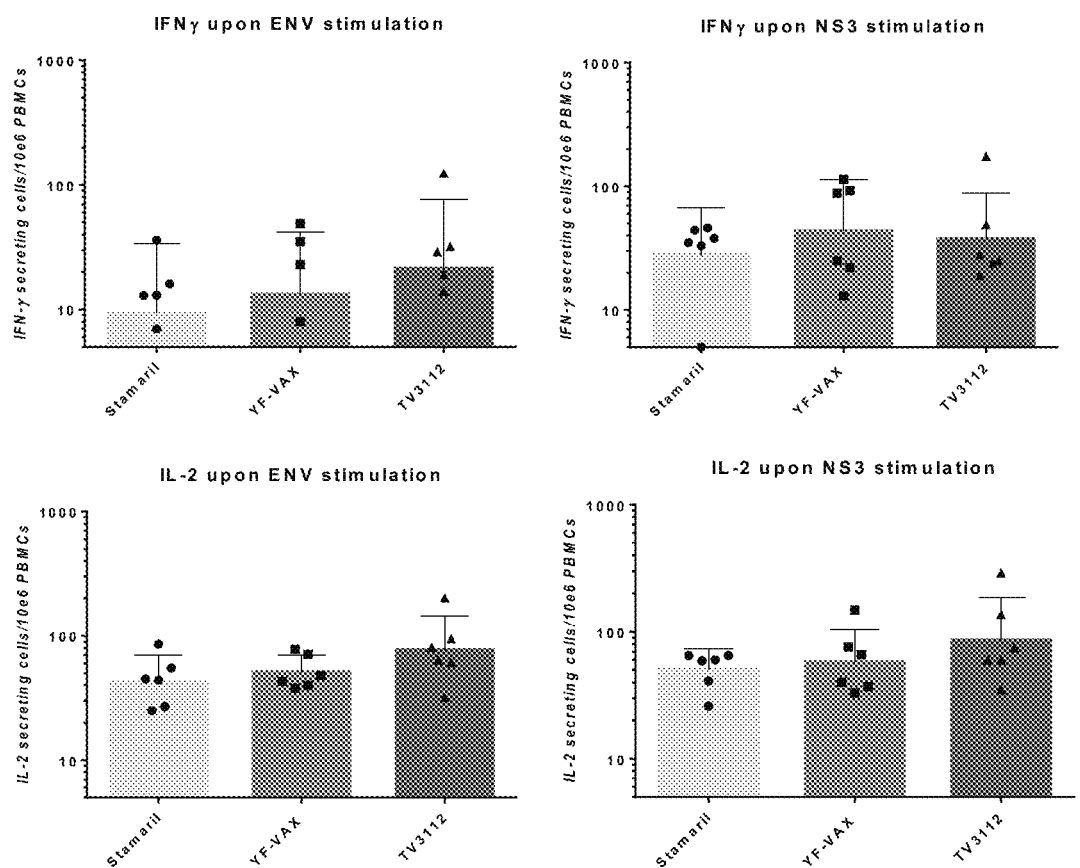

FIG. 14: Plots illustrating the IFN-γ (upper panels) and IL-2 (lower panels) specific T-cell responses in peripheral blood from monkeys vaccinated with vYF strain TV3112 upon stimulation with the envelope protein (ENV; left panels) or stimulation with the non-structural protein 3 (NS3; right panels), and comparison with current vaccines Stamaril® and YF-VAX®.

Figure 15:
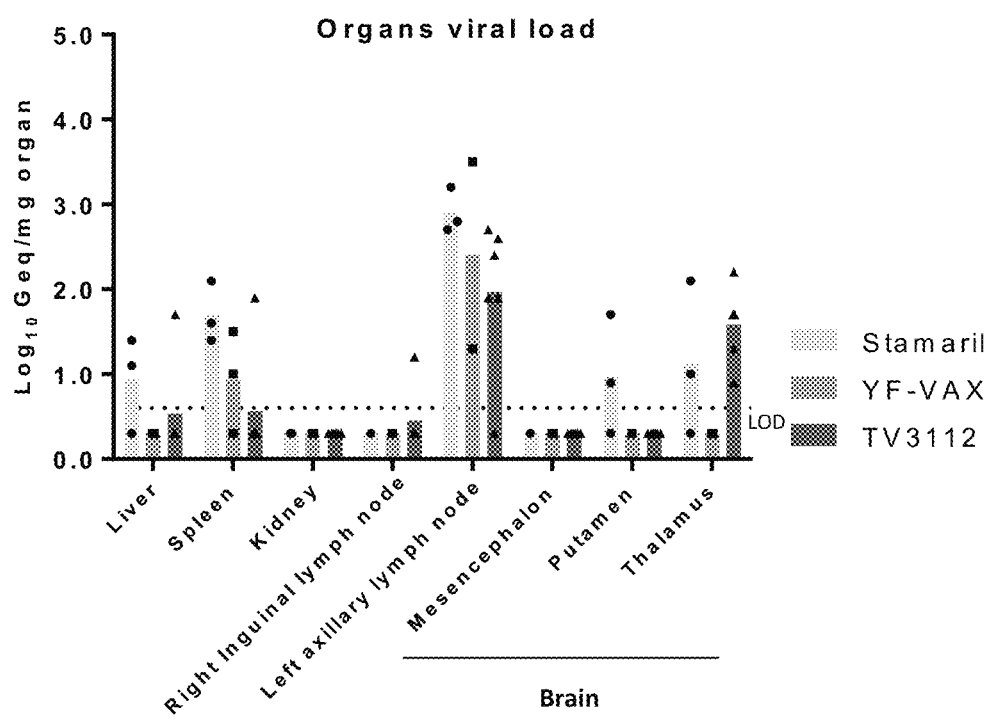

FIG. 15: Plots illustrating the viral load in organs from monkeys vaccinated with the live-attenuated vYF strain TV3112 in comparison with the current reference vaccines Stamaril® and YF-VAX®. Light grey bars and circles represent results from monkeys vaccinated with Stamaril®; medium grey bars and squares represent results from monkeys vaccinated with YF-VAX®; dark grey bars and triangles represent results from monkeys vaccinated with the live-attenuated vYF strain TV3112. The horizontal line represents the limit of detection.

DETAILED DESCRIPTION OF THE INVENTION

The present invention provides live-attenuated YFV strains adapted to grow on Vero cells, which have been obtained from a parent live-attenuated YFV strain that is adapted to grow on embryonated eggs. The live-attenuated YFV strains have been selected for their reduced neurovirulence in a mouse $LD_{50}$ test ($MLD_{50}$), as compared to the parent live-attenuated YFV strain.

As it will emerge from the present invention, the production of YFV by passaging on Vero cells allows providing stable, highly reproducible, high standard quality and quantity live-attenuated YFV strains that are subsequently suitable for preparing a vaccine against a YF infection.

Miscellaneous Definitions

Within the scope of the present invention, "YFV" relates to a yellow fever virus", whereas the term "vYF" denotes a Vero cells-adapted yellow fever virus, i.e. a yellow fever virus adapted to grow on Vero cells.

Therefore, within the scope of the present invention, "Vero cells-adapted yellow fever virus" (vYV) and "yellow fever virus adapted to grow on Vero cells" are intended to be interchangeable expressions.

Within the scope of the present invention, a virus adapted to grow on Vero cells is a virus which has undergone at least 3 successive passages on Vero cells. In some embodiments, the virus has undergone about 3, 4, 5, 6, 7, 8, 9, 10, 11, 12, 13, 14 or 15 successive passages on Vero cells.

By "passage", one may understand any step in which the virus undergoes at least one replication cycle in Vero cells, in particular any step of transfection, amplification or cloning of the virus in Vero cells.

The expression "live-attenuated yellow fever virus", as used herein, has the common meaning known by a man skilled in the art. In some embodiments, this expression refers to a live yellow fever virus having an attenuated neurovirulence and/or an attenuated viscerotropism.

Within the scope of the present invention, the term "neurovirulence" is intended to refer to the capacity of the virus to pass across the blood-brain barrier (neuro-invasiveness), to replicate in the brain tissue (neurotropism) and cause inflammation, neuronal damage and encephalitis (neurovirulence stricto sensu).

Within the scope of the present invention, the term "viscerotropism" refers to the capacity of the virus to replicate in extraneural tissues, cause viremia and damage vital organs, including the liver (Monath, 2005).

In some embodiments, said live-attenuated yellow fever virus is at least as attenuated as one of the current commercialized live-attenuated yellow fever vaccine strains, for instance Stamaril® or YF-VAX®.

In some embodiments, said live-attenuated yellow fever virus has a neurovirulence at least as attenuated as one of the current commercialized live-attenuated yellow fever vaccine strains, for instance Stamaril® or YF-VAX®.

In some embodiments, said live-attenuated yellow fever virus has a viscerotropism at least as attenuated as one of the current commercialized live-attenuated yellow fever vaccine strains, for instance Stamaril® or YF-VAX®.

In some embodiments, said live-attenuated yellow fever virus has a neurovirulence and a viscerotropism at least as attenuated as one of the current commercialized live-attenuated yellow fever vaccine strains, for instance Stamaril® or YF-VAX®.

The terms "comprising"/"comprises"/"comprise"/"comprised" encompass "including"/"includes"/"include"/"included" respectively as well as "consisting"/"consists"/"consist"/"consisted" respectively, e.g. a composition "comprising" component X may consist exclusively of component X or may include one or more additional components, e.g. component X and component Y.

As used herein, "$CCID_{50}$" refers to cell culture infectious dose 50%, i.e. the amount of a virus sufficient to cause a cytopathic effect in 50% of inoculated replicate cell cultures, as determined in an end-point dilution assay in monolayer cell cultures.

Following the standard definitions from the World Health Organization (WHO), the present invention refers to the below definitions (WHO Technical report series, No. 872, 1998).

A "master seed lot" ("MSL"), or "primary seed lot", as used herein, refers to a quantity of virus suspension that has been processed in a single production run and has a uniform composition.

A "working seed lot" ("WSL"), or "secondary seed lot", as used herein, refers to a quantity of virus suspension that has been processed in a single production run, and that is uniform with respect to composition, is fully characterized and is only one passage from a MSL. Within the scope of the present invention, material drawn from WSL is used for inoculating embryonated eggs, or suitable cell lines, in the preparation of vaccine.

A "plaque-forming unit" (PFU) as used herein, refers to the smallest quantity of a virus suspension that will produce a plaque in monolayer cell cultures.

A "median mouse lethal dose" (mouse $LD_{50}$ or $MLD_{50}$) as used herein, refers to the quantity of a virus suspension that will kill 50% of the mice injected with it.

Live-Attenuated YFV Adapted to Grow on Vero Cells (Also Referred as to "vYF Virus" for Vero Cells Adapted YF Virus)

In one aspect, the invention relates to a live-attenuated yellow fever virus strain adapted to grow on Vero cells from a parent yellow fever virus 17D substrain that is not adapted to grow on Vero cells. In various embodiments said live-attenuated yellow fever virus strain is less neurovirulent than said parent yellow fever virus 17D substrain.

In some embodiments, the parent yellow fever virus strain is a live-attenuated yellow fever virus strain adapted to grow on eggs.

In some embodiments, the eggs are embryonated hen eggs.

A "17D substrain" is a yellow fever strain having in its ancestors the 17D strain.

The "17D strain" has the common meaning known by a man skilled in the art. In some embodiments, "17D strain" refers to the yellow fever strain that was isolated from a mild human case, "Mr. Asibi", in Ghana in 1927 and was passaged 18 times in minced murine embryo tissue and then passaged 58 times in minced chicken embryo tissue as described in Monath (2005).

In some embodiments, the 17D substrain encompasses the 17D-204 substrain, the 17DD substrain, and/or the 17D-213 substrain as described in Monath (2005). In an exemplary embodiment, the RNA sequence of the YFV 17D-204 strain (Genbank accession number X03700), as previously disclosed by Rice et al., in 1985, may be represented by the RNA sequence SEQ ID NO. 1.

In some embodiments, the parent yellow fever virus strain is a yellow fever virus 17D-204 substrain.

In some embodiments, the parent YFV virus strain is the YFV 17D-204 derived YF-VAX® strain, the reference YFV strain used in the commercialized vaccine YF-VAX®.

In an exemplary embodiment, the RNA sequence of the YFV 17D-204 derived YF-VAX® strain may be represented by the RNA sequence SEQ ID NO. 2.

In some embodiments, the parent YFV virus strain is the YFV 17D-204 derived Stamaril® strain, the reference YFV strain used in the commercialized vaccine Stamaril®.

In an exemplary embodiment, the RNA sequence of the YFV 17D-204 derived Stamaril® strain may be represented by the RNA sequence SEQ ID NO. 3.

In an exemplary embodiment, the parent yellow fever virus 17D substrain comprises a RNA sequence of SEQ ID NO. 2.

In an exemplary embodiment, the parent yellow fever virus 17D substrain comprises a RNA sequence of SEQ ID NO. 3.

In an exemplary embodiment, the RNA sequence of the YFV 17D-213 strain (Genbank accession number U17067), as previously disclosed by Dos Santos et al., in 1995, may be represented by the RNA sequence SEQ ID NO. 4 and the RNA sequence of the YFV 17DD strain (Genbank accession number U17066), as also previously disclosed by Dos Santos et al., in 1995, may be represented by the RNA sequence SEQ ID NO. 5.

In an exemplary embodiment, the RNA sequence of the Asibi strain (Genbank accession number KF769016) may be represented by the RNA sequence SEQ ID NO. 6.

In some embodiments, the live-attenuated yellow fever virus strain is less neurovirulent than the parent yellow fever virus 17D-substrain in a mouse lethal dose 50 ($MLD_{50}$) test.

In some embodiments, a suitable mouse lethal dose 50 ($MLD_{50}$) test is performed according to the protocol disclosed in page 68 of the WHO Technical report series, No. 872, 1998 (incorporated by reference).

Within the scope of the present invention, the $MLD_{50}$ is the quantity of virus suspension estimated to produce fatal, specific encephalitis in 50% of intracerebrally inoculated mice.

In some embodiments, appropriate serial dilutions of the reconstituted vaccine are performed in phosphate-buffer, 0.75% serum albumin.

In an exemplary embodiment, 4-6 weeks old mice are injected intracerebrally under anaesthesia with an extemporaneous vaccine dilution. Groups of at least 6 mice are used for each dilution, and the series of dilutions should result in mortality rates after inoculation spanning the range 0-100%. Occurrences of death are recorded over a time period of 21 days. Mice dying from unrelated causes are removed from both the numerator and denominator of mortality calculations. Mice paralysed on the twenty-first day are counted as alive.

In certain embodiments, the neurovirulence in a mouse lethal dose 50 ($MLD_{50}$) test may be measured by the parameter $\log_{10} MLD_{50}/mL$.

In some embodiments, the live-attenuated YFV strain according to the present invention achieves a $\log_{10}$ $MLD_{50}$/mL of lower or equal to 4, lower or equal to 3.5, lower or equal to 3, or lower or equal to 2.5, in a mouse lethal dose 50 ($MLD_{50}$) test.

In an embodiment, a live-attenuated yellow fever virus strain according to the present invention is adapted to grow on VERO cells, is less neurovirulent than its parent yellow fever virus 17D substrain and is at least as attenuated in viscerotropism as its parent yellow fever virus 17D substrain.

In an embodiment, a live-attenuated yellow fever virus strain according to the present invention is adapted to grow on VERO cells, is less neurovirulent than its parent yellow fever virus 17D substrain, is at least as attenuated in viscerotropism as its parent yellow fever virus 17D substrain and is at least as immunogenic as its parent yellow fever virus 17D substrain.

In various embodiments, the present invention provides a live-attenuated YFV strain comprising a RNA sequence SEQ ID NO. 1, SEQ ID NO. 2, SEQ ID NO. 3, SEQ ID NO. 4, or SEQ ID NO. 5, wherein one or more nucleotide is mutated.

Within the scope of the present invention, the expression "one or more nucleotide" is intended to encompass 2, 3, 4, 5 or more nucleotides.

In other words, the expression "one or more nucleotide" is intended to encompass 1 nucleotide, 2, 3, 4, 5, 6, 7, 8, 9, 10, 11, 12, 13, 14 and 15, or more nucleotides.

In some embodiments, a mutation is a nucleotide substitution.

In some other embodiments, a mutation does not encompass a nucleotide insertion and a nucleotide deletion.

In some embodiments, the nucleotide substitution is silent. Alternatively, the nucleotide substitution may promote an amino acid substitution.

In one embodiment, two nucleotides are mutated in the RNA sequence SEQ ID NO. 1, SEQ ID NO. 2, SEQ ID NO. 3, SEQ ID NO. 4, or SEQ ID NO. 5.

In another embodiment, three nucleotides are mutated in the RNA sequence SEQ ID NO. 1, SEQ ID NO. 2, SEQ ID NO. 3, SEQ ID NO.4, or SEQ ID NO. 5.

In a further embodiment, four nucleotides are mutated in the RNA sequence SEQ ID NO. 1, SEQ ID NO. 2, SEQ ID NO. 3, SEQ ID NO.4, or SEQ ID NO. 5.

In a further embodiment, five nucleotides are mutated in the RNA sequence SEQ ID NO. 1, SEQ ID NO. 2, SEQ ID NO. 3, SEQ ID NO.4, or SEQ ID NO. 5.

Another aspect of the invention also relates to a live-attenuated yellow fever virus strain, which comprises a RNA sequence selected from SEQ ID NO. 1, SEQ ID NO. 2, SEQ ID NO. 3, SEQ ID NO. 4 and SEQ ID NO. 5, wherein at least the nucleotide at position 2411, position 3701 or position 6496 is mutated.

In some embodiments, the live-attenuated YFV strain comprises a RNA sequence selected from SEQ ID NO. 1, SEQ ID NO. 2, SEQ ID NO. 3, SEQ ID NO. 4 and SEQ ID NO. 5, wherein at least the nucleotide at position 2411 and the nucleotide at position 3701 are mutated.

In some embodiments, the live-attenuated YFV strain comprises a RNA sequence selected from SEQ ID NO. 1, SEQ ID NO. 2, SEQ ID NO. 3, SEQ ID NO. 4 and SEQ ID NO. 5, wherein at least the nucleotide at position 2411 and the nucleotide at position 6496 are mutated.

In some embodiments, the live-attenuated YFV strain comprises a RNA sequence selected from SEQ ID NO. 1, SEQ ID NO. 1, SEQ ID NO. 2, SEQ ID NO. 3, SEQ ID NO. 4 and SEQ ID NO. 5, wherein at least the nucleotide at position 3701 and the nucleotide at position 6496 are mutated.

In some embodiments, the live-attenuated YFV strain comprises a RNA sequence selected from SEQ ID NO. 1, SEQ ID NO. 1, SEQ ID NO. 2, SEQ ID NO. 3, SEQ ID NO. 4 and SEQ ID NO. 5, wherein at least the nucleotide at position 2411, the nucleotide at position 3701 and the nucleotide at position 6496 are mutated.

In certain embodiments, the nucleotide G (guanosine) at position 2411 of SEQ ID NO. 1, SEQ ID NO. 2, SEQ ID NO. 3, SEQ ID NO. 4, or SEQ ID NO. 5, is replaced by nucleotide U (uridine).

In certain embodiments, the nucleotide A (adenosine) at position 3701 of SEQ ID NO. 1, SEQ ID NO. 2, SEQ ID NO. 3, SEQ ID NO. 4, or SEQ ID NO. 5, is replaced by nucleotide G (guanosine).

In certain embodiments, the nucleotide A (adenosine) at position 6496 of SEQ ID NO. 1, SEQ ID NO. 2, SEQ ID NO. 3, SEQ ID NO. 4, or SEQ ID NO. 5, is replaced by nucleotide G (guanosine).

In some embodiments, the live-attenuated YFV strain is characterized as follows:
(i) the nucleotide G (guanosine) at position 2411 of SEQ ID NO. 1, SEQ ID NO. 2, SEQ ID NO. 3, SEQ ID NO. 4, or SEQ ID NO. 5, is replaced by nucleotide U (uridine), and
(ii) the nucleotide A (adenosine) at position 3701 of SEQ ID NO. 1, SEQ ID NO. 2, SEQ ID NO. 3, SEQ ID NO. 4, or SEQ ID NO. 5, is replaced by nucleotide G (guanosine).

In some other embodiments, the live-attenuated YFV strain is characterized as follows:
(i) the nucleotide G (guanosine) at position 2411 of SEQ ID NO. 1, SEQ ID NO. 2, SEQ ID NO. 3, SEQ ID NO. 4, or SEQ ID NO. 5, is replaced by nucleotide U (uridine), and
(ii) the nucleotide A (adenosine) at position 6496 of SEQ ID NO. 1, SEQ ID NO. 2, SEQ ID NO. 3, SEQ ID NO. 4, or SEQ ID NO. 5, is replaced by nucleotide G (guanosine).

In some other embodiments, the live-attenuated YFV strain is characterized as follows:
(i) the nucleotide A (adenosine) at position 3701 of SEQ ID NO. 1, SEQ ID NO. 2, SEQ ID NO. 3, SEQ ID NO. 4, or SEQ ID NO. 5, is replaced by nucleotide G (guanosine), and
(ii) the nucleotide A (adenosine) at position 6496 of SEQ ID NO. 1, SEQ ID NO. 2, SEQ ID NO. 3, SEQ ID NO. 4, or SEQ ID NO. 5, is replaced by nucleotide G (guanosine).

In certain embodiments, the live-attenuated YFV strain is characterized as follows:
(i) the nucleotide G (guanosine) at position 2411 of SEQ ID NO. 1, SEQ ID NO. 2, SEQ ID NO. 3, SEQ ID NO. 4, or SEQ ID NO. 5, is replaced by nucleotide U (uridine),
(ii) the nucleotide A (adenosine) at position 3701 of SEQ ID NO. 1, SEQ ID NO. 2, SEQ ID NO. 3, SEQ ID NO. 4, or SEQ ID NO. 5, is replaced by nucleotide G (guanosine); and
(iii) the nucleotide A (adenosine) at position 6496 of SEQ ID NO. 1, SEQ ID NO. 2, SEQ ID NO. 3, SEQ ID NO. 4, or SEQ ID NO. 5, is replaced by nucleotide G (guanosine).

In some embodiments, the live-attenuated YFV strain further comprises a mutation located at position 1408 of SEQ ID NO. 1, SEQ ID NO. 2, SEQ ID NO. 3, SEQ ID NO. 4, or SEQ ID NO. 5.

In some embodiments, the live-attenuated YFV strain comprises a RNA sequence selected in a group comprising SEQ ID NO. 1, SEQ ID NO. 2, SEQ ID NO. 3, SEQ ID NO. 4, or SEQ ID NO. 5, wherein at least the nucleotide at position 1408 and the nucleotide at position 2411 are mutated.

In some embodiments, the live-attenuated YFV strain comprises a RNA sequence selected in a group comprising SEQ ID NO. 1, SEQ ID NO. 2, SEQ ID NO. 3, SEQ ID NO. 4 and SEQ ID NO. 5, wherein at least the nucleotide at position 1408 and the nucleotide at position 3701 are mutated.

In some embodiments, the live-attenuated YFV strain comprises a RNA sequence selected in a group comprising SEQ ID NO. 1, SEQ ID NO. 2, SEQ ID NO. 3, SEQ ID NO. 4 and SEQ ID NO. 5, wherein at least the nucleotide at position 1408 and the nucleotide at position 6496 are mutated.

In some embodiments, the live-attenuated YFV strain comprises a RNA sequence selected in a group comprising SEQ ID NO. 1, SEQ ID NO. 2, SEQ ID NO. 3, SEQ ID NO. 4 and SEQ ID NO. 5, wherein at least the nucleotide at position 1408, the nucleotide at position 2411 and the nucleotide at position 3701 are mutated. In some embodiments, the live-attenuated YFV strain comprises a RNA sequence selected in a group comprising SEQ ID NO. 1, SEQ ID NO. 2, SEQ ID NO. 3, SEQ ID NO. 4 and SEQ ID NO. 5, wherein at least the nucleotide at position 1408, the nucleotide at position 2411 and the nucleotide at position 6496 are mutated.

In some embodiments, the live-attenuated YFV strain comprises a RNA sequence selected in a group comprising SEQ ID NO. 1, SEQ ID NO. 2, SEQ ID NO. 3, SEQ ID NO. 4 and SEQ ID NO. 5, wherein at least the nucleotide at position 1408, the nucleotide at position 3701 and the nucleotide at position 6496 are mutated.

In some embodiments, the live-attenuated YFV strain comprises a RNA sequence selected in a group comprising SEQ ID NO. 1, SEQ ID NO. 2, SEQ ID NO. 3, SEQ ID NO. 4 and SEQ ID NO. 5, wherein at least the nucleotide at position 1408, the nucleotide at position 2411, the nucleotide at position 3701 and the nucleotide at position 6496 are mutated.

In some embodiments, the nucleotide A (adenine) at position 1408 of SEQ ID NO. 1, SEQ ID NO. 2, SEQ ID NO. 3, SEQ ID NO. 4, or SEQ ID NO. 5, is replaced by nucleotide U (uridine).

In certain embodiments, the live-attenuated YFV strain is characterized as follows:
(i) the nucleotide G (guanosine) at position 2411 of SEQ ID NO. 1, SEQ ID NO. 2, SEQ ID NO. 3, SEQ ID NO. 4, or SEQ ID NO. 5, is replaced by nucleotide U (uridine),
(ii) the nucleotide A (adenosine) at position 3701 of SEQ ID NO. 1, SEQ ID NO. 2, SEQ ID NO. 3, SEQ ID NO. 4, or SEQ ID NO. 5, is replaced by nucleotide G (guanosine);
(iii) the nucleotide A (adenosine) at position 6496 of SEQ ID NO. 1, SEQ ID NO. 2, SEQ ID NO. 3, SEQ ID NO. 4, or SEQ ID NO. 5, is replaced by nucleotide G (guanosine); and
(iv) the nucleotide A (adenine) at position 1408 of SEQ ID NO. 1, SEQ ID NO. 2, SEQ ID NO. 3, SEQ ID NO. 4, or SEQ ID NO. 5, is replaced by nucleotide U (uridine).

In some embodiments, a live-attenuated YFV strain according to the present invention comprises a RNA sequence selected from SEQ ID NO. 1, SEQ ID NO. 2, SEQ ID NO. 3, SEQ ID NO. 4 and SEQ ID NO. 5, wherein at least one or more nucleotide at position 2411, 3701, 6496 and optionally 1408 is/are mutated, with the proviso that no nucleotide is mutated in a way that results into a reversion to the Asibi genotype (which may be represented by the RNA sequence SEQ ID NO. 6). In other words, if a nucleotide in SEQ ID NO. 1, SEQ ID NO. 2, SEQ ID NO. 3, SEQ ID NO. 4, or SEQ ID NO. 5 is different from the nucleotide at the same position in the Asibi genome (in SEQ ID NO. 6), this nucleotide in the RNA sequence of the live-attenuated YFV strain according to the present invention is not mutated in a way to become the nucleotide at the same position in the Asibi genome (in SEQ ID NO. 6). The nucleotides from SEQ ID NO. 1, SEQ ID NO. 2, SEQ ID NO. 3, SEQ ID NO. 4, or SEQ ID NO. 5 which are different from the nucleotides at the same positions in the Asibi genome may easily be identified by a sequence alignment (Needleman and Wunsch, (1970)) between SEQ ID NO. 1, SEQ ID NO. 2, SEQ ID NO. 3, SEQ ID NO. 4, or SEQ ID NO. 5 and Asibi sequence (SEQ ID NO. 6).

In some embodiments, a live-attenuated YFV strain according to the present invention comprises a RNA sequence comprising SEQ ID NO. 2, wherein at least one or more nucleotide at position 2411, 3701, 6496 and optionally 1408 is/are mutated, with the proviso that the nucleotides at the following positions in SEQ ID NO. 2 are not mutated in a way that results into a reversion to the Asibi genotype (SEQ ID NO. 6): 304, 370, 854, 883, 1127, 1140, 1431, 1482, 1491, 1572, 1750, 1819, 1870, 1887, 1946, 1965, 2112, 2193, 2219, 2356, 2687, 3371, 3613, 3817, 3860, 3925, 4007, 4013, 4022, 4054, 4056, 4289, 4387, 4505, 4507, 4612, 4864, 4873, 5153, 5194, 5362, 5431, 5473, 5926, 6023, 6448, 6876, 7171, 7496, 7571, 7580, 7642, 7701, 7945, 8008, 8629, 10142, 10285, 10312, 10338, 10367, 10418, 10550 and 10800.

TABLE 1

Nucleotide differences between SEQ ID NO. 2 and Asibi genomic RNA sequence (SEQ ID NO. 6).

| Nucleotide position in SEQ ID NO. 2 | Nucleotide in Asibi KF769016 | Nucleotide in SEQ ID NO. 2 | Protein-Amino acid position | Amino acid in Asibi KF769016 | Amino acid in SEQ ID NO. 2 |
|---|---|---|---|---|---|
| 304 | G | A | C-62 | T | T |
| 370 | U | C | C-84 | V | V |
| 854 | C | U | M-36 | L | F |
| 883 | A | G | M-45 | T | T |
| 1127 | G | A | E-52 | G | R |
| 1140 | C | U | E-56 | A | V |

TABLE 1-continued

Nucleotide differences between SEQ ID NO. 2 and Asibi genomic RNA sequence (SEQ ID NO. 6).

| Nucleotide position in SEQ ID NO. 2 | Nucleotide in Asibi KF769016 | Nucleotide in SEQ ID NO. 2 | Protein-Amino acid position | Amino acid in Asibi KF769016 | Amino acid in SEQ ID NO. 2 |
|---|---|---|---|---|---|
| 1431 | A | C | E-153 | N | T |
| 1482 | C | U | E-170 | A | V |
| 1491 | C | U | E-173 | T | I |
| 1572 | A | C | E-200 | L | T |
| 1750 | C | U | E-258 | T | T |
| 1819 | C | U | E-281 | S | S |
| 1870 | G | A | E-299 | M | I |
| 1887 | C | U | E-305 | S | F |
| 1946 | C | U | E-325 | P | S |
| 1965 | A | G | E-331 | K | R |
| 2112 | C | G | E-380 | T | R |
| 2193 | C | U | E-407 | A | V |
| 2219 | G | A | E-416 | A | T |
| 2356 | C | U | E-460 | L | L |
| 2687 | C | U | NS1-79 | L | F |
| 3371 | A | G | NS1-307 | I | V |
| 3613 | G | A | NS2a-35 | V | V |
| 3817 | A | G | NS2a-103 | V | V |
| 3860 | A | G | NS2a-118 | R | V |
| 3925 | A | U | NS2a-139 | V | V |
| 4007 | A | G | NS2a-167 | T | A |
| 4013 | C | U | NS2a-169 | P | F |
| 4022 | A | G | NS2a-172 | T | A |
| 4054 | C | U | NS2a-182 | N | N |
| 4056 | C | U | NS2a-183 | S | F |
| 4289 | A | C | NS2b-37 | I | L |
| 4387 | A | G | NS2b-69 | G | G |
| 4505 | A | C | NS2b-108 | I | L |
| 4507 | U | C | | | |
| 4612 | U | C | NS3-14 | I | I |
| 4864 | A | G | NS3-98 | Q | Q |
| 4873 | U | G | NS3-101 | A | A |
| 5153 | A | G | NS3-195 | I | V |
| 5194 | U | C | NS3-208 | F | F |
| 5362 | C | U | NS3-264 | A | A |
| 5431 | C | U | NS3-287 | I | I |
| 5473 | C | U | NS3-301 | A | A |
| 5926 | C | U | NS3-452 | R | R |
| 6023 | G | A | NS3-485 | D | N |
| 6448 | G | U | NS4a-3 | A | A |
| 6876 | U | C | P2k-20 | V | A |
| 7171 | A | G | NS4b-95 | I | M |
| 7496 | U | C | NS4b-204 | L | L |
| 7571 | C | A | NS4b-229 | R | R |
| 7580 | U | C | NS4b-232 | Y | H |
| 7642 | U | C | NS5-2 | S | S |
| 7701 | A | G | NS5-22 | Q | R |
| 7945 | C | U | NS5-103 | F | F |
| 8008 | U | C | NS5-124 | I | I |
| 8629 | C | U | NS5-331 | Y | Y |
| 10142 | G | A | NS5-836 | E | K |
| 10285 | U | C | NS5-883 | Y | Y |
| 10312 | A | G | NS5-892 | R | R |
| 10338 | C | U | NS5-901 | P | L |
| 10367 | U | C | 3'UTR | — | — |
| 10418 | U | C | 3'UTR | — | — |
| 10550 | U | C | 3'UTR | — | — |
| 10800 | G | A | 3'UTR | — | — |

In some embodiments, a live-attenuated YFV strain according to the present invention comprises a RNA sequence SEQ ID NO. 7. Advantageously, the live-attenuated YFV strain according to the present invention comprises a RNA sequence which differs by a limited number of mutations, e.g. no more than 5, no more than 4, no more than 3, or no more than 2, from SEQ ID NO. 7. Advantageously, the live-attenuated YFV strain according to the present invention comprises a RNA sequence which differs by a limited number of mutations, e.g. no more than 5, no more than 4, no more than 3, or no more than 2, from SEQ ID NO. 7, with the proviso that no nucleotide is mutated in a way that results into a reversion to the Asibi genotype. In an exemplary embodiment, the genomic RNA sequence of a live-attenuated YFV strain according to the present invention may consist of the nucleotide sequence SEQ ID NO. 7.

In some embodiments, a live-attenuated YFV strain according to the present invention comprises a RNA sequence SEQ ID NO. 8. Advantageously, the live-attenuated YFV strain according to the present invention comprises a RNA sequence which differs by a limited number of mutations, e.g. no more than 5, no more than 4, no more than 3, or no more than 2, from SEQ ID NO. 8. Advantageously, the live-attenuated YFV strain according to the present invention comprises a RNA sequence which differs by a limited number of mutations, e.g. no more than 5, no more than 4, no more than 3, or no more than 2, from SEQ ID NO. 8, with the proviso that no nucleotide is mutated in a way that results into a reversion to the Asibi genotype. In an exemplary embodiment, the genomic RNA sequence of a live-attenuated YFV strain according to the present invention may consist of the nucleotide sequence SEQ ID NO. 8.

As mentioned above, the YFV nucleic acid encodes 11 proteins, as follows:
- the capsid protein (C protein), which precursor is 121 aa in length, and the mature protein is 101 aa in length,
- a pre-membrane protein (prM protein) of 164 aa in length, which is the precursor of the membrane protein (M protein), of 75 aa in length,
- an envelope protein (E protein), which is 493 aa in length,
- non-structural protein 1 (NS1), which is 352 aa in length,
- non-structural protein 2a (NS2a), which is 224 aa in length,
- non-structural protein 2b (NS2b), which is 130 aa in length,
- non-structural protein 3 (NS3), which is 623 aa in length,
- non-structural protein 4a (NS4a), which is 126 aa in length,
- non-structural peptide P2k, which is 23 aa in length,
- non-structural protein 4b (NS4b) and which is 250 aa in length,
- non-structural protein 5 (NS5), which is 905 aa in length.

In some embodiments, the live-attenuated yellow fever virus strain comprises a nucleic acid comprising a mutation in the codon for the amino acid at position 480 of the envelope protein (E), a mutation in the codon for the amino acid at position 65 of the non-structural protein 2A (NS2a), a mutation in the codon for the amino acid at position 19 of the non-structural protein 4A (NS4a) and/or a mutation in the codon for the amino acid at position 145 of the envelope protein (E).

In some embodiments, the live-attenuated yellow fever virus strain comprises a nucleic acid comprising a mutation in the codon for the amino acid at position 480 of the envelope protein (E) and a mutation in the codon for the amino acid at position 65 of the non-structural protein 2A (NS2a).

In some embodiments, the live-attenuated yellow fever virus strain comprises a nucleic acid comprising a mutation in the codon for the amino acid at position 480 of the envelope protein (E), a mutation in the codon for the amino acid at position 65 of the non-structural protein 2A (NS2a) and a mutation in the codon for the amino acid at position 19 of the non-structural protein 4A (NS4a).

In some embodiments, the live-attenuated yellow fever virus strain comprises a nucleic acid comprising a mutation in the codon for the amino acid at position 480 of the envelope protein (E), a mutation in the codon for the amino acid at position 65 of the non-structural protein 2A (NS2a), a mutation in the codon for the amino acid at position 19 of the non-structural protein 4A (NS4a) and a mutation in the codon for the amino acid at position 145 of the envelope protein (E).

In some embodiments, the live-attenuated yellow fever virus strain comprises a nucleic acid comprising:
i) a mutation in the codon for the amino acid at position 480 of the envelope protein (E) which results in an amino acid change from valine to leucine, or
ii) a mutation in the codon for the amino acid at position 65 of the non-structural protein 2A (NS2a) which results in an amino acid change from methionine to valine.

In some embodiments, the live-attenuated yellow fever virus strain according to the present invention comprises a nucleic acid comprising:
i) a mutation in the codon for the amino acid at position 480 of the envelope protein (E) which results in an amino acid change from valine to leucine, and
ii) a mutation in the codon for the amino acid at position 65 of the non-structural protein 2A (NS2a) which results in an amino acid change from methionine to valine.

In some embodiments, the nucleic acid further comprises a mutation in the codon for the amino acid at position 19 of the non-structural protein 4A (NS4a) which results in a codon change from AAA to AAG.

In some embodiments, the mutation in the codon for the amino acid at position 480 of the envelope protein (E) results in a codon change from GUA to UUA, UUG, CUU, CUC, CUA or CUG. In an embodiment, the codon change is from GUA to UUA.

In some embodiments, the mutation in the codon for the amino acid at position 65 of the non-structural protein 2A (NS2a) results in a codon change from AUG to GUG, GUU, GUC or GUA. In an embodiment, the codon change is from AUG to GUG.

In some embodiments, the nucleic acid further comprises a mutation in the codon for the amino acid at position 145 of the envelope protein (E) which results in a codon change from GUA to GUU.

In some embodiments, the live-attenuated yellow fever virus strain according to the present invention comprises a nucleic acid comprising:
i) a mutation in the codon for the amino acid at position 480 of the envelope protein (E) which results in an amino acid change from valine to leucine;
ii) a mutation in the codon for the amino acid at position 65 of the non-structural protein 2A (NS2a) which results in an amino acid change from methionine to valine; and
iii) a mutation in the codon for the amino acid at position 19 of the non-structural protein 4A (NS4a) which results in a codon change from AAA to AAG.

In some embodiments, the live-attenuated yellow fever virus strain according to the present invention comprises a nucleic acid comprising:
i) a mutation in the codon for the amino acid at position 480 of the envelope protein (E) which results in an amino acid change from valine to leucine;
ii) a mutation in the codon for the amino acid at position 65 of the non-structural protein 2A (NS2a) which results in an amino acid change from methionine to valine;
iii) a mutation in the codon for the amino acid at position 19 of the non-structural protein 4A (NS4a) which results in a codon change from AAA to AAG; and
iv) a mutation in the codon for the amino acid at position 145 of the envelope protein (E) which results in a codon change from GUA to GUU.

In some embodiments, the live-attenuated yellow fever virus strain comprises an envelope protein comprising a mutation at position 480. In particular, the live-attenuated yellow fever virus strain according to the present invention comprises an envelope protein comprising a mutation at position 480 which results in an amino acid change from valine to leucine.

In some embodiments, the live-attenuated yellow fever virus strain comprises an envelope protein comprising a leucine residue at the position within the protein that corresponds to position 480 of SEQ ID NO. 15. In particular, said envelope protein comprises a sequence at least 90%, 95%, 98% or 100% identical to the sequence of SEQ ID NO. 15.

In particular in the nucleic acid of the live-attenuated yellow fever virus strain of the invention no nucleotide is mutated in a way that results into a reversion to the Asibi genotype (SEQ ID NO. 6). For instance the nucleic acid of the live-attenuated yellow fever virus strain comprises no mutation for the nucleotides at the following positions in SEQ ID NO. 2 in a way that results into a reversion to the Asibi genotype (SEQ ID NO. 6): 304, 370, 854, 883, 1127, 1140, 1431, 1482, 1491, 1572, 1750, 1819, 1870, 1887, 1946, 1965, 2112, 2193, 2219, 2356, 2687, 3371, 3613, 3817, 3860, 3925, 4007, 4013, 4022, 4054, 4056, 4289, 4387, 4505, 4507, 4612, 4864, 4873, 5153, 5194, 5362, 5431, 5473, 5926, 6023, 6448, 6876, 7171, 7496, 7571, 7580, 7642, 7701, 7945, 8008, 8629, 10142, 10285, 10312, 10338, 10367, 10418, 10550 and 10800.

In some embodiments, the live-attenuated yellow fever virus strain comprises a nucleic acid molecule encoding:
(i) an envelope protein comprising a mutation at position 480, and
(ii) a NS2a protein comprising a mutation at position 65.

In particular, the nucleic acid molecule of the live-attenuated yellow fever virus strain further comprises a mutation in the codon for the amino acid at position 19 of the non-structural protein 4A (NS4a) and/or a mutation in the codon for the amino acid at position 145 of the envelope protein (E).

In some embodiments, the live-attenuated yellow fever virus strain according to the present invention comprises a nucleic acid molecule encoding:
(i) an envelope protein comprising a mutation at position 480 which results in an amino acid change from valine to leucine, and
(ii) a NS2a protein comprising a mutation at position 65 which results in an amino acid change from methionine to valine.

In particular, the nucleic acid further comprises a mutation in the codon for the amino acid at position 19 of the non-structural protein 4A (NS4a) which results in a codon change from AAA to AAG and/or a mutation in the codon for the amino acid at position 145 of the envelope protein (E) which results in a codon change from GUA to GUU.

In particular in the nucleic acid of the live-attenuated yellow fever virus strain of the invention no nucleotide is mutated in a way that results into a reversion to the Asibi genotype (SEQ ID NO. 6). For instance the nucleic acid of the live-attenuated yellow fever virus strain comprises no mutation for the nucleotides at the following positions in SEQ ID NO. 2 in a way that results into a reversion to the Asibi genotype (SEQ ID NO. 6): 304, 370, 854, 883, 1127, 1140, 1431, 1482, 1491, 1572, 1750, 1819, 1870, 1887, 1946, 1965, 2112, 2193, 2219, 2356, 2687, 3371, 3613, 3817, 3860, 3925, 4007, 4013, 4022, 4054, 4056, 4289, 4387, 4505, 4507, 4612, 4864, 4873, 5153, 5194, 5362, 5431, 5473, 5926, 6023, 6448, 6876, 7171, 7496, 7571, 7580, 7642, 7701, 7945, 8008, 8629, 10142, 10285, 10312, 10338, 10367, 10418, 10550 and 10800.

In some embodiments, the live-attenuated yellow fever virus strain according to the present invention comprises a nucleic acid molecule encoding:
(i) an envelope protein which comprises a leucine residue at the position within the protein that corresponds to position 480 of SEQ ID NO. 15, and
(ii) an NS2a protein which comprises a valine residue at the position within the protein that corresponds to position 65 of SEQ ID NO. 16.

In particular, said envelope protein comprises a sequence at least 90%, 95%, 98% or 100% identical to the sequence of SEQ ID NO. 15 and said NS2a protein comprises a sequence at least 90%, 95%, 98% or 100% identical to the sequence of SEQ ID NO. 16.

The nucleic acid of the live-attenuated yellow fever virus strain of the invention may further comprise a G nucleotide at position within the nucleic acid coding for the non-structural protein 4A (NS4a) that corresponds to position 57 of SEQ ID NO. 17 and/or a U nucleotide at position within the nucleic acid coding for the envelope protein (E) that corresponds to position 435 of SEQ ID NO. 18. In particular, the live-attenuated yellow fever virus strain of the invention may comprise a nucleic acid molecule comprising a nucleic acid coding for the non-structural protein 4A (NS4a) which comprises a sequence at least 90%, 95%, 98% or 100% identical to the sequence of SEQ ID NO. 17 and/or a nucleic acid coding for the envelope protein (E) which comprises a sequence at least 90%, 95%, 98% or 100% identical to the sequence of SEQ ID NO. 18.

In particular in the nucleic acid of the live-attenuated yellow fever virus strain of the invention no nucleotide is mutated in a way that results into a reversion to the Asibi genotype (SEQ ID NO. 6). For instance the nucleic acid of the live-attenuated yellow fever virus strain comprises no mutation for the nucleotides at the following positions in SEQ ID NO. 2 in a way that results into a reversion to the Asibi genotype (SEQ ID NO. 6): 304, 370, 854, 883, 1127, 1140, 1431, 1482, 1491, 1572, 1750, 1819, 1870, 1887, 1946, 1965, 2112, 2193, 2219, 2356, 2687, 3371, 3613, 3817, 3860, 3925, 4007, 4013, 4022, 4054, 4056, 4289, 4387, 4505, 4507, 4612, 4864, 4873, 5153, 5194, 5362, 5431, 5473, 5926, 6023, 6448, 6876, 7171, 7496, 7571, 7580, 7642, 7701, 7945, 8008, 8629, 10142, 10285, 10312, 10338, 10367, 10418, 10550 and 10800.

In some embodiments, the nucleic acid comprises the RNA sequence of a 17D substrain, comprising the mutations according to the present invention as described above.

In some embodiments, the nucleic acid comprises the RNA sequence of a 17D-204 substrain, comprising the mutations according to the present invention as described above.

In some embodiments, the nucleic acid comprises the RNA sequence SEQ ID NO. 1, SEQ ID NO. 2, SEQ ID NO. 3, SEQ ID NO. 4, or SEQ ID NO.5, comprising the mutations according to the present invention as described above.

In an exemplary embodiment, the nucleic acid comprises the RNA sequence SEQ ID NO. 2, comprising the mutations according to the present invention as described above.

As it will emerge from the example section hereunder, the mutations as defined above allow providing YFV strains adapted to grow on VERO cells and that have an attenuated virulence, such as an attenuated neurovirulence, as compared to the parent YFV strain, and which virulence is compatible with the use of these strains as vaccines or in vaccine compositions. In an embodiment, the mutations as defined above allow providing YFV strains adapted to grow on VERO cells and that are less neurovirulent, as compared to the parent YFV strain, and are at least as attenuated in viscerotropism, as compared to the parent YFV strain. In an embodiment, the mutations as defined above allow providing YFV strains adapted to grow on VERO cells and that are less neurovirulent, as compared to the parent YFV strain, are at least as attenuated in viscerotropism, as compared to the parent YFV strain, and are at least as immunogenic, as compared to the parent YFV strain.

Immunogenic, Vaccine and Pharmaceutical Compositions

In another aspect, the invention also relates to an immunogenic composition comprising a live-attenuated YFV strain according to the present invention.

Within the scope of the present invention, the term "immunogenic" refers to the capability of the composition to promote an antibody-mediated and/or a cell-mediated immunity and/or an immunological memory.

In some embodiment, the immunogenic composition may be employed in order to generate neutralizing antibodies against a yellow fever virus.

In another aspect, the invention further relates to an immunogenic composition comprising a live-attenuated yellow fever virus strain according to the present invention and a pharmaceutically acceptable vehicle.

In some embodiments, the invention also relates to a vaccine composition comprising a live-attenuated virus strain according to the present invention, and/or a vaccine composition comprising the immunogenic composition according to the present invention.

In some embodiments, a vaccine composition may not comprise any adjuvant.

Within the scope of the present invention, an "adjuvant" refers to any substance intended to enhance relevant immune response and subsequent clinical efficacy of a vaccine.

Alternatively, a vaccine composition may further comprise one or more adjuvants.

In some embodiments, the adjuvant may include a mineral salt, an emulsion, a microbial natural or synthetic derivative, a combination adjuvant, a cytokine-derived or accessory molecules-derived adjuvant, a particulate formulation, and the like. The preparation and use of adjuvants are well known in the art.

In some embodiments, the present invention provides an immunogenic composition comprising a live-attenuated YFV strain as described herein and a pharmaceutically acceptable carrier.

In some embodiments, the present invention provides a pharmaceutical composition comprising a live attenuated YFV strain as described herein and a pharmaceutically acceptable carrier.

In the context of the invention, the expression "pharmaceutically acceptable vehicle" refers to a vehicle that is physiologically acceptable for administration to a human being, while retaining the physiological activity of the immunogenic composition according to the invention, i.e. its ability to induce an immune response. One exemplary pharmaceutically acceptable vehicle is a physiological saline buffer. Other physiologically acceptable vehicles are known to those skilled in the art and are described, for instance, in Remington's Pharmaceutical Sciences (18$^{th}$ edition), ed. A. Gennaro, 1990, Mack Publishing Company, Easton, Pa. An immunogenic composition as described herein may optionally contain pharmaceutically acceptable auxiliary substances as required to approximate physiological conditions, such as pH adjusting and buffering agents, tonicity adjusting agents, wetting agents and the like. In addition, the vaccine composition may optionally comprise pharmaceutically acceptable additives including, for example, diluents, binders, stabilizers, and preservatives.

In various embodiments, the pH of the immunogenic composition is between 5.5 and 8, such as between 6.5 and 7.5 (e.g. about 7). Stable pH may be maintained by the use of a buffer. Thus, in some embodiments, the immunogenic composition includes a buffer. Immunogenic compositions may be isotonic with respect to humans. The immunogenic composition may also comprise one or several additional salts, such as NaCl. The preparation and use of pharmaceutically acceptable carriers are well known in the art.

In practice, the immunogenic composition and/or the vaccine composition and/or the pharmaceutical composition comprising a live-attenuated YFV strain according to the present invention may be prepared using the conventional and good practices in the field.

In some embodiments, the immunogenic composition, the vaccine composition and/or the pharmaceutical composition according to the present invention may comprise one or more suitable diluent and/or excipient.

In various embodiments, the pharmaceutical compositions, the immunogenic compositions and the vaccine compositions may be sterilized by conventional sterilization techniques, or may be sterile filtered. The resulting aqueous solutions may be packaged and stored in liquid form or lyophilized, the lyophilized preparation being reconstituted with a sterile aqueous carrier prior to administration. In an exemplary embodiment, the pharmaceutical compositions, the immunogenic compositions and the vaccine compositions are packaged and stored as micropellets via a prilling process as described in WO 2009/109550. In an embodiment the pharmaceutical compositions, the immunogenic compositions, and/or the vaccine compositions are lyophilized or spray-freeze dried.

Method for Obtaining a Live-Attenuated YFV Strain

A further aspect of the invention relates to a method for obtaining a live-attenuated yellow fever virus strain adapted to grow on Vero cells, comprising the steps of:
a) purifying the viral genomic RNA of a parent live-attenuated yellow fever virus strain that is not adapted to grow on Vero cells, and that is optionally adapted to grow on eggs;
b) transfecting Vero cells with the viral genomic RNA purified in step a), whereby transfected Vero cells are obtained;
c) growing the transfected Vero cells obtained in step b) in a culture medium, whereby a first yellow fever virus population is obtained and further recovered;
d) amplifying the recovered first yellow fever virus population obtained at the end of step c) 2 times or more on fresh Vero cells, whereby a second yellow fever virus population is obtained;
e) cloning the second yellow fever virus population obtained in step d) by two or more successive plaque purifications on Vero cells whereby a plurality of yellow fever virus clones is obtained;
f) amplifying separately each of the recovered yellow fever virus clones obtained at the end of step e) 2 times or more on fresh Vero cells, whereby a plurality of yellow fever virus strains is obtained; and g) selecting from the said plurality of yellow fever virus strains recovered in step f) one or more live-attenuated yellow fever virus strain that is less neurovirulent than the parent live-attenuated yellow fever virus strain, in a mouse lethal dose 50 ($MLD_{50}$) test.

In some embodiments, step d) of the method of the present invention above is conducted 2, 3, 4, 5, 6, or more times. In some embodiments, the cloning at step e) of the method of the present invention above is conducted by 2, 3, 4, 5, 6, or more successive plaque purifications on Vero cells. In some embodiments, step 0 of the method of the present invention above is conducted 2, 3, 4, 5, 6, or more times.

A further aspect of the invention relates to a method for obtaining a live-attenuated yellow fever virus strain adapted to grow on Vero cells, comprising the steps of:
  a) purifying the viral genomic RNA of a parent live-attenuated yellow fever virus strain that is not adapted to grow on Vero cells, and that is optionally adapted to grow on eggs;
  b) transfecting Vero cells with the viral genomic RNA purified in step a), whereby transfected Vero cells are obtained;
  c) growing the transfected Vero cells obtained in step b) in a culture medium, whereby a first yellow fever virus population is obtained and further recovered;
  d) amplifying the recovered first yellow fever virus population obtained at the end of step c) 2 times or more on fresh Vero cells, whereby a second yellow fever virus population is obtained;
  e) cloning the second yellow fever virus population obtained in step d) by two or more successive plaque purifications on Vero cells whereby a plurality of yellow fever virus clones is obtained;
  f) amplifying separately each of the recovered yellow fever virus clones obtained at the end of step e) 2 times or more on fresh Vero cells, whereby a plurality of yellow fever virus strains is obtained; and
  g) selecting from the said plurality of yellow fever virus strains recovered in step f) one or more live-attenuated yellow fever virus strain comprising a nucleic acid comprising:
    i) a mutation in the codon for the amino acid at position 480 of the envelope protein (E) which results in an amino acid change from valine to leucine, or
    ii) a mutation in the codon for the amino acid at position 65 of the non-structural protein 2A (NS2a) which results in an amino acid change from methionine to valine. Such selection is easily conducted with sequencing methods well known in the art.

In some embodiments, step g) may comprise selecting one or more live-attenuated yellow fever virus strain comprising a nucleic acid comprising:
  i) a mutation in the codon for the amino acid at position 480 of the envelope protein (E) which results in an amino acid change from valine to leucine, and
  ii) a mutation in the codon for the amino acid at position 65 of the non-structural protein 2A (NS2a) which results in an amino acid change from methionine to valine.

In some embodiments, step g) may comprise selecting one or more live-attenuated yellow fever virus strain as described above comprising a nucleic acid further comprising a mutation in the codon for the amino acid at position 19 of the non-structural protein 4A (NS4a) which results in a codon change from AAA to AAG.

In some embodiments, step g) may comprise selecting one or more live-attenuated yellow fever virus strain as described above comprising a nucleic acid further comprising a mutation in the codon for the amino acid at position 145 of the envelope protein (E) which results in a codon change from GUA to GUU.

In some embodiments, step g) may comprise selecting one or more live-attenuated yellow fever virus strain comprising a nucleic acid comprising:
  i) a mutation in the codon for the amino acid at position 480 of the envelope protein (E) which results in an amino acid change from valine to leucine,
  ii) a mutation in the codon for the amino acid at position 65 of the non-structural protein 2A (NS2a) which results in an amino acid change from methionine to valine,
  iii) a mutation in the codon for the amino acid at position 19 of the non-structural protein 4A (NS4a) which results in a codon change from AAA to AAG, and/or
  iv) a mutation in the codon for the amino acid at position 145 of the envelope protein (E) which results in a codon change from GUA to GUU.

In an embodiment, the parent live-attenuated yellow fever virus strain of step a) is a yellow fever 17D substrain, such as a yellow fever 17D-204 substrain.

In practice, Vero cells are available in cell collections, such as ATCC. The methods suitable to grow Vero cells in in vitro cell culture, including methods using serum-free medium, are well known to the man skilled in the art (Kolell K. et al. 2007). In an embodiment, the Vero cells are adapted to grow on serum-free medium before any viral culture.

In some embodiments, the culture medium used to grow the Vero cells is serum-free, and is optionally free of any human or animal-derived substance.

Within the scope of the present invention, the expression "human or animal-derived substance" refers to a substance, such as a protein, a lipid, a glycoprotein, a lipoprotein, glycolipid, a monosaccharide or a polysaccharide, originating from a human or non-human animal, e.g. a growth factor, a hormone, that is obtained from, e.g. extracted from, a human or non-human animal. Recombinant molecules are not considered as human or animal-derived substance. Such serum-free media and/or media free of any human or animal-derived substance are easily available on provider catalogues (for instance THERMOFISHER SCIENTIFIC® catalogue).

In some embodiments, the culture medium used to grow the Vero cells is also devoid of antibiotics.

In some embodiments, the culture medium used to grow the Vero cells may comprise one or more extract originating from a bacterium, yeast and/or plant.

In some embodiments, the genome of the parent live-attenuated yellow fever virus strain not adapted to grow on Vero cells may be in the form of a cDNA encoding the genomic RNA.

In certain embodiments, the cDNA is carried by a suitable vector, such as e.g. a plasmid.

In some other aspect, the invention relates to a vector comprising a nucleic acid comprising the RNA sequence SEQ ID NO. 1, SEQ ID NO. 2, SEQ ID NO. 3, SEQ ID NO. 4, or SEQ ID NO. 5, in which the mutation(s) described herein is/are present.

In some other aspect, the invention relates to a vector comprising a nucleic acid comprising the cDNA sequence corresponding to sequence SEQ ID NO. 1, SEQ ID NO. 2, SEQ ID NO. 3, SEQ ID NO. 4, or SEQ ID NO. 5, in which mutations corresponding to the mutation(s) described herein is/are present.

In a further aspect, the live-attenuated yellow fever virus strain according to the present invention is obtained by mutation of the genomic sequence of a yellow fever virus, in order to introduce in that said genomic sequence the mutations described in the present invention. In some embodiments, the genomic sequence of a yellow fever 17D-substrain may be mutated in order to introduce in that said genomic sequence the mutations described in the present invention. In some embodiments, the nucleic acid comprising the RNA sequence of SEQ ID NO. 1, SEQ ID NO. 2, SEQ ID NO. 3, SEQ ID NO. 4, or SEQ ID NO. 5, or the corresponding cDNA sequence, may be mutated in order to introduce mutations described in the present invention. The mutations may be introduced in the genomic sequence by site-directed mutagenesis via methods well known by the skilled person, including use of any suitable gene-editing technology. The genomic sequence in which the mutations described in the present invention are introduced may be a cDNA encoding the genomic RNA of the yellow fever virus, such as, a cDNA encoding the genomic RNA of a yellow fever 17D-substrain, for instance a cDNA encoding SEQ ID NO. 1, SEQ ID NO. 2, SEQ ID NO. 3, SEQ ID NO. 4, or SEQ ID NO. 5. In some embodiments, the cDNA is carried by a suitable plasmid. The mutations described in the present invention that may be introduced in the genomic sequence of a yellow fever virus are selected from a mutation of the nucleotide at position 2411, position 3701 or position 6496 of the genomic sequence; or any combination thereof. In some embodiments, these mutations may comprise the nucleotide G (guanosine) at position 2411 of the genomic sequence being replaced by nucleotide U (uridine), the nucleotide A (adenosine) at position 3701 of the genomic sequence being replaced by nucleotide G (guanosine); or the nucleotide A (adenosine) at position 6496 of the genomic sequence being replaced by nucleotide G (guanosine), or any combination thereof. In some embodiments, a further mutation is introduced located at position 1408 of the genomic sequence. In some embodiments, this further mutation is the nucleotide A (adenine) at position 1408 of the genomic sequence being replaced by nucleotide U (uridine). In some embodiments, other mutations may be introduced in the genomic sequence of the yellow fever virus, with the proviso that no nucleotide is mutated in a way that results into a reversion to the Asibi genotype. In another aspect, the mutations described in the present invention that may be introduced in the genomic sequence of a yellow fever virus are selected from a mutation in the codon for the amino acid at position 480 of the envelope protein (E) which results in an amino acid change from valine to leucine, a mutation in the codon for the amino acid at position 65 of the non-structural protein 2A (NS2a) which results in an amino acid change from methionine to valine, or a mutation in the codon for the amino acid at position 19 of the non-structural protein 4A (NS4a) which results in a codon change from AAA to AAG, or any combination thereof. In some embodiments, a further mutation is introduced in the codon for the amino acid at position 145 of the envelope protein (E) which results in a codon change from GUA to GUU. In some embodiments, other mutations may be introduced in the genomic sequence of the yellow fever virus, with the proviso that no nucleotide is mutated in a way that results into a reversion to the Asibi genotype. In particular, the mutations described in the present invention that may be introduced in the genomic sequence of a yellow fever virus are a mutation in the codon for the amino acid at position 480 of the envelope protein (E) which results in an amino acid change from valine to leucine and a mutation in the codon for the amino acid at position 65 of the non-structural protein 2A (NS2a) which results in an amino acid change from methionine to valine.

In a further aspect, the invention also relates to a live-attenuated yellow fever virus strain obtainable by a method according to the present invention.

It is also disclosed herein a live-attenuated yellow fever virus strain obtained by a method according to the present invention.

Miscellaneous Methods and Uses

The instant invention also relates to a method for immunizing an individual in need thereof against an infection by an YFV comprising the administration to the said individual of a vaccine composition according to the present invention.

Within the scope of the present invention, the expression "individual in need thereof" is intended to refer to an individual at risk of being infected by an YFV.

A further aspect of the invention also relates to the use of a live-attenuated YFV strain according to the present invention for the preparation of a vaccine. In some embodiments, the invention also relates to the use of a live-attenuated YFV strain according to the present invention as a pMSL, as a MSL or as a WSL. In particular, the invention also relates to the use of a live-attenuated YFV strain according to the present invention as a pMSL, as a MSL or as a WSL, in a vaccine preparation process.

In another aspect, the invention relates to a live-attenuated YFV strain according to the present invention for use in the preparation of a vaccine.

A still further aspect of the invention also relates to a vaccine composition according to the present invention for use in preventing an infection by an YFV.

In some embodiments, the present invention relates to a method for preventing an infection by a YFV in an individual comprising the administration to the said individual of an efficient amount of a live-attenuated YFV, an immunogenic composition, a pharmaceutical composition or a vaccine composition according to the present invention.

In some embodiments, the present invention relates to a method for generating neutralizing antibodies against a yellow fever virus in an individual comprising the administration to the said individual of an efficient amount of a live-attenuated YFV, an immunogenic composition, a pharmaceutical composition or a vaccine composition according to the present invention.

In some embodiments, the present invention relates to the use of a live-attenuated virus according to the present invention for preparing a medicament for preventing an infection by an YFV.

In some embodiments, the present invention relates to a live-attenuated virus according to the present invention for use in preventing an YFV infection.

In some embodiments, the present invention relates to the use of an immunogenic composition according to the present invention, for preparing a medicament for preventing an infection by a YFV.

In some embodiments, the present invention relates to the use of an immunogenic composition according to the present invention, for preparing a vaccine composition for preventing an infection by a YFV.

In some embodiments, the present invention relates to an immunogenic composition according to the present invention, for use in preventing an infection by an YFV.

The vaccine composition and the immunogenic composition according to the present invention may be administered to an individual in need thereof by any suitable route of administration.

The immunogenic composition or the vaccine, according to the invention can be administered via any suitable route, such as by mucosal administration (e.g. intranasal or sublingual), parenteral administration (e.g. intramuscular, subcutaneous, transcutaneous, or intradermal route), or oral administration. As appreciated by the man skilled in the art, a vaccine of the present invention is suitably formulated to be compatible with the intended route of administration. In exemplary embodiments, the composition of the invention is administered intramuscularly or subcutaneously.

A vaccine according to the present invention may be administered in multiple doses. For example, a vaccine according to the present invention may be administered in one, two or three doses. In an embodiment the vaccine according to the present invention is administered in a single dose.

The vaccine according to the present invention can be administered in amounts that can readily be determined by persons of ordinary skill in this art. In some embodiments, the vaccine dose is between 4 and 6 $\log_{10}$ $CCID_{50}$.

EXAMPLES

Example 1: Preparation of Live-Attenuated YFV Strains by Adaptation on Vero Cells (Premaster Seed Lots (pMSLs))

1.1/Choice of the Method—Principles

The overall strategy for the pre Master Seed Lots (pMSLs) is displayed in FIG. 1.

Both YF-VAX® and Stamaril® vaccines were developed from un-cloned YF17D-204 strain preparations and contain heterologous populations of virus as visualized by plaque size phenotype. In addition, both vaccines were produced on eggs.

In order to generate homogeneous, well-defined, virus strains adapted to grow on Vero cells, and to ensure sterility and absence of adventitious agents in the final pMSLs:

(1) the viral genomic RNA of YF-VAX® and Stamaril® viruses were purified;
(2) and then transfected into Vero cells to recover yellow fever viruses that were then amplified twice on Vero cells in order to adapt the viruses for growing on this cell substrate;
(3) the viruses were then cloned by two plaque purification cycles. For that purpose, the viral preparation was diluted for infection of Vero cells and grown under a semi-solid overlay in order to get well separated virus plaques. For each transfection, 2 individual plaques, corresponding each to a single virus population were picked through the overlay, diluted and used for a second cycle of plaque-purification leading to the generation of viral clones;
(4) these clones were then amplified to obtain a sufficient viral stock to constitute a pMSL.

All media and solutions used for the pMSL production were animal- and human-component free.

1.2/Methods 1.2.1/In Vitro Transcription from the YF-VAX® Genomic cDNA

In vitro transcription of the genomic cDNA of YFV from the YF-VAX® (plasmid pJSY2374.5, as disclosed in WO 2014/016360) was performed with mMessage mMachine™ SP6 Kit (AMBION®, reference AM1340) according to the supplier's recommendations. From the plasmid pJSY2374.5, 2 in vitro transcriptions were performed in parallel.

Briefly, after thawing at room temperature, 10 µg of plasmid were linearized by digestion for 2 hours at 37±2° C. with restriction enzyme NruI (30 U/10 µg). The enzyme was then inactivated by incubating at 65° C. for 20 minutes. The linearization of the plasmid was verified by electrophoresis on a 0.5% agarose gel. A 40 µL reaction mixture comprising the reaction buffer of the kit, the ribonucleotides (ATP, CTP, UTP and a mixture of GTP and 7-methyl-GTP), the enzyme and 1 µg of plasmid was prepared. The resulting mixture was incubated for 2 hours at 37±2° C.

1.2.2/RNA Purification a) From the Stamaril® Vaccine Working Seed Lot

Two purifications of the viral RNA were performed in parallel.

Four vials of working seed lot of the Stamaril® vaccine (lot #FA238667, infectious titer 6.38 $\log_{10}$ PFU/vial) were each suspended in 200 µl of lysis buffer of the RNeasy® kit (QIAGEN®) and then pooled. The RNA was then purified by two series of extraction with a phenol/chloroform/isoamyl alcohol (125:24:1; pH 4.5).

2 mL Phase Lock Gel Heavy tubes (SPRIME®) were centrifuged for 30 seconds at 11,000×g. 750 µL of RNA/lysis buffer mixture were introduced into each tube. An equal volume (750 µl) of phenol/chloroform/IAA solution was then added to each tube. After vigorously mixing the organic and aqueous phases to form a homogeneous transient suspension, the tubes were centrifuged at 11,000×g for 5 minutes to separate the phases. The upper phase (aqueous phase) was then recovered. The operation was renewed on new Phase Lock Gel 2 mL tubes. Then the operation was again performed with a mixture of chloroform and Isoamyl alcohol (24:1) to remove all traces of phenol. The RNA was then concentrated and cleaned of any trace of organic solvent by purification on silica column with RNeasy® kit (QIAGEN®) following the recommendations of the provider. The purified RNA was then eluted in nuclease-free water.

b) From the In Vitro Transcription of the YF-VAX® Genomic cDNA

The plasmidic DNA contaminating the RNA obtained by in vitro transcription (see above) was eliminated by 4 U of DNase for 15 minutes at 37±2° C. The SP6 polymerase was then inactivated by incubation for 10 minutes at 70° C.

The RNA obtained by in vitro transcription was mixed with 60 µl of RNase-free water and 350 µl of lysis buffer from the RNeasy® kit (QIAGEN®). The RNA was then purified by two series of extraction with a phenol/chloroform/isoamyl alcohol (125:24:1; pH 4.5). For this, Phase Lock Gel Heavy 1.5 mL tubes were centrifuged for 30 seconds at 11,000×g. 750 µL of RNA/lysis buffer mixture was introduced into each tube. An equal volume (750 µl) of phenol/chloroform/isoamyl alcohol solution was then added to each tube. After vigorously mixing the organic and aqueous phases to form a homogeneous transient suspension, the tubes were centrifuged at 11,000×g for 5 minutes in order to separate the phases. The upper phase (aqueous phase) was then recovered. The operation was renewed on new Phase Lock Gel 1.5 mL tubes. Then the operation was again performed with a mixture of chloroform and isoamyl alcohol (24:1) to remove all traces of phenol. The RNA was then purified on silica column with RNeasy® kit (QIAGEN®) following the supplier's recommendations. The purified RNA was then eluted with nuclease-free water.

1.2.3/Transfection

Two transfections were conducted in parallel for each RNA purification.

a) Preparation of the RNA/Lipofectamine™ Mixture 10 or 15 μL of Lipofectamine™ 2000 CD (LIFE TECHNOLOGIES®)—were mixed with 1 mL of OptiPro SFM medium (LIFE TECHNOLOGIES®) and incubated for 5 minutes at room temperature. About 10 $\log_{10}$ Geq (genome equivalent titer determined by YF-NS5 qRT-PCR as described in Mantel et al. (2008)) of purified RNA were then added. These mixtures were incubated for 10 minutes at room temperature.

b) Vero Cells Preparation

Before transfection, serum-free Vero cells from Sanofi Pasteur's GMP bank previously seeded in 6-well plates ($9.10^5$ cells in 3 mL of VP-SFM (THERMOFISHER SCIENTIFIC) per well) were rinsed with 2 mL per well of OptiPro SFM medium.

c) Transfection Reaction

In the 6-well plate, after removal of the rinsing medium from the cells, the mixtures of transfection containing the RNA were deposited in two wells (1 mL/well) for each preparation. A well was brought into contact with an OptiPro SFM/Lipofectamine™ containing no RNA and the last well was kept as a cell control in OptiPro SFM medium alone. Two plates were prepared in parallel, one with the mixtures containing 10 μl of Lipofectamine™ and one with the mixtures containing 15 μl of Lipofectamine™. The mixture containing Lipofectamine™ and the RNA was left in contact with the Vero cells for 4 hours at 37±2° C. at 5±2% $CO_2$ and then 2 mL of preheated VP-SFM medium were added to each well. The 6-well plates were incubated at 37±2° C.; 5±2% $CO_2$ for 16 h. The medium was then renewed and the plates re-incubated at 37±2° C., 5±2% $CO_2$. Transfection supernatants were collected when the cytopathic effect (cell lysis) was visible and when the genomic titer determined by YF-NS5 qRT-PCR from the culture supernatant (as described in Mantel et al. (2008)) was greater than 8.0 $\log_{10}$ Geq/mL. Replacement of the culture medium by fresh medium was performed on D5 and D8 if culture times needed to allow harvest were greater than these times. The harvested supernatants were divided into aliquots.

1.2.4/Amplification of the virus a) Amplification No 1 (Viral Passage No 2)

Two days before virus amplification no 1, $2.10^5$ Vero cells were seeded in 25 $cm^2$ flasks containing 5 mL of VP-SFM medium. Then the viral suspensions resulting from the transfection were diluted in VP-SFM medium in order to obtain a multiplicity of genome (m.o.g) of 2 (i.e. 2 Geq per cell, estimated from the RNA concentration obtained by qRT-PCR). The culture medium of the Vero cells previously seeded was eliminated and the cells were brought into contact with 1 mL of the diluted viral suspension or 1 mL of VP-SFM medium alone (cell control). The flasks were incubated for 2h at 37±2° C.; 5±2% $CO_2$. The viral inoculum was then removed and replaced with 10 mL of VP-SFM medium and the cells were incubated at 37±2° C.; 5±2% $CO_2$ for 2 days. The culture medium was then renewed by new VP-SFM medium preheated to 37±2° C. and the flasks re-incubated at 37±2° C.; 5±2% $CO_2$ for 2 to 3 days. After a total of 4 to 5 days of incubation, the culture supernatant containing the virus was recovered. The viral suspension was clarified by centrifugation for 10 minutes at 1200 rpm at 4° C. and then distributed in aliquots. 140 μl of this viral suspension were used to extract total RNA with a QiaAmp viral mini kit (QIAGEN®; according to the supplier's protocol), and to quantify the viral RNA by YF-NS5 qRT-PCR (as described in Mantel et al. (2008)).

One or more aliquots, depending on the viral RNA titer, were stored to make the second amplification step if it was performed the same day, the others were frozen at ≤−70° C. in the presence of 10% final sorbitol.

b) Amplification No 2 (Viral Passage No 3)

Two days before virus amplification no 2, $5.10^5$ Vero cells were seeded in 75 $cm^2$ flasks containing 20 mL of VP-SFM medium. Then the viral suspension from the first amplification was diluted in VP-SFM medium so as to infect Vero cells at a rate of m.o.g of 2 (i.e. Geq per cell, estimated from the concentration of RNA obtained by qRT-PCR).

The other steps of the amplification no 2 were performed as detailed for the amplification no 1 (see section a) above).

c) Viral Cloning—Plate Purification (Viral Passages 4 and 5)

Two 6-well plates were required per viral suspension obtained after transfection and amplification.

An aliquot of viral suspension obtained after amplification no 2 was diluted so as to obtain a suspension at about 2.0 $\log_{10}$ PFU/mL and a suspension at 1.7 $\log_{10}$ PFU/mL. Vero cells previously seeded in 6-well plates ($9.10^5$ cells in 3 mL of VP-SFM per well) were observed for verifying the integrity of the cells and the absence of contamination, then the culture medium was removed. For each dilution, 5 wells of a plate were infected by 500 μL of the diluted virus in each well (2.0 $\log_{10}$ PFU/mL or 1.7 $\log_{10}$ PFU/mL dilutions) and, a cell control well contained 500 μL of VP-SFM only. The plates were incubated for 2 hours at 37±2° C.; 5±2% $CO_2$. Then the inoculum was removed and replaced by 4 mL of an overlay mixture, i.e. a solution of VP-SFM 2× preheated to 42° C. and mixed extemporaneously volume to volume with a 2% agarose solution. After solidification of the overlay mixture, the plates were incubated in the reverse position (lid downward) for 3 to 6 days at 37±2° C.; 5±2% $CO_2$. The plates were observed every day. As soon as a cytopathic effect appeared a second overlay mixture which was identical to the first one but further contains 0.008% neutral red was added to each well (2 mL), and the plates were incubated in the reverse position for 1 to 2 days at 37±2° C.; 5±2% $CO_2$.

Infection of a cell with a viral particle (clone) remained in these conditions limited to immediately surrounding cells and caused local lysis, creating a white spot (lysis plaque) rich in viruses over an otherwise red-colored cellular monolayer. For each amplified viral dilution, two clones were recovered through the cover medium using a micropipette and a 1000 μL cone. The viral clone thus obtained was suspended in 1 mL of VP-SFM medium and then mixed vigorously.

Each of these suspensions was diluted in cascade steps from 1:2 to 1:200,000 to perform a second series of plate purification. At the end of this second cloning run, two clones per plate were again harvested. Sixteen clones maximum per lineage were obtained, i.e. 16 clones from Stamaril® parent strain and 16 clones from YF-VAX® parent strain.

d) Amplification No 3 (Viral Passage No 6)

For each clone (up to 32), the viral suspension obtained by re-suspension of the viral matter contained in agarose was diluted ¼ or ½ (depending on the size of the collected plaque) in VP-SFM.

The amplification no 3 was performed according to the same protocol as amplification no 1 (see section a) above).

The amplified virus was harvested when a cytopathic effect was visible and the genomic titer in qRT-PCR was above 8.0 $\log_{10}$ Geq/mL.

After a total of 4 to 5 days of incubation, the culture supernatant containing the virus was recovered and divided into aliquots. 140 µl of this viral suspension were used to extract the total RNA with QiaAmp viral mini kit (QIAGEN®), according to the protocol of the supplier, and to quantify RNA by YF-NS5 qRT-PCR (as described in Mantel et al. (2008)). One or more aliquots, depending on the viral RNA titer, were retained to carry out the next step amplification, the others were frozen at ≤−70° C. in the presence of 10% final sorbitol.

e) Amplification No 4 (Viral Passage No 7)

The viral suspension resulting from the amplification no 3 (see section d) above) was diluted in VP-SFM medium so as to infect Vero cells previously seeded at a rate of m.o.g of 2 and further processed according to the same protocol as the amplification no 2 (see section b) above).

The amplified virus was harvested when a cytopathic effect was visible and the genomic titer in qRT-PCR was above 8.0 $\log_{10}$ Geq/mL. After a total of 4 to 5 days of incubation, the supernatant was recovered, the viral suspension was clarified by centrifugation for 10 minutes at 1200 rpm at 4° C., and then divided into frozen aliquots at ≤−70° C. in the presence of 10% final sorbitol.

The viral suspension thus obtained was used to carry out infectious titration and sequencing of the viral genome.

From these data three strains from each lineage (i.e. the three TV2212, TV2232 and TV2241 strains from Stamaril® parent strain and the three TV3111, TV3112 and TV4221 strains from YF-VAX® parent strain) were selected according to the following criteria: infectious titer ≥6 $\log_{10}$ $CCID_{50}$/mL and a genomic sequence exhibiting no reversion to the Asibi original strain sequence.

Viral suspension infectious titration was performed using $CCID_{50}$ method on Vero cells. Briefly, the viral suspensions were serially 4-fold diluted in IMDM (THERMOFISHER SCIENTIFIC)+4% FCS starting from −4.6 log 10 to −8 log 10 in a 96-deep well plate. A control virus (Stamaril® virus amplified once on Vero cells, batch MLE-JPO-000089) was included in each test as a positive reference. One hundred microliters of each virus dilution were added into 10 wells containing Vero cells seeded in flat bottom 96-well plates three days before the assay (8000 cells/well). After 4 days of incubation at +37° C., 5% $CO_2$, supernatants were discarded and cells were fixed for 15 minutes at −20±3° C. with 150 µL acetone 85% then saturated with 2.5% milk PBS-Tween buffer solution before immunostaining with the pan-flavivirus E-specific 4G2 mouse monoclonal antibody (RD BIOTECH®, lot #130726-4G2) at 2 µg/mL (dilution ½,000). Infected foci stained with 4G2 antibody were then revealed after incubation with a Goat Anti-Mouse IgG alkaline-phosphatase conjugated antibody (CLINISCIENCES® SA, ref #1030-04, lot #A7013-Z145) diluted ¹⁄1000 and then with an alkaline-phosphatase substrate (BCIP/NBT, SIGMA-ALDRICH®, ref #B5655, lot #SLBN0689V and levamisole, SIGMA-ALDRICH®, ref #L9756, lot #091M1227V).

Positive wells, i.e. wells containing at least one plaque stained in black were counted and the final titer was calculated using the Least Square regression method.

f) Amplification No 5 (Viral Passage No 8)—Premaster Candidate (pMSL)

The viral suspension from each of the 6 strains selected from the amplification no 4 (see section e) above) was diluted in VP-SFM medium so as to infect Vero cells at a m.o.i of 0.01.

Two days before virus amplification n°5, $12.10^6$ Vero cells were seeded in 175 $cm^2$ flasks containing 30 mL of VP-SFM medium. As previously performed, the culture medium was removed and replaced with 12 mL of diluted virus suspension or VP-SFM alone (control cells). The flasks were incubated during 2h at 37±2° C.; 5±2% $CO_2$. The viral inoculum was then removed and replaced with 50 mL of VP-SFM medium. The flasks were incubated for 2 days at 37±2° C.; 5±2% $CO_2$. The culture medium was then renewed with fresh VP-SFM medium preheated to 37±2° C. and the flasks were re-incubated at 37±2° C.; 5±2% $CO_2$ for 1 to 3 days. The amplified virus was harvested when a cytopathic effect was visible and the genomic titer in qRT-PCR was above 8.0 $\log_{10}$ Geq/mL.

After a total of 3 to 5 days of incubation, the supernatant was recovered, the viral suspension was clarified by centrifugation for 10 minutes at 1200 rpm at 4° C., then distributed in aliquots that were frozen at ≤−70° C. in the presence of 10% final sorbitol. The amplified viruses obtained from the 6 selected strains constituted the 6 candidate pMSLs.

Example 2: Neurovirulence of the Candidates in a Mouse Model 2.1/Neurovirulence of the pMSL Candidates in a Mouse Model The neurovirulence of the vYF (Vero cells adapted-Yellow fever virus) pre-master seed lot (pMSL) candidates was assessed through determination of Mouse Lethal Dose 50% ($MLD_{50}$) as described in WHO TRS 872, annex 2 (1998).

For the study of neurovirulence of the pMSL candidates, groups of 8 female OF1 mice (4-weeks old at inoculation), were injected by the intra-cerebral route with 30 µl of 5 to 7 virus dilutions in 0.4% NaCl 2.5% human serum albumin (HSA) buffer. Four vYF pMSL candidates TV2212, TV3111, TV3112 and TV4221 were evaluated for their neurovirulence and compared to Stamaril® and YF-VAX® reference vaccines. The mice were monitored for 21 days and the number of surviving mice was recorded at day 21. Three independent experiments were performed with a random distribution of the samples. Injected quantities were checked by $CCID_{50}$ back-titration on the day of inoculation for each experiment.

The clinical monitoring was performed daily to record each day the survival rate. The $MLD_{50}$ were calculated as the dose inducing 50% of surviving mice using the last square regression and expressed in $\log_{10}$ $MLD_{50}$/mL. The $MLD_{50}$ of each strain was determined as a pondered mean of the 3 determinations and 95% confidence intervals, except for TV3111 and TV3112 for which no $MLD_{50}$ could be calculated, as 100% of surviving mice were recorded for groups administered with TV3111 and TV3112 strains even with the highest dose (30 µl of 0.7 $\log_{10}$ dilution).

The results are presented in Table 2 below.

TABLE 2

Characterisation of the vYF strains at the pMSL stage, in a mouse neurovirulence test ($MLD_{50}$ test)

| YFV strain | $\log_{10} CCID_{50}$/mL | $\log_{10} MLD_{50}$/mL |
|---|---|---|
| Stamaril ® | 6.3 | 6.0 |
| TV2212 | 6.8 | 6.7 |
| YF-VAX ® | 7.5 | 4.7 |
| TV3111 | 7.2 | <2.2 |

TABLE 2-continued

Characterisation of the vYF strains at the pMSL stage, in a mouse neurovirulence test (MLD$_{50}$ test)

| YFV strain | log$_{10}$CCID$_{50}$/mL | log$_{10}$MLD$_{50}$/mL |
|---|---|---|
| TV3112 | 7.2 | <2.2 |
| TV4221 | 7.9 | 4.8 |

With respect to vYF strain TV2212 issued from the Stamaril® lineage, it exhibited similar neurovirulence as compared to Stamaril® reference vaccine.

vYF strain TV4221 issued from the YF-VAX® lineage exhibited similar neurovirulence as compared to YF-VAX® reference vaccine. Finally, vYF strains TV3111 and TV3112, both issued from the YF-VAX® lineage exhibited no neurovirulence effect as compared to YF-VAX® reference vaccine. No MLD$_{50}$ titer can be calculated for these 2 vYF strains (at least <2.2 log$_{10}$ MLD$_{50}$/mL).

As a result, 2 vYF strains TV2212 and TV4221 presented similar neurovirulence profile and MLD$_{50}$ titers than their respective parent references Stamaril® and YF-VAX®. Two other vYF strains, TV3111 and TV3112 both issued from the YF-VAX® lineage, presented a noticeable attenuation of neurovirulence compared to their YF-VAX® parent strain and their MLD$_{50}$ titers could not be assessed.

2.2./Neurovirulence of the TV3112 Strain MSL and WSL in a Mouse Model 2.2.1/TV3112 Strain MSL and WSL All media and solutions used for the MSL and WSL production were animal- and human-component free.

After Vero cell amplification in static conditions, the cells were seeded in a bioreactor. After 3 days of cell growth in the bioreactor, the medium was changed from cell growth medium to virus production medium. The virus was inoculated by adding the seed lot (TV3112 pMSL to produce TV3112 MSL or TV3112 MSL to produce TV3112 WSL) in the bioreactor. After 2 days of virus multiplication, the virus production medium was discarded and replaced by the same volume of fresh virus production medium. 4 days after virus inoculation, the content of the bioreactor was harvested, clarified, stabilized, filled and stored frozen.

2.2.2/Neurovirulence of the TV3112 Strain MSL and WSL

The same protocol as described in Example 2, sub section 2.1 above was used.

TABLE 3

Characterisation of the TV3112 strain at the MSL and WSL stages, in a mouse virulence test (MLD$_{50}$ test)

| YFV strain | log$_{10}$CCID$_{50}$/mL | log$_{50}$MLD$_{50}$/mL |
|---|---|---|
| TV3112 MSL | 7.0 | <2.2 |
| TV3112 WSL | 8.1 | <2.2 |

As for TV3112 pMSL, TV3112 MSL and TV3112 WSL exhibited no neurovirulence effect. No MLD$_{50}$ titer can be calculated for TV3112 MSL and TV3112 WSL (at least <2.2 log$_{10}$ MLD$_{50}$/mL).

TV3112 MSL and TV3112 WSL presented a noticeable attenuation of neurovirulence compared to their YF-VAX® parent strain and their MLD$_{50}$ titers could not be assessed.

Example 3: Viscerotropism and Neurotropism of the vYF Strain Candidates in a Mouse Model Viscerotropism and neurotropism of the 6 vYF (Vero cells adapted-Yellow fever virus) pre-master seed lot (pMSL) candidates were assessed in assays based on inoculation to type I IFN receptors deficient mice that were developed to allow the discrimination between pathogenic and attenuated vaccine strains (Meier et al., 2009; Erickson and Pfeiffer, 2015). The A129 immuno-deficient mice KO for type I IFN receptors are described to mimic the wild-type YF virus infection in primates and humans (Meier et al., 2009). Therefore, such a mouse model appears suitable to study viscerotropic disease caused by non-attenuated yellow fever viruses.

3.1/Methods 3.1.1/Group Definition

Fifteen groups (group A to O) of six 4-8 week old female A129 mice were administered with 4 log$_{10}$ CCID$_{CCID50}$/dose of each of the 6 pMSL candidates or of the Stamaril® reference vaccine as described in Table 4 below (no adjuvant; subcutaneous administration route; 200 µl at D0).

TABLE 4

Group definition

| Group | Mice number per group | Product under test Name | Active substance Dose |
|---|---|---|---|
| A | 6 | PBS 1X | — |
| B | 6 | Stamaril® | 4 log PFU |
| C | 6 | Stamaril® | 4 log PFU |
| D | 6 | TV2212 | 4 log$_{10}$ CCID$_{50}$ |
| E | 6 | TV2212 | 4 log$_{10}$ CCID$_{50}$ |
| F | 6 | TV2232 | 4 log$_{10}$ CCID$_{50}$ |
| G | 6 | TV2232 | 4 log$_{10}$ CCID$_{50}$ |
| H | 6 | TV2241 | 4 log$_{10}$ CCID$_{50}$ |
| I | 6 | TV2241 | 4 log$_{10}$ CCID$_{50}$ |
| J | 6 | TV3111 | 4 log$_{10}$ CCID$_{50}$ |
| K | 6 | TV3111 | 4 log$_{10}$ CCID$_{50}$ |
| L | 6 | TV3112 | 4 log$_{10}$ CCID$_{50}$ |
| M | 6 | TV3112 | 4 log$_{10}$ CCID$_{50}$ |
| N | 6 | TV4221 | 4 log$_{10}$ CCID$_{50}$ |
| O | 6 | TV4221 | 4 log$_{10}$ CCID$_{50}$ |

3.1.2/Study Schedule

The study schedule is described in FIG. 2.

The 6 mice of groups C,E,G,I,K,M,O were euthanized and their organs sampled at D6 and the 6 mice of groups B,D,F,H,J,L,N were euthanized and their organs sampled at D11. Intermediate blood sampling was collected in groups A, B, D, F, H, J, L and N at D4. For the PBS control, only 6 mice were included and sampled at D11 (group A).

3.1.3/Mice Clinical Observations and Scoring

Animals were observed daily during 11 days post-inoculation according to the scoring grid described in Table 5 below. Body temperature was monitored and recorded every day from D3 to the end of the experiment at D11.

TABLE 5

Scoring table

| Parameters | Description | Score |
|---|---|---|
| General aspect (GA) | Normal | 0 |
| | Fur/Spiked | 1 |
| | Arched back | 2 |
| | shiver | 3 |
| Neurological signs (NS) | Normal | 0 |
| | On tiptoe | 1 |
| | Motor complication | 2 |
| | Convulsion | 3 |

TABLE 5-continued

Scoring table

| Parameters | Description | Score |
|---|---|---|
| Reaction to Stimuli (RS) | Normal | 0 |
| | Stationary | 1 |
| | Reduced | 2 |
| | Excessive/Prostration | 3 |
| | No reaction | 4 |
| Breathing (B) | Normal | 0 |
| | Speed or Irregular | 1 |
| | Respiratory distress syndrome | 2 |

During the course of the experiment, animals were euthanized if any of the following events occur:
Signs of suffering (cachexia, weakening, difficulty to move or to eat)
Compound toxicity (hunching, convulsions)
General Aspect score=3+Reaction to Stimuli=3
Body weight loss >20%
Any animal found dead was necropsied.

3.1.4/Biological Sampling a) On D4, intermediate blood samples were taken under anaesthesia from the submandibular vein. Around 200 µL of blood were collected in vials containing clot activator and serum separator (BD Microtainer SST).

b) On Day 6 and D11, blood samples were taken after exsanguination by carotid section from all the animals under anaesthesia. Around 1 mL of blood was collected in vials containing clot activator and serum separator (BD Vacutainer SST).

c) Organ collections were performed under sterile conditions. Instruments used for the animal's dissection were previously rinsed with RNaseZap™ decontamination solution. All the organs listed below were sampled for all mice as soon as possible after the exsanguination followed by animal's euthanasia by cervical dislocation under anaesthesia: brain, liver and spleen.

For liver, two biopsy punches of 7 mm diameter dedicated to viral load detection were placed into vials containing 1 mL of RNAlater™ solution.

For brain and spleen, 2 half sections dedicated to viral load detection were placed into vials containing 1 mL of RNAlater™ solution.

3.1.7/Analytical Tests a) Viremia

Total genomic RNA was extracted from 140 µL of each individual serum sample with the Macherey Nagel Nucleo-Spin® 96 virus kit on Tecan Evoware automated RNA extraction workstation according to the manufacturer's instructions and eluted in two steps into a final volume of 140 µL of nuclease-free water.

Immediately after extraction, RNA quantification was performed by YF-NS5 qRT-PCR (as described in Mantel et al. (2008)). The qRT-PCR targets a conserved region of the YF NS5 gene to detect the presence of YF viral genome.

b) Viral Load in Organs

Biopsy punches were frozen at −80° C. in RNA Later™ solution. At thawing, each sample of organ was weighted.

Total RNA was extracted from the punches of organs using a combined Trizol™ (Invitrogen®)/RNeasy™ (Qiagen®) method as prescribed by the supplier's recommendations.

The presence of viral RNA in the purified RNA samples was then quantified using the YF-NS5 qRT-PCR assay as described in Mantel et al. (2008). The qRT-PCR targets a conserved region of the YF NS5 gene to detect the presence of YF viral genome.

Each qRT-PCR run included two non-template controls (negative qRT-PCR controls) and two positive controls based on CYD-3 viral suspension.

To validate a run, all negative controls had to be below the limit of detection (LOD) and the positive controls had to be included in the control charts.

Due to the dilutions factors and for a sample of 100 mg of organ, the limit of detection was calculated at 1 Geq/mg of organ.

3.2/Results 3.2.1/Clinical Signs

All the animals were observed daily post-inoculation according to the scoring grid described in Table 5 above: all mice from groups A to O were scored daily from day 3 up to day 6 and all mice from groups A, B, D, F, H, J, L and N were further scored daily up to day 11.

The mean scores were calculated for each criterion, i.e. General Aspect (GA), Reaction to Stimuli (RS), Neurological Signs (NS) and breath (B), from day 3 to day 11 for each group at each time-point As expected, for all the A129 mice injected with saline control (PBS, group A), no specific clinical score was recorded for any animal during all the monitoring period.

For all the A129 groups administered either with Stamaril® reference vaccine or with one of the vYF pMSL candidates, the clinical signs were mild with means score for each criterion inferior to 1.5 whatever the time-point and whatever the criterion (GA<1.5; RS, NS and B<1).

No specific clinical score was recorded for days 3, 4 and 5; then some scores 1/0/0/0 or 2/0/0/0 (GA/RS/NS/B) were recorded for few mice by days 6 and 7. At day 10 and 11, all the A129 mice administered either with Stamaril® reference vaccine or with one of the vYF pMSL candidates exhibited low scores (some mice with GA score=1 or 2 and RS, NS as well as B scores=1) except for one mouse administered with TV2232 (group F) presenting on day 10 some shivering phenotype, motor complication, prostration and respiratory distress (score 3/2/3/2) and that was euthanized for ethical reasons.

3.2.2/Weight Monitoring

All mice (groups A to O) were weighed on days 0, 3, 4, 5 and 6; on days 7, 10 and 11 all mice from the remaining groups (A, B, D, F, H, J, L and N) were weighed. The percentages of weight loss compared to day 0 were calculated for each individual mouse at each time-point.

After immunization with Stamaril® reference vaccine, a slight weight loss was observed during the 11 days monitoring period (mean of less of 5% weight loss at D11).

After immunization with vYF pMSL candidates coming from the Stamaril® lineage, as for the Stamaril control, no drastic loss of weight was observed except for one mouse immunized with clone TV2232 at day 10 that loose more than 20% of its weight. This mouse had to be euthanized for ethical reasons (see 3.2.1 above).

After immunization with vYF pMSL candidates coming from the YFVAX® lineage, TV3111, TV3112 and TV4221, stable weights were observed and recorded up to days 5 to 6 and a slight weight gain was observed up to the end of the monitoring period (mean of less of 5% weight gain at D11).

3.2.3/Viral Load in Sera and Organs a) In Sera—FIG. 3

Individual viremia as well as geometric mean titers (GMT) and standard deviations calculated for each group and time points are depicted in FIG. 3.

As expected, no viremia was detected at day 4 in A129 mice administered at day 0 with PBS (<LOD of 3 $\log_{10}$ Geq/mL) whereas geometric mean viremia titers between 4 and 5 $\log_{10}$ Geq/mL at day 4 and day 6 were detected in A129 mice administered with Stamaril® reference vaccine.

After immunization with the vYF pMSL candidates, no significant superiority of viremia was observed compared to the viremia induced after immunization with the Stamaril® control (all p-values >0.2 for TV2212, TV2232, TV2241, TV3111 and TV3112 whatever the time point) except for TV4221 coming from the YF-VAX® lineage that induced significantly higher viremia than the Stamaril® control at day 4 after injection (p-value=0.001).

b) In Liver—FIG. 4

Results are expressed in $\log_{10}$ Geq/mg of organ. Individual viral load as well as geometric means and standard deviations calculated for each group and time points are depicted in FIG. 4.

As expected, no liver viral load was detected at day 11 in A129 mice administered at day 0 with PBS (<LOD of 1 $\log_{10}$ Geq/mg) similarly no or low liver viral loads were detected in A129 mice administered with Stamaril® reference vaccine (GMT=0.8 at day 6, <LOD at day 11).

After immunization with the vYF pMSL candidates, no significant superiority of liver viral load was observed compared to the liver viral load induced after immunization with the Stamaril® control (all p-values >0.1 for TV2212, TV2232, TV2241, TV3111, TV3112 and TV4221 at day 6, no statistical analysis performed on day 11 due to the high number of non-responders <LOD).

c) In Brain—FIG. 5

Results are expressed in lop) Geq/mg of organ. Individual viral load as well as geometric mean titers and standard deviations calculated for each group and time points are depicted in FIG. 5.

As expected, no brain viral load was detected at day 11 in A129 mice administered at day 0 with PBS (<LOD of 1 $\log_{10}$ Geq/mg) whereas brain viral loads were detected in A129 mice administered with Stamaril® reference vaccine (GMT=0.6 at day 6, 3.7 at day 11).

After immunization with the vYF pMSL candidates, no significant superiority of brain viral load was observed compared to the brain viral load induced after immunization with the Stamaril® control (p-values >0.06 for TV2212 and TV2232). Additionally TV2241, TV3111, TV3112 and TV4221 induced significantly lower brain viral load at day 11 than Stamaril® control (p-values <0.003).

d) In Spleen—FIG. 6

Results are expressed in $\log_{10}$ Geq/mg of organ. Individual viral load as well as geometric mean titers and standard deviations calculated for each group and time points are depicted in FIG. 6.

As expected, no spleen viral load was detected at day 11 in A129 mice administered at day 0 with PBS (<LOD of 1 $\log_{10}$ Geq/mg) whereas spleen viral loads were detected in A129 mice administered with Stamaril® reference vaccine (GMT=4.1 at day 6, 2 at day 11).

After immunization with the vYF pMSL candidates, no significant superiority of spleen viral load was observed compared to the spleen viral load induced after immunization with the Stamaril® control (all p-values >0.09 for TV2212, TV2232, TV2241, TV3111, TV3112 and TV4221 whatever the time point).

3.2.4/Survival

In order to calculate survival rate for each group (for groups A, B, D, F, H, J, L and N), the number of surviving mice were recorded daily for 11 days after sub-cutaneous immunization with 4 $\log_{10}$ CCID$_{50}$/dose of Stamaril® or one of the 6 vYF pMSL candidates.

As depicted in the Kaplan Meir curves (FIG. 7), 100% (6 mice out of 6) of mice survived all along the study course when administered with either PBS buffer, Stamaril® or one of the five vYF strains TV2212, TV2241, TV3111, TV3112 and TV4221.

At the opposite, only 80% of mice survived in group F administered with the TV2232 strain coming from the Stamaril® lineage as on day 10 one mouse was euthanized for ethical reasons (see 3.2.1 above).

Example 4—Immunogenicity of the vYF Strain Candidates in a Hamster Model

The immunogenicity of the 6 vYF pMSL candidates in the Hamster model was evaluated and compared to the Stamaril® reference vaccine.

4.1/Methods 4.1.1/Group Definition

Fifteen 5-6 weeks old female Golden Syrian hamsters were included in each group and 2 doses, i.e. a low suboptimal dose of 2.5 $\log_{10}$ CCID$_{50}$/dose and a high dose of 5.5 $\log_{10}$ CCID$_{50}$/dose, were administered for each of the 6 pMSL candidates.

For the Stamaril® reference, only 10 hamsters per group were included for the 2 tested doses described above.

In total 200 female Golden Syrian Hamsters were randomly allocated to one of the 14 following groups (group A to N) described in Table 6 below (no adjuvant; subcutaneous administration route: 200 µl at D0 and D261.

TABLE 6

| Group definition | | | |
|---|---|---|---|
| | Hamster | Product under test | |
| | number | Active substance | |
| Group | per group | Name | Dose |
| A | 10 | Stamaril ® | 2.5 log PFU |
| B | 10 | | 5.5 log PFU |
| C | 15 | TV2212 | 2.5 $\log_{10}$ CCID$_{50}$ |
| D | 15 | | 5.5 $\log_{10}$ CCID$_{50}$ |
| E | 15 | TV2232 | 2.5 $\log_{10}$ CCID$_{50}$ |
| F | 15 | | 5.5 $\log_{10}$ CCID$_{50}$ |
| G | 15 | TV2241 | 2.5 $\log_{10}$ CCID$_{50}$ |
| H | 15 | | 5.5 $\log_{10}$ CCID$_{50}$ |
| I | 15 | TV3111 | 2.5 $\log_{10}$ CCID$_{50}$ |
| J | 15 | | 5.5 $\log_{10}$ CCID$_{50}$ |
| K | 15 | TV3112 | 2.5 $\log_{10}$ CCID$_{50}$ |
| L | 15 | | 5.5 $\log_{10}$ CCID$_{50}$ |
| M | 15 | TV4221 | 2.5 $\log_{10}$ CCID$_{50}$ |
| N | 15 | | 5.5 $\log_{10}$ CCID$_{50}$ |

4.1.2/Study Schedule

The study schedule is summarized in FIG. 8.

The planning of interventions and the intervention details are described in Table 7 below.

TABLE 7

Study Schedule

| Day | Group Number | Number of Animals | Interventions | Specific Characteristics |
|---|---|---|---|---|
| D0 | A to N | 200 | Bleeding<br>Immunization (first injection) | Chemical anaesthesia (IP route)<br>Intermediate blood sampling<br>Immunization SC route |
| D26 | A to N | 200 | Bleeding<br>Immunization (second injection) | Chemical anaesthesia (IP route)<br>Intermediate blood sampling<br>Immunization SC route |
| D41 | A to N | 200 | Bleeding | Chemical anaesthesia (IP route)<br>Intermediate blood sampling |
| D55 | A to N | 200 | Bleeding | Chemical anaesthesia (IP route)<br>Final blood sampling<br>Euthanasia |

4.1.3/Biological Sampling and Seroneutralization Assays a) Biological Sampling

Intermediate blood samples were taken under anaesthesia from the retro-orbital sinus (ROS) at D0, D26 and D41 from all the animals. The final blood sampling was taken under anaesthesia via an intracardiac puncture. The anaesthesia was performed by Imalgéne (150 mg/kg) and Rompun (10 mg/kg) administered under a volume of 200 µl by intraperitoneal route.

Blood was collected in vials containing clot activator and serum separator (BD Microtainer SST). After a night at +4° C. or 2h at 37° C., the blood was centrifugated at 2000×g during 10 minutes and the serum collected and stored at −20° C. until analysis.

b) Seroneutralization Assays

The functional neutralizing antibodies present in the serum of the immunized animals were titrated at D0, D26 and D41 from the first injection.

Briefly, the heat-inactivated sera were serially 2-fold diluted in IMDM+4% foetal calf serum (FCS) starting from 1:5. YF-17D Stamaril® virus grown on Vero cells was diluted in order to obtain 4000 µPFU/mL in IMDM and incubated 90 minutes with 2-fold diluted serum samples (v/v). The virus/serum mixture was then added to Vero cells in 96-well plates and incubated for 45+/−2 hours. After incubation, cells were fixed with 85% acetone before immunostaining. Plates were blocked with PBS+0.05% Tween 20+2.5% skim milk and incubated first with an anti-flavivirus monoclonal antibody 4G2, and second with a goat anti-mouse IgG HRP conjugate. Finally, plates were stained with the Trueblue™ chromogen. Plaques were counted with Viruscope reader from Microvision™

The final seroneutralizing antibody titer is calculated using the least square method and correspond to the inverse of the dilution demonstrating a neutralization of 50% of virus plaques. The LOD of the assay was 10, corresponding to the first reciprocal dilution in the final volume.

For calculation of the mean values per group, an arbitrary titer of 5 was assigned (half of the LOD) to all titers below 10.

4.2/Results—Seroneutralization

The neutralizing activity against the Yellow Fever 17D vaccine strain on Vero cells was monitored by seroneutralization assays in individual serum samples collected from all animals at baseline (D0), four weeks after one immunization (D26) and two weeks after two immunizations (D41). Geometric mean titers (GMT) as well as individual neutralizing titers and the 95% confidence interval (CI) are depicted in FIG. 9 and FIG. 10.

As expected, no or low neutralizing antibody titers (<40) were detected in naïve hamsters at baseline (D0) with group GMT <12, whatever the pMSL vYF candidates or the Stamaril® reference. A responder threshold was defined at 20.87 (1.32 $\log_{10}$) by the statistical analysis of all the individual data obtained at D0 (superior tolerance interval with proportion of 0.99 and risk alpha of 5%).

Regarding the response kinetics, one month after 1 immunization (D26; FIG. 9), a marked increased neutralizing response was observed for all the immunized groups with at least a 10- up to an 850-fold increase of neutralizing GMT compared to D0 baseline. Two weeks after the second immunization (D41; FIG. 10), neutralizing GMTs were further increased for all groups with a 0.8- to 7.5-fold increase of neutralizing GMT compared to D26.

The neutralizing antibody response induced by Stamaril® reference was significantly lower (p-values=0.007 and 0.023 at D26 and D41, respectively) for the 2.5 $\log_{10}$ $CCID_{50}$ dose (GMT 281 and 544 at D26 and D41, respectively) than for the 5.5 $\log_{10}$ $CCID_{50}$ dose (GMT 5061 and 11714 at D26 and D41, respectively). Of note, 100% of the hamsters from group administered with 5.5 $\log_{10}$ $CCID_{50}$ dose were defined as responder (>20.87 threshold) as soon as the first immunization (at D26) whereas only 60% and 70% of the hamsters from group administered with 2.5 $\log_{10}$ $CCID_{50}$ dose were found responder at D26 and D41, respectively.

For the vYF pMSL candidates from the Stamaril® lineage TV2212, TV2232 and TV2241, no significant difference was observed between the two tested doses (all p-values >0.07 whatever the vYF pMSL candidates and the time point) with GMT ranging from 144 to 505 at D26 and from 115 to 1159 at D41 for 2.5 $\log_{10}$ $CCID_{50}$ dose compared to GMT ranging from 115 to 373 at D26 and from 465 to 955 at D41 for 5.5 $\log_{10}$ $CCID_{50}$. None of the vYF pMSL candidates from the Stamaril® lineage was able to induce a sustained neutralizing antibody response in all the immunized animal whatever the tested dose and whatever the immunization schedule (after 1 or 2 immunization). The percentage of responder hamsters was found to range from 53% to 93% after one immunization and from 43% to 93% after two immunizations with TV2212, TV2232 and TV2241, whatever the dose.

For the vYF pMSL candidates from the YF-VAX® lineage TV3111, TV3112 and TV4221, no significant difference was observed between the two tested doses (all p-values >0.06 whatever the vYF strains and the time point) except for TV3111 for which the 2.5 $\log_{10}$ CCID$_{50}$ dose induced significantly higher neutralizing antibody titers than 5.5 $\log_{10}$ CCID$_{50}$ (p-value=0.04 and 0.003 at D26 and D41, respectively). For 2.5 $\log_{10}$ CCID$_{50}$ dose, the induced GMTs were high and ranging from 3939 to 8898 at D26 and from 3771 to 13674 at D41 whereas for 5.5 $\log_{10}$ CCID$_{50}$ dose, GMTs ranged from 2071 to 5145 at D26 and from 1821 to 6421 at D41. The vYF pMSL candidates from the YF-VAX® lineage were able to induce a sustained neutralizing antibody response in most of the immunized animal after 1 immunization (93% of responder for 2.5 $\log_{10}$ CCID$_{50}$ dose of TV3111 and 100% responders for all the other vYF pMSL candidates from the YF-VAX® lineage whatever the tested dose). After two immunizations all vYF pMSL candidates from the YF-VAX® lineage were able to induce a sustained neutralizing antibody response in 100% of the immunized hamster, whatever the dose.

With respect to the comparison of each of the vYF pMSL candidates to the Stamaril® reference, the neutralizing responses induced by 2.5 $\log_{10}$ CCID$_{50}$ dose of the vYF pMSL candidates issued from the YF-VAX® lineage TV3111, TV3112 and TV4221 were significantly non inferior to those obtained with Stamaril® reference vaccine (p-values≤0.010 and ≤0.047 at D26 and D41, respectively). No significant non inferiority was shown for the vYF strains issued from the Stamaril® lineage (all p-values ≥0.25, whatever the dose and the time point) neither for the vYF strains issued from the YF-VAX® lineage administered at 5.5 $\log_{10}$ CCID$_{50}$ (p-values >0.49, whatever the time point).

Example 5—Toxicity and Immunogenicity of the vYF TV3112 Strain in a Monkey Model A preliminary toxicity study and an immunogenicity study were conducted in nonhuman primates (NHP). The non-human primates, and particularly the rhesus macaques or the cynomolgus macaques, are conventionally used to evaluate the safety and the infectivity, as measured by viremia, and the immunogenicity of vaccine candidates against flaviruses (dengue, yellow fever . . . ). In the context of yellow fever, monkeys are natural hosts; the virus was first isolated in monkeys and it is in this model that the attenuation of vaccine strains was evaluated. Since the 2000's, "small animal" models have been described and can be used to evaluate certain properties of candidate vaccines as performed for the vYF pMSL candidate selection. These models (hamster, mouse A129) however have limitations and macaque remains to this day the most predictive gold standard model compared to humans and is widely described in the literature, e.g. Julander (2016), Mason et al. (1973), Monath et al. (2010) and Moulin et al. (2013). In addition, this model is recommended in the regulatory guidelines.

5.1/Methods
5.1.1/Group Definition and Objectives

Three groups of nine 2 years old male cynomolgus monkeys (*Macaca fascicularis*) imported from Mauritius were immunized by SC route with 500 μL of Stamaril® (one human dose corresponding to 4.2 $\log_{10}$ CCID$_{50}$/dose), one dose of YF-VAX® (6.2 $\log_{10}$ CCID$_{50}$) or 4.2 $\log_{10}$ CCID$_{50}$ of vYF TV3112 WSL candidate.

As primary readouts, the vaccine candidate was compared to each of the reference vaccines, for evaluation of i) vaccine safety, ii) its ability to induce YF specific viremia and viral load in organs: liver, spleen, kidney, lymph node and brain (assessed by viral RNA quantification by YF-NS5 qRT-PCR, as described in Mantel et al. (2008)) and iii) induction of yellow fever specific seroneutralizing antibody responses (assessed by μPRNT$_{50}$ assay) defined as the correlate of protection.

As secondary readouts, in order to identify other potential biomarkers of vaccine performance, different parameters were monitored. These analyses addressed: i) the persistence of the antibody response, and ii) the B and T cellular immune response including memory responses.

5.1.2/Anaesthesia

For the immunizations and at certain occasions (e.g. blood samplings combined with other manipulations during the acclimatization period or if monkeys are refractory to blood samplings without anaesthesia), a mild anaesthesia was performed. Ketamine (Imalgene 1000, MERIAL®) at 10 mg/kg was injected intramuscularly in the thigh.

5.1.3/Monitoring

All animals were weighed at D-29 and D0, observed daily for clinical signs up to D7 and their individual body temperature (transponder system) was recorded at D-17 and during viremia expected period at D0, D3, D4, D5, D6 and D7. Hematology, biochemistry and blood viremia were assessed in all monkeys at D1, D3 and D7. Three monkeys of each group were then euthanized and their organs sampled at D7 for histopathology and viral load in organs assessments. The 6 remaining monkeys in each group were further weighed at D27, D60, D90, D122, D153 and D181 and their individual body temperature was further recorded during viremia expected period at D10 and D14. The 6 remaining monkeys in each group were also observed daily for clinical signs up to D221. Blood samples for seroneutralization, T cells and memory B cells assays were collected from the 6 remaining monkeys in each group at D27, D60, D90, D122, D153, D181 and D221.

5.1.4/Testing Methods

YF-specific seroneutralizing antibodies were titrated using the μPRNT50 method on VERO cells. Briefly, the heat-inactivated sera were serially 2-fold diluted in IMDM (THERMOFISHER SCIENTIFIC)+4% FCS starting from 1:5. YF-17D Stamaril® virus grown on Vero cells was diluted in order to obtain 4000 μPFU/mL in IMDM and incubated 90 minutes with 2-fold diluted serum samples (v/v). The virus/serum mixture was then added to Vero cells in 96-well plates and incubated for 45+/−2 hours. After incubation, cells were fixed with 85% acetone before immunostaining. Plates were blocked with PBS+0.05% Tween 20+2.5% skim milk and incubated first with an anti-flavivirus monoclonal antibody 4G2, and second with a goat anti-mouse IgG HRP conjugate. Finally, plates were stained with the Trueblue™ chromogen. Plaques were counted with Viruscope reader from Microvision™. The final titer is calculated using the least square method and corresponds to the reciprocal of the dilution demonstrating a neutralization of 50% of the plaques.

The LOD of the μPRNT50 assay was about 20 μPRNT50 when the first dilution of serum tested was 1:10. For calculation of the mean value per group, an arbitrary value of half of the LOD was assigned to all samples below the LOD, i.e. 10 μPRNT50.

Memory cellular responses were measured by ELISPOT. The fluorescent-linked immunospot (FLUOROSPOT) is used for detecting and enumerating individual memory B cells secreting antibodies irrespective of antigen specificity (total IgM or total IgG).

On D0 Frozen PBMC were thawed in RPMI medium (THERMOFISHER SCIENTIFIC®) supplemented with 10% FBS and 100 μg/mL of DNase and incubated for 1 hour at 37° C.; 5% $CO_2$. After 1 hour, cells were diluted at 1 million cells/mL and stimulated by incubation for 4 days at 37° C.; 5% $CO_2$ in RPMI 10% FBS supplemented with rIL2 (10 µg/mL).

On D3, the membrane of 96-well FluoroSpot microplates equipped with a low-fluorescent PVDF membrane (MERCK Millipore®) was pre-wetted for 1 minute with 35 µL of 35% ethanol. Each well was washed twice with 200 µL of PBS 1×. Microplates were then coated with YF-17D infected Vero cell lysate (SANOFI PASTEUR®) at dilution 1:80 or a mix of monoclonal antibodies specific for monkeys IgG and IgM at a dilution of 15 µg/mL, and were incubated overnight at 4° C.

On D4, plates were washed with PBS and then blocked at least 2h at 37° C. with RPMI 10% FBS. After plates washing, $2 \times 10^5$ or $4 \times 10^5$ of stimulated PBMC were added in the wells coated with YF-17D infected Vero cell lysate. A range dilution of stimulated cells ($5 \times 10^3$ to $6.2 \times 10^2$) was added to the wells coated with anti-IgG and anti-IgM antibodies.

After 5 hours, the plates were washed 3 times with PBS 1× and stored a 4° C. for the night.

On D7, the plates were washed 6 times with PBS 1X-BSA 0.5% (150 µL/well). After the washing step, 100 µL/well of the anti-monkey IgM-FITC and IgG-CY3 antibodies were added respectively at a dilution of 1/500 in PBS1X-BSA 0.5% for 2 hours at room temperature, in the dark. The plates were washed again 6 times with PBS 1X-BSA 0.5% (150 µL/well). The plates were stored at 5° C.±3° C. in the dark until reading.

Each spot, corresponding to an antibody secreting cell, was enumerated with an automatic FLUOROSPOT plate reader (Microvision™). Results were expressed as number of ACS secreting cell per $10^6$ cells.

T cell responses were determined by IFN-γ IL-2 responses Dual FluoroSpot (FS-2122-10 Monkey IFN-γ/IL-2 FluoroSpot kit from Mabtech®) on isolated PBMC.

Briefly, FluoroSpot PVDF membrane equipped microplates were pre-treated with 35% ethanol, washed, and coated overnight by incubation with monoclonal antibodies against monkey IFN-γ (clone GZ-4, Mabtech®) and against monkey IL-2 (clones IL2M-1/249, Mabtech®) at a concentration of 15 µg/mL in sterile phosphate-buffered saline (PBS) at 4° C. Plates were washed 3 times with PBS and then blocked by incubation for 2 hours at 37° C. with RPMI 1640 medium (Gibco®) supplemented with 10% FCS. PBMC ($4 \times 10^5$) were added to each well with 0.1 µg/mL of monoclonal antibody CD28-A (Mabtech®). YF-Env and YF-NS3 peptide pools (15-mers overlapping peptides covering YF-Env and YF-NS3 amino acid sequences) were added to a final concentration of each peptide in the culture medium of 1 µg/mL. Anti-CD3 mAb (Mabtech®) was used as positive control at 2.5 µg/mL. Plates were incubated for 24 hours at 37° C. in an atmosphere containing 5% $CO_2$. After incubation, plates were washed 6 times with PBS. FITC anti-IFN-γ antibody (clone 7-B6-1-FS-FITC, Mabtech®) and biotinylated anti-IL-2 antibody (IL2-biotin MT8G10, Mabtech®) were added at a concentration of 1:200 and 1 µg/mL, respectively, in 0.5% BSA in PBS; the plates were incubated 2 hours at 37° C. After 3 washes with PBS, incubation was performed with anti-FITC-490 (1:200, Mabtech®) and Streptavidin SA-550 (1:200, Mabtech®) diluted in 0.5% BSA in PBS for 1 hour at room temperature and washed 6 times with PBS. The plates were stored at 5° C.±3° C. in the dark until reading. Fluorescent spots, corresponding to an IFN-γ or IL-2 secreting cell (IFN-γ SC or IL5 SC) as well as polyfunctional T cells secreting both IFN-γ and IL-2 cytokines, were enumerated with an automatic FLUOROSPOT plate reader (Microvision™). Results were expressed as number of IFN-γ or IL-2 secreting cell per $10^6$ PBMCs.

YF vaccine viremia and viral load in organs were monitored by YF-NS5 qRT-PCR (as described in Mantel et al. (2008)).

5.2/Results

The correlate of protection for live-attenuated yellow fever vaccines is defined in the WHO TRS 978, Annex 5, as the induction of measurable neutralizing antibody in a previously seronegative individual, e.g. as a PRNT titer>limit of detection. Neutralizing antibodies far above the pre-established protective threshold (LOD=20) were detected in all monkeys as soon as D14 and during at least 9 months (see FIG. 11). Neutralizing antibody titers were not significantly different from the titers detected after immunization with the current vaccines.

This long-lasting neutralizing antibody response was also supported by a sustained B memory cell frequency monitored in peripheral blood from day 14 up to day 221 after vYF TV3112 vaccination (see FIG. 12 and FIG. 13). These data show that both IgM (FIG. 12) and IgG (FIG. 13) memory B cells developed as soon as day 14 post-vaccination and lasted during the study period for at least 221 days. With respect to vYF TV3112, the kinetics and the percentage of induced memory B cells was similar to the profile of memory B cells induced by both reference vaccines Stamaril® and YF-VAX®.

Moreover, a specific Th1 cellular response (IFN-γ and IL-2 secreting cells) to YF-ENV and YF-NS3 was induced after vYF TV3112 vaccination and was similar to the cellular response observed after vaccination with Stamaril® or YF-VAX® (see FIG. 14).

This study also demonstrated the conserved safety profile of vYF TV3112, as compared to the control vaccines: no clinical signs, no body weight loss, no variation of temperature, no haematology (white and red blood cells; neutrophils; lymphocytes; monocytes; eosinophils; basophils; reticulocytes; platelets; hemoglobin; hematocrit; mean corpuscular volume; mean corpuscular hemoglobin) or biochemical (alkaline phosphatase; alanine transferase; aspartate transferase; gamma glutamyl-transferase; C-reactive protein; bile acids; total bilirubin; albumin; blood urea nitrogen; creatinine) disorders (no statistical differences with Stamaril® and YF-VAX®, via PLS-DA statistical analysis), no or very low viremia (<4 $\log_{10}$ Geq/mL in 1 of the 9 monkeys), no or very low viral RNA detected in Yellow Fever-target organs (100 to 10 000 fold lower than viral load observed after wild-type Asibi infection) (see FIG. 15), no vaccine related histopathological findings in Yellow Fever-target organs.

Example 6—Protection Induced by the vYV TV3112 Strain Against a Lethal Challenge in a Macaque Model The objective was to evaluate protection against yellow-fever virus challenge in macaques immunized with vYF TV3112 vaccine candidate.

6.1/Methods 6.1.1/Animals

Nine months after immunization with Stamaril®, YF-VAX® or vYF TV3112 vaccine candidate, the 6 monkeys remaining at D221 from each of the three animal groups that were studied in the example 5 above were challenged against Yellow Fever with Asibi virulent strain to evaluate vaccine efficacy. Another group of 6 naïve control monkeys was also challenged.

6.1.2/YFV and Buffers

The challenge was conducted with Yellow Fever virus strain Asibi (YFV) from University of Texas Medical Branch (UTMB). YFV (lot 19455, infectious titer 7.7 $Log_{10}$ $CCID_{50}$/mL on VERO cells) was diluted in NaCl+HSA buffer (NaCl 0.4%+Human Serum Albumin (HSA) 2.5%). Each animal was challenged subcutaneously in the up right back site with $10^3$ $CCID_{50}$ of YFV in 1 mL of NaCl+HSA buffer.

6.1.3/Monitoring

Animals were followed for 28 days after Asibi challenge. The animals were observed daily for food consumption and behaviour. Rectal temperature and body weight were recorded at each sampling time point. Blood sampling was performed as described in Table 8 below.

TABLE 8

| Time schedule | | | | | | | | | | |
|---|---|---|---|---|---|---|---|---|---|---|
| Days post-infection | -8 | 0 | 2 | 3 | 4 | 5 | 7 | 10 | 14 | 28 |
| Challenge | | X | | | | | | | | |
| Euthanasia | | | | | | | | | | X |
| Observations[1] | X | X | X | X | X | X | X | X | X | X |
| Local scoring | X | X | X | X | X | X | X | X | X | X |
| Blood for haematology[2] | X | | X | X | X | X | X | X | X | X |
| Blood for plasma | X | | X | X | X | X | X | X | X | X |
| Serum for Neut.[3] and Antibody binding | X | | | | | | X | | X | X |
| Serum for biochemistry[4] | X | | X | X | X | X | X | X | X | X |

[1] Clinical observation, body weight, rectal temperature.
[2] White & red blood cells; neutrophils; lymphocytes; monocytes; eosinophils; basophils; reticulocytes; platelets; hemoglobin; hematocrit; mean corpuscular volume; mean corpuscular hemoglobin. [3] Neutralization assay. [4] Alkaline phosphatase; alanine transferase; aspartate transferase; gamma glutamyl-transferase; C-reactive protein; bile acids; total bilirubin; albumin; blood urea nitrogen; creatinine.

6.1.4/in-Life Observations

Animals were observed 7 days a week. At each time of bleeding, clinical examination was performed as described in Table 9 below.

TABLE 9

| Chart of the animal observations | |
|---|---|
| Mortality | Daily |
| Overt signs of disease such as diarrhoea, loss of appetite and lethargy | Daily |
| Body weight | At sampling day[1] |
| Body temperature (rectal) | At sampling day[1] |
| Food and water consumption | Daily evaluation |

[1] See Table 8.

6.2/Results

All the vaccinated monkeys were protected from the challenge effects: viremia (only low viremia, i.e. <3.6 $log_{10}$ GEq/mL in 2/6 monkeys for only one day, measured by YF-NS5 qRT-PCR as described in Mantel et al. (2008)), haematological disorders, blood biochemistry disorders and death.

In this study, 3 out of the 6 NHP in the non-vaccinated control group survived to the challenge but all the 6 control NHP presented viremia (>8 $log_{10}$ Geq/mL), lymphopenia, thrombocytopenia and blood biochemistry disorders with high increase of the level of transaminases, CRP, bilirubin and bile acids.

Accordingly, the vYF TV3112 vaccine candidate was able to protect cynomolgus monkeys, one of the best predictive animal models for yellow fever vaccines, from wild-type Asibi infection, as were the currently available vaccines Stamaril® and YF-VAX®.

Example 7—Sequence Analysis

RNA viruses naturally present high genetic variability levels that are responsible for the quasi-species intrinsic nature of these viruses. Even if the error rate of the Yellow Fever polymerase is described as low for a RNA virus, the polymerase error rate is about $10^{-6}$ substitution per genome per infectious cycle.

The well-defined virus production process is set-up so as to limit this phenomenon to a strict minimum by always keeping the same virus growth conditions. But statistically, virus quasi-species are continuously produced every time the virus replicates in a cell and whenever a variant brings a growth advantage to the virus, it will be conserved and amplified on the long term, progressively replacing the initial population.

In addition, as the new virus growth system will move from egg to Vero cell culture, some adaptation mutation are expected to probably take place. In particular, several mutations in NS4B were described in different Flavivirus models as positive adaptation of the virus to grow in Vero cells (Blaney et al., 2003; Tang et al., 2005; Beasley et al. 2013).

Moreover, the current seed were never cloned, so a mixture of quasi-species co-exists in the current vaccine strains. Reference sequences will be first established by high-throughput sequencing of the genomes of YF-VAX® and Stamaril® vaccines, and then the new pMSL candidate genomes will be compared to them.

As the new pMSL candidates are obtained after 2 cloning steps they represent homogeneous viral populations.

7.3/Methods 7.3.1/Principles

The sequencing of the Yellow Fever virus is carried out after extraction and purification of the viral RNA.

The RNA is then retrotranscribed into complementary DNA and then the genome is completely amplified by PCR using specific primers. PCR products are then used to form a library thanks to the Nextera® XT DNA sample preparation kit (Illumina, Inc.). The formation of the library takes place in several steps. First, the amplicons are assembled in an equimolar manner. Then they are fragmented using transposomes (Tagmentase). Transposomes cut DNA and add adapters. Then a step of amplification by PCR is carried out thanks to primers complementary to adapters. This step allows the addition, on both sides of the fragments, of indexes (used for tagging the sample) and hitch the fragments to the sequencing support. Finally, the library is purified using Agencourt® beads (AMPure® XP, Beckman Coultern Genomics, Inc.) and sequenced using the MiSeq sequencer (Illumina®, Inc.).

Once the sequences obtained, the analysis is then carried out with the analysis module "Quality-based variant detection (legacy)" of the CLC Genomics Workbench software (QIAGEN®).

Z3.2) RNA Extraction

The viral RNA was extracted from 140 µl of viral suspension at a minimum concentration of $10^8$ Geq/mL (quantification by YF-NS5 qRT-PCR) with the Qiamp Viral kit (QIA- GEN®) according to the supplier's recommendations. Purified viral RNA purified was eluted in 140 μl of nuclease-free water.

7.3.3) RT-PCR

First, a specific retrotranscription (RT) step of the RNA into cDNA was carried out using the three antisense primers, intended to overlap the genome of the yellow fever virus. Then a PCR amplification was performed using the three primer pairs described in Table 10.

TABLE 10

| Primers sequences (MWG ®) | | | | |
|---|---|---|---|---|
| SEQ ID NO. | Sequence (5'->3') | Nb of nt | Size of the amplicon | Position on genome |
| 9 | GCTAGGCAATAAACACATTTGGA | 23 | 4146 | 49-4195 |
| 10 | TTCACTGGGATACTCCTTCGC | 21 | | |
| 11 | ATCAAATACCATCTTGCCCCTC | 22 | 4009 | 3940 -7949 |
| 12 | AGTAAATCCTTTGACCCCACT | 21 | | |
| 13 | GGCTTACCGCAATGCACT | 18 | 4235 | 6553-10788 |
| 14 | CAGAGAACCACTCCGGTC | 18 | | |

Three mixes containing one of the three antisense primers (SEQ ID NO. 10; SEQ ID NO. 12 or SEQ ID NO. 14) were prepared (see Table 11 below).

TABLE 11

| Mix for one sample | |
|---|---|
| Mix of reverse primers (10 μM) | 1 μL |
| dNTP (10 mM) | 1 μL |
| Nuclease-free water | 5 μL |
| Extracted RNA | 5 μL |

The samples were heated in the thermocycler for 5 minutes at +65° C., and a heat shock was immediately carried out by incubating the tubes for 3 minutes in the ice.

A mix was then prepared as described in Table 12 below.

TABLE 12

| Mix for one viral RNA sample (4 RT reactions): | |
|---|---|
| RT buffer | 16 μL |
| DTT (0.1M) | 4 μL |
| RNAse OUT (LIFE TECHNOLOGIES ®) | 2 μL |
| Superscript III (LIFE TECHNOLOGIES ®) | 2 μL |
| Nuclease-free water | 8 μL |

To each of the three RNA/primers tubes, 12 μl of this mix were added and the reverse transcription run was performed as described in Table 13 follows:

TABLE 13

| RT program | | |
|---|---|---|
| Step | Time (min) | Temperature (° C.) |
| Reverse transcription step | 60 min | +50° C. |
| Inactivation of the enzyme | 5 min | +85° C. |
| Hold | — | +10° C. |

1 μl of RNAse H are added in each of the tubes and the tubes were incubated for 20 minutes at 37° C. in a thermocycler.

From the obtained cDNA, the amplification was performed into three amplicons by PCR. Three PCR mixes were prepared as described in Table 14 below containing one of the three pairs of primers (SEQ ID NO. 9 and SEQ ID NO. 10; SEQ ID NO. 11 and SEQ ID NO. 12; SEQ ID NO. 13 and SEQ ID NO. 14).

TABLE 14

| PCR mix for one sample | |
|---|---|
| 5X Phusion HF Buffer (BioLabs ®) | 5 μL |
| dNTPs 10 mM | 1 μL |
| Forward primer 10 μM | 1 μL |
| Reverse primer 10 μM | 1 μL |
| Nuclease-free water | 12.5 μL |
| Phusion HF DNA polymerase (BioLabs ®) | 0.5 μL |

20 μl of each mix were added to the 5 μl of corresponding cDNA.

The PCR program was as described in Table 15 below.

TABLE 15

| PCR program | | |
|---|---|---|
| Step | Time (sec or min) | Temperature (° C.) |
| Initial denaturation | 30 sec | +98° C. |
| 35 cycles | | |
| Denaturation | 10 sec | +98° C. |
| Hybridization of primers | 20 sec | +58° C. |
| Elongation | 4 min | +72° C. |
| Final elongation | 5 min | +72° C. |
| Hold | — | +10° C. |

7.3.5) Analysis and Purification of the Amplicons

All amplicons were analysed on 1.2% agarose gel in order to check the quality of amplification. The amplicons were purified manually using the QIAQuick® PCR purification kit (QIAGEN®) according to the supplier's recommendations.

7.3.6) Formation of a Library with the Nextera® XT Kit (Illumina, Inc.)

Purified amplicons were quantified with the Qubit® 2.0 Fluorometer (LIFE TECHNOLOGIES®) using the Qubit® dsDNA HS Assay kit, according to the supplier's recommendations.

Following the assay, the amplicons were serially diluted in nuclease-free water in order to obtain a final concentration of 0.2 ng/μL. Then, for each sample, the three amplicons were mixed to obtain a single concentrated PCR pool at 0.6 ng/μL.

The PCR program was as described in Table 16 below.

TABLE 16

| PCR program | | |
|---|---|---|
| Step | Time (sec or min) | Temperature (° C.) |
| Activation of the DNA polymerase | 3 min | +72° C. |
| Initial denaturation | 30 sec | +95° C. |
| 12 cycles | | |
| Denaturation | 10 sec | +95° C. |
| Hybridization of primers | 30 sec | +55° C. |
| Elongation | 30 sec | +72° C. |
| Final elongation | 5 min | +72° C. |
| Hold | — | +10° C. |

The amplicons were purified and calibrated by the mean of the Agencourt® AMPure® XP kit (BECKMAN COULTER®) according to the supplier's recommendations. The library was stable at −20° C. for a week.

7.3.7) Analysis of the Library

Quantification of the library was performed with the Qubit® 2.0 Fluorometer (LIFE TECHNOLOGIES®) using the Qubit® dsDNA HS Assay kit, according to the supplier's recommendations.

7.3.8) Sequencing of the library

The library was sequenced by a MiSeq system (ILLUMINA®), according to the supplier's recommendations. The sequences were analysed by the ILLUMINA® Sequencing Analysis Viewer (Illumina, Inc.), according to the supplier's recommendations.

The analysis of the generated sequences was performed with the CLC Genomics Workbenck 7.5.2 software (QIAGEN®), according to the supplier's recommendations.

7.4/Results 7.4.1) Reference Sequences for YF-VAX® and Stamaril® Vaccines

The reference sequence of YF-VAX® vaccine was represented as SEQ ID NO. 2. The reference sequence of Stamaril® vaccine was found as SEQ ID NO. 3.

7.4.1.1) Stamaril®-Derived pMSLs pMSL candidate genomes (passage no 8) were sequenced and compared to their parent strain genome. The table 17 below provides the result of the high throughput sequencing for the three strains from the Stamaril® lineage.

TABLE 17

Sequencing result of strains from the Stamaril ® lineage

| Strain | #nt[1] | Ref nt (Stamaril ®)[2] | Seq nt[3] | Ref codon (Stamaril ®) | Seq codon | Freq (%) | Annotation[4] | AA change |
|---|---|---|---|---|---|---|---|---|
| TV2212 | 2524 | C | U | GAC | GAU | 100% | NS1-24 | — |
| TV2232 | 5590 | U | G | GUU | GUG | 100% | NS3-340 | — |
|  | 5695 | C | U | GUC | GUU | 100% | NS3-375 | — |
|  | 7766 | U | C | UUG | CUG | 100% | NS5-47 | — |
|  | 8404 | C | U | GAC | GAU | 100% | NS5-256 | — |
|  | 6379 | A | G | GAA | GAG | 99% | NS3-603 | — |
| TV2241 | 2524 | C | U | GAC | GAU | 100% | NS1-24 | — |

[1]Nucleotide position from the 5' first nucleotide. [2]Nucleotide of the Stamaril ® reference genome. [3]Mutated nucleotide as compared to the corresponding nucleotide from the Stamaril ® reference genome. [4]Corresponding YFV protein and corresponding amino acid position in the protein.

TV2241 and TV2212 present a single mutation compared to the Stamaril® parent strain used as the reference (nucleotide 2524 located in the NS1 coding region, silent at the amino acid level). TV2232 shows a different profile, having five mutations in NS3 and NS5, all silent.

7.4.1.2) YF-VAX®-Derived pMSLs

The table 18 below provides the result of the high throughput sequencing for the three pMSL candidates (passage no 8) from the YF-VAX® lineage.

TABLE 18

Sequencing results of YF-VAX ®-derived strains

| Strain | #nt[1] | Ref nt (YF-VAX ®)[2] | Seq nt[3] | Ref codon (YF-VAX ®) | Seq codon | Freq (%) | Annotation[4] | AA change[5] |
|---|---|---|---|---|---|---|---|---|
| TV3111 | 2411 | G | U | GUA | UUA | 100% | E-480 | Val480Leu |
|  | 3701 | A | G | AUG | GUG | 100% | NS2a-65 | Met65Val |
|  | 6496 | A | G | AAA | AAG | 100% | NS4a-19 | — |
| TV3112 | 3701 | A | G | ATG | GUG | 100% | NS2a-65 | Met65Val |
|  | 2411 | G | U | GUA | UUA | 100% | E-480 | Val480Leu |
|  | 6496 | A | G | AAA | AAG | 100% | NS4a-19 | — |
|  | 1408 | A | U | GUA | GUU | 100% | E-145 | — |
| TV4221 |  |  |  |  | No variant identified |  |  |  |

[1]Nucleotide position from the 5' first nucleotide. [2]Nucleotide of the YF-VAX ® reference genome. [3]Mutated nucleotide as compared to the corresponding nucleotide from the YF-VAX ® reference genome. [4]Corresponding YFV protein and corresponding amino acid position in the protein. [5]Mutated amino acid and position in the protein as compared to the corresponding amino acid from the YF-VAX ® reference.

TV4221 is identical to the reference sequence of YF-VAX® vaccine strain.

TV3111 has 3 mutations at position 2411 (E-480, Val to Leu), 3701 (NS2a-65, Met to Val) and 6496 (NS4a-19, silent).

TV3112 has the same mutations as TV3111, plus one additional mutation at position 1408 (E-145, silent).

TV3112 and TV3111 strains comprise an envelope protein represented by SEQ ID NO 15 (with a leucine residue at position 480). SEQ ID NO 16 (with a valine residue at position 65) is the sequence of the NS2a protein from TV3112 and TV3111 strains. SEQ ID NO 17 (with a G nucleotide at position 57) is the RNA sequence coding for the NS4a protein from TV3112 strain. SEQ ID NO 18 (with a U nucleotide at position 435) is the RNA sequence coding for the envelope protein from TV3112 strain.

It is well-known to the skilled person that the role of the genome is to be the support of information and that the proteins through their function have a role in the virus phenotype. Silent mutations have no impact on the function of the proteins. Accordingly, TV3112 and TV3111 strains can be described as live-attenuated yellow fever virus strains comprising a nucleic acid molecule encoding:
(i) an envelope protein comprising a mutation at position 480 which results in an amino acid change from valine to leucine, and
(ii) a NS2a protein comprising a mutation at position 65 which results in an amino acid change from methionine to valine. Or TV3112 and TV3111 strains can be described as live-attenuated yellow fever virus strains comprising a nucleic acid molecule encoding:
(i) an envelope protein which comprises a leucine residue at the position within the protein that corresponds to position 480 of SEQ ID NO. 15; and
(ii) an NS2a protein which comprises a valine residue at the position within the protein that corresponds to position 65 of SEQ ID NO. 16.

7.4.2) YF-VAX®-Derived TV3112 Strain, at the MSL and WSL Stages

The consensus sequence of the TV3112 MSL remained identical to that of its pMSL parent (TV3112 pMSL). The consensus sequence of TV3112 WSL remained identical to its MSL parent (TV3112 MSL). TV3112 strain is genetically stable and keeps in its consensus sequence the mutations at nucleotide positions 1408, 2411, 3701 and 6496, from pMSL to WSL stages.

REFERENCES

Non Patent References

Barrett A D T. Yellow fever live attenuated vaccine: A very successful live attenuated vaccine but still we have problems controlling the disease. Vaccine. 2017 Oct. 20; 35(44):5951-5955.

Beasley D W, Morin M, Lamb A R, Hayman E, Watts D M, Lee C K, Trent D W, Monath T P. Adaptation of yellow fever virus 17D to Vero cells is associated with mutations in structural and non-structural protein genes. Virus Res. 2013 September; 176(1-2):280-4.

Blaney J E Jr, Manipon G G, Firestone C Y, Johnson D H, Hanson C T, Murphy B R, Whitehead S S. Mutations which enhance the replication of dengue virus type 4 and an antigenic chimeric dengue virus type 2/4 vaccine candidate in Vero cells. Vaccine. 2003 Oct. 1; 21(27-30): 4317-27.

dos Santos C N, Post P R, Carvalho R, Ferreira I I, Rice C M, Gaiter R. Complete nucleotide sequence of yellow fever virus vaccine strains 17D D and 17D-213. Virus Res. 1995 January; 35(1):35-41.

Dupuy A, Despres P, Cahour A, Girard M, Bouloy M. Nucleotide sequence comparison of the genome of two 17D-204 yellow fever vaccines. Nucleic Acids Res. 1989 May 25; 17(10):3989.

Erickson A K, Pfeiffer J K. Spectrum of disease outcomes in mice infected with YFV-17D. J Gen Virol. 2015 June; 96:1328-1339.

Hayes E B. Is it time for a new yellow fever vaccine? Vaccine. 2010 Nov. 29; 28(51):8073-6.

Julander J G. Animal models of yellow fever and their application in clinical research. Curr Opin Virol. 2016 June; 18:64-9.

Kolell K. et al. Virus Production in Vero Cells Using a Serum-free Medium. In: Smith R. (eds) Cell Technology for Cell Products (2007). Springer.

Mantel N, Aguirre M, Gulia S, Girerd-Chambaz Y, Colombani S, Moste C, Barban V. Standardized quantitative R T-PCR assays for quantitation of yellow fever and chimeric yellow fever-dengue vaccines. J Virol Methods. 2008 July; 151(1):40-6.

Mason R A, Tauraso N M, Spertzel R O, Ginn R K. Yellow fever vaccine: direct challenge of monkeys given graded doses of 17D vaccine. Appl Microbiol. 1973 April; 25(4): 539-44.

Meier K C, Gardner C L, Khoretonenko M V, Klimstra W B, Ryman K D. A mouse model for studying viscerotropic disease caused by yellow fever virus infection. PLoS Pathog. 2009 October; 5(10).

Monath T P. Yellow fever vaccine. Expert Rev Vaccines. 2005 August; 4(4):553-74.

Monath T P, Lee C K, Julander J G, Brown A, Beasley D W, Watts D M, Hayman E, Guertin P, Makowiecki J, Crowell J, Levesque P, Bowick G C, Morin M, Fowler E, Trent D W. Inactivated yellow fever 17D vaccine: development and nonclinical safety, immunogenicity and protective activity. Vaccine. 2010 May 14; 28(22):3827-40.

Moulin J C, Silvano J, Barban V, Riou P, Allain C. Yellow fever vaccine: comparison of the neurovirulence of new 17D-204 Stamaril™ seed lots and R K 168-73 strain. Biologicals. 2013 July; 41(4):238-46.

Needleman S B, Wunsch C D. A general method applicable to the search for similarities in the amino acid sequence of two proteins. J Mol Biol. 1970 March; 48(3):443-53.

Pereira R C, Silva A N, Souza M C, Silva M V, Neves P P, Silva A A, Matos D D, Herrera M A, Yamamura A M, Freire M S, Gaspar L P, Caride E. An inactivated yellow fever 17D D vaccine cultivated in Vero cell cultures. Vaccine. 2015 Aug. 20; 33(35):4261-8.

Remington's Pharmaceutical Sciences (18th edition), ed. A. Gennaro, 1990, Mack Publishing Company, Easton, Pa.

Rice C M, Lenches E M, Eddy S R, Shin S J, Sheets R L, Strauss J H. Nucleotide sequence of yellow fever virus: implications for flavivirus gene expression and evolution. Science. 1985 Aug. 23; 229(4715):726-33.

Tang W F, Eshita Y, Tadano M, Morita K, Makino Y. Molecular basis for adaptation of a chimeric dengue type-4/Japanese encephalitis virus to Vero cells. Microbiol Immunol. 2005; 49(3): 285-94.

World Health Organization. Requirements for yellow fever vaccine. WHO Technical report series, 1998, No. 872, Annex 2, 30-68.

World Health Organization. Recommendations to assure the quality, safety and efficacy of live attenuated yellow fever vaccines. WHO Technical report series, 2010, No. 978, Annex 5, 241-314.

Patent References

WO 2009/109550
WO 2014/016360

The invention claimed is:

1. A live-attenuated yellow fever virus strain which comprises an envelope protein comprising a leucine residue at the position within the protein that corresponds to position 480 of SEQ ID NO. 15, wherein the envelope protein comprises a sequence that is at least 90%, 95%, 98% or 100% identical to the sequence of SEQ ID NO. 15.

2. The live-attenuated yellow fever virus strain of claim 1, wherein the live-attenuated yellow fever virus strain further comprises an NS2a protein comprising a valine residue at the position within the protein that corresponds to position 65 of SEQ ID NO. 16, wherein the NS2a protein comprises a sequence that is at least 90%, 95%, 98% or 100% identical to the sequence of SEQ ID NO. 16.

3. The live-attenuated yellow fever virus strain of claim 2 comprising a nucleic acid molecule encoding:
   (i) an envelope protein which comprises a leucine residue at the position within the protein that corresponds to position 480 of SEQ ID NO. 15; and
   (ii) an NS2a protein which comprises a valine residue at the position within the protein that corresponds to position 65 of SEQ ID NO. 16.

4. The live-attenuated yellow fever virus strain of claim 3, wherein the nucleic acid further comprises a G nucleotide at a position within the nucleic acid coding for the non-structural protein 4A (NS4a) that corresponds to position 57 of SEQ ID NO. 17, wherein the nucleic acid encoding the NS4a protein comprises a sequence that is at least 90%, 95%, 98% or 100% identical to the sequence of SEQ ID NO. 17.

5. The live-attenuated yellow fever virus strain of claim 4, wherein the nucleic acid further comprises a U nucleotide at a position within the nucleic acid coding for the envelope protein (E) that corresponds to position 435 of SEQ ID NO. 18, wherein the nucleic acid encoding for the envelope protein comprises a sequence that is at least 90%, 95%, 98% or 100% identical to the sequence of SEQ ID NO. 18.

6. An immunogenic composition comprising the live-attenuated yellow fever virus strain of claim 1 and a pharmaceutically acceptable vehicle.

7. A vaccine composition comprising the immunogenic composition of claim 6.

8. The vaccine of claim 7, wherein the vaccine is formulated for mucosal administration, parenteral administration, or oral administration.

9. A method for immunizing an individual against an infection by a yellow fever virus, the method comprising administering the vaccine of claim 7 to an individual in need thereof, thereby immunizing the individual against the infection.

10. The live-attenuated yellow fever virus strain of claim 1, wherein the live-attenuated yellow fever virus strain comprises a RNA sequence with no more than 5 mutated nucleotides in SEQ ID NO. 7.

11. The live-attenuated yellow fever virus strain of claim 1, wherein the live-attenuated yellow fever virus strain comprises the RNA sequence of SEQ ID NO. 7.

12. An immunogenic composition comprising the live-attenuated yellow fever virus strain of claim 11 and a pharmaceutically acceptable vehicle.

13. A vaccine composition comprising the immunogenic composition of claim 11.

14. The vaccine of claim 13, wherein the vaccine is formulated for mucosal administration, parenteral administration or oral administration.

15. A method for immunizing an individual against an infection by a yellow fever virus, the method comprising administering the vaccine of claim 13 to an individual in need thereof, thereby immunizing the individual against the infection.

* * * * *

SEQUENCE LISTING

```
<160> NUMBER OF SEQ ID NOS: 18

<210> SEQ ID NO 1
<211> LENGTH: 10862
<212> TYPE: RNA
<213> ORGANISM: Yellow fever virus
<220> FEATURE:
<221> NAME/KEY: misc_feature
<223> OTHER INFORMATION: RNA sequence of the YFV 17D204 strain

<400> SEQUENCE: 1
aguaaauccu gugugcuaau ugaggugcau uggucugcaa aucgaguugc uaggcaauaa      60
acacauuugg auuaauuuua aucguucguu gagcgauuag cagagaacug accagaacau     120
gucuggucgu aaagcucagg gaaaaacccu gggcgucaau augguacgac gaggaguucg     180
cuccuuguca aacaaaauaa aacaaaaaac aaaacaaauu ggaaacagac cuggaccuuc     240 aagaggguguu caaggauuua ucuuuuucuu uuuguucaac auuuugacug gaaaaaagau     300
cacagcccac cuaaagaggu gugaaaau gcuggaccca agacaaggcu uggcuguucu      360
aaggaaaguc aagagagugg uggccaguuu gaugagagga uuguccucaa ggaaacgccg     420
uucccaugau guucugacug ugcaauuccu aauuuuggga augcuguuga ugacggguug      480
agugaccuug gugcggaaaa acagauggu gcuccuaaau gugacaucug aggaccucgg     540
gaaaacauuc ucuguggggca caggcaacug cacaacaaac auuuuggaag ccaaguacug     600
gugcccagac ucaauggaau acaacuguccc caaucucagu ccaagagagg agccagauga     660
cauugauugc uggugcuaug ggguggaaaa cguuagaguc gcauauggua agugugacuc      720
agcaggcagg ucuaggaggu caagaaggg cauugacuug ccuacgcaug aaaaccaugg     780
uuugaagacc cggcaagaaa aauggaugac uggaagaaug ggugaaaggc aacuccaaaa      840
gauugagaga ugguucguga ggaaccccuu uuuugcagug acgggcucuga ccauugccua      900 ccuuguggga agcaacauga cgcaacgagu cgugauugcc cuacuggucu uggcuguugg      960
uccggccuac ucagcucacu gcauuggaau uacugacagg gauuucauug aggggguuca     1020
uggaggaacu uggguuucag cuacccuggaa gcaagcaag uguucacug uuauggcccc     1080 ugacaagccu ucauuggaca ucucacuaga gacaguagcc auugauagac cugcugaggu     1140
gaggaaagug uguuacaaug caguucuac ucauuugaag auuuaaugaca agugcccacag      1200 cacuggagag gcccaccuag cugaagagaa cgaagggggac aaugcgugca agcgcacuua     1260
uucugauaga ggcuggggca auggcuguug ccuauuuggg aaagggagca uuguggcaug     1320
cgccaaauuc acuuguguuc aauccaugag uuuguuugag uugaucgaga caaaauuca     1380 guaugucauc agagcacaau ugcauguagg ggccaagcag gaaaauugga auaccgacau     1440
uaagacucuc aaguuugaug cccugucagg cucccaggaa gucgaguuca uugggguaugg     1500 aaaagcuaca cuggaaugcc aggugcaaac ugcgguggac uuuggauaaca guuacaucgc     1560 ugagauggaa acagagagcu ggauaguggaa cagacagugg gcccaggacu ugacccugcc      1620
auggcagagu ggaagguggcg gggugugagag agagaugcau caucuuugucg aauuugaacc     1680 uccgcaugcc gccacuauca gauacguggc ccugggaaac caggaaggcu ccuugaaaac     1740
agcucuuacu ggcgcaauga gggguuacaaa ggacacaaau gacaacaacc uuuacaaacu     1800
```

```
acauggugga cauguuucuu gcagagugaa auugucagcu uugacacuca aggggacauc    1860
cuacaaaaua ugcacugaca aaauguuuuu ugucaagaac ccaacugaca cuggccaugg    1920
cacuguugug augcagguga aagucaaaa aggagccccc ugcaggauuc cagugauagu    1980
agcugaugau cuuacagcgg caaucaauaa aggcauuuug guuacaguua accccaucgc    2040
cucaaccaau gaugaugaag ugcugauuga ggugaaccca ccuuuuggag acagcuacau    2100
uaucguuggg agaggagauu cacgucucac uuaccagugg cacaaagagg gaagcucaau    2160
aggaaaguug uucacucaga ccaugaaagg cguggaacgc cuggccguca ugggagacac    2220
cgccugggau uucagcuccg cuggagggu cuucacuucg guugggaaag gaauucauac    2280
ggguuuuggc ucugccuuuc aggggcuauu uggcggcuug aacuggauaa caaaggucau    2340
caugggggcg guacuuauau gguuggcau caacacaaga aacaugacaa uguccaugag    2400
caugaucuug guaggaguga ucaugauguu uuugucucua ggaguggggg cggaucaagg    2460
augcgccauc aacuuggca agagagagcu caagugcgga gaugguaucu ucauauuuag    2520
agacucugau gacuggcuga acaaguacuc auacuauca gaagauccug ugaagcuugc    2580
aucaauagug aaagccucuu uugaagaagg gaagugguggc cuaaauucag uugacucccu    2640
ugagcaugag auguggagaa gcagggcaga ugagaucaau gccauuuuug aggaaaacga    2700
ggugacauu ucuguugucg ugcaggaucc aaagaauguu uaccagagag gaacucaucc    2760
auuuuccaga auucgggaug ucucuagua ugguuggaag acuuggggua agaaccuugu    2820
guucucccca gggaggaaga augggaagcuu caucauagau ggaaagucca ggaaagaaug    2880
cccguuuuca aaccgggucu ggaauucuuu ccagauagag gaguuuggga cgggagiguu    2940
caccacacgc guguacaugg acgcagucuu ugaauacacc auagacugcg auggaucuau    3000
cuugggugca gcggugaacg gaaaaaagag ugcccauggc ucuccaacau uuugggauggg    3060
aagucaugaa guaaauggga caugguagu ccacaccuug gaggcauag auuacaagga    3120
gugugagugu ccacugacac auacgauugg aacaucaguu gaagagagug aaauguucau    3180
gccgagauca aucggaggcc caguuagcuc ucacaaucau aucccuggau acaagguuca    3240
gacgaacgga ccuuggaugc agguaccacu agaagugaag agagaagcuu gcccagggac    3300
uagcgugauc auugauggca acugugaugg acggggaaaa ucaaccagau ccaccacgga    3360
uagcgggaaa guuauuccug aauggugguug ccgcuccugc acaaugccgc cugugagcuu    3420
ccauggugu gauggguguu gguaucccau ggaaauuagg ccaaggaaaa cgcaugaaag    3480
ccaucggug cgcuccuggg uuacagcugg agaaauacau gcuguccc uu uugguuggu    3540
gagcaugaug auagcaaugg aaguggucuu aaggaaaaga cagggaccaa agcaaauguu    3600
gguuggagga guagugcucu ugggagcaau gcuggcgggg caaguaacuc uccuugauuu    3660
gcugaaacuc acaguggcug ugggauugca uuuccaugag augaacaaug gaggagacgc    3720
cauguauaug gcguugauug cugccuuuuc aaucagacca gggcugcuca ucggcuuugg    3780
gcucaggacc cuauggagcc cucggaacg ccuugugcug acccuaggag cagccauggu    3840
ggagauugcc uuggguggcg ugaugggcgg ccugguggaag uaucuaaaug caguuucucu    3900
cugcauccga acaauaaaug cuguugccuu uaggaaagca ucaaauacca ucuugcccu    3960
caugcucug uugacaccug ucacuauggc ugaggugaga cuugccgcaa guucuuuug    4020
ugccgugguu aucauagggg uccucaccca gaauuucaag gacaccucca ugcagaagac    4080
uauaccucug guggcccuca caccucacauc uuaccugggc uugacacaac cuuuuuggg    4140
ccugugugca uuucuggcaa cccgcauauu uggcgaagg aguaucccag ugaaugaggc    4200
```

```
acucgcagca gcuggucuag ugggagugcu ggcaggacug gcuuuucagg agauggagaa    4260
cuuccuuggu ccgauugcag uuggaggacu ccugaugaug cugguuagcg uggcugggag    4320 ggugggauggg cuagagcuca agaagcuugg ugaaguuuca ugggaagagg aggcggagau   4380
cagcgggagu uccgcccgcu augauguggc acucagugaa caaggggagu ucaagcugcu   4440
uucugaagag aaagugccau gggaccaggu ugugaugacc ucgcuggccu ugguuggggc   4500
ugcccuccau ccauuugcuc uucgcuggu ccuugcuggg uggcuguuuc augucagggg    4560
agcuaggaga agugggaug ucuuguggga uauucccacu ccaagauca ucgaggaaug    4620 ugaacaucug gaggauggga uuuauggcau auuccaguca accuucuugg gggccuccca   4680
gcgaggagug ggaguggcac agggaggggu guuccacaca auguggcaug ucacaagagg   4740
agcuuuccuu gucaggaaug gcaagaaguu gauuccaucu ugggcuucag uaaggaaga    4800 ccuugucgcc uaugguggcu caugggaaguu ggaaggcaga ugggauggag aggaagaggu   4860
ccaguugauc gcggcuguuc caggaaagaa cguggucaac guccagacaa aaccgagcuu   4920
guucaaagug aggaauggg gagaaaucgg ggcugucgcu cuugacuauc cgagugggcac  4980 uucaggaucu ccuauuguua acaggaacgg agaggugauu gggcuguacg gcaauggcau   5040
ccuugucggu gacaacuccu ucgugucccgc cauaucccag acgagggugaa aggaagaagg   5100 aaaggaggag cuccaagaga uccccgacaau gcuaaagaaa ggaaugacaa cugcccuga   5160 uuuucauccu ggagcuggga agacaagacg uuccucccca cagaucuugg ccgagugcgc    5220
acggagacgc uugcgcacuc uuguguuggc ccccaccagg guuguucuuu cugaaaugaa    5280
ggaggcuuuu cacggccugg acgugaaauu ccacacacag gcuuuuuccg cucacggcag    5340
cgggagagaa gucauugaug ccaugugcca ugccacccua acuuacagga uguuggaacc   5400 aacuagggu guuaacuggg aagugaucau uauggaugaa gcccauuuuu uggauccagc    5460
uagcauagcc gcuagaggu gggcagcgca cagagcuagg gcaaaugaaa gugcaacaau    5520
cuugaugaca gccacaccgc cugggacuag ugaugaauuu ccacauucaa augugaaau    5580 agaagauguu caaacggaca uacccaguga gcccuggaac acagggcaug acuggauccu    5640
agcugacaaa aggcccacgg cauggcuuccu uccauccauc agagcugcaa augucauggc    5700
ugccucuuug cguaaggcug gaaagagugu gguggguccug aacaggaaaa ccuuugagag   5760
agaauacccc acgauaaagc agaagaaacc ugacuuuaua uuggcacug acauagcuga    5820 aauggagcc aaccuuugcg uggagcgagu gcuggauugc aggacggcuu uuaagccugu    5880
gcuuguggau gaaggaggga aagguggcaau aaaagggcca cuucguaucu ccgcauccuc    5940
ugcugcucaa aggagggggc gcauugggag aaaucccaac agagauggag acucauacua    6000 cuauucgag ccuacaagug aaaauaaugc ccaccgguc ugcugguugg aggccuccaau    6060 gcucuuggac aacauggagg ugaggggugg aauggucgcc ccacucuaug gcguugaagg    6120
aacuaaaaca ccaguuuccc cuggugaaau gagacugagg gaugaccaga ggaaagucuu    6180
cagagaacua gugaggaauu gugaccugcc cguuuggcuu ucguggcaag uggccaaggc    6240
ugguuugaag acgaaugauc guaagguggu uuugaaggc ccugaggaac augagaucuu    6300
gaaugacagc ggugaaacag ugaagugcag ggccuccuga ggagcaaaga agccucugcg    6360
cccaaggugg ugugaugaaa ggugugcauc ugaccagagu gcgcugucug aauuuauuaa    6420
guuugcugaa gguaggaggg gagcugcuga agucuaguu gucugaguga acucccuga    6480 uuuccuggcu aaaaaagggug gagaggcaau ggauaccauc agugugcuucc uccacucuga    6540
```

```
ggaaggcucu agggcuuacc gcaaugcacu aucaaugaug ccugaggcaa ugacaauagu    6600
caugcuguuu auacuggcug gacuacugac aucgggaaug gucaucuuuu ucaugcucc     6660 caaaggcauc aguagaaugu cuauggcgau gggcacaaug gccggcugug gauaucucau    6720
guuccuugga ggcgucaaac ccacucacau cuccuaugu augcucauau ucuuuguccu     6780
gauggugguu gugaucccg agccagggca acaaaggucc auccaagaca accaagugc      6840 auaccucauu auuggcaucc ugacgcuggu ucagcggug gcagccaacg agcuaggcau     6900
gcuggagaaa accaaagagg accucuuugg gaagaagaac uuaauuccau cuagugcuuc    6960
acccuggagu uggccggauc uugaccgaa gccaggagcu gccuggacag guacguugg      7020 cauuguuaca augcucucuc caauguugca ccacuggauc aaagucgaau auggcaaccu    7080
gucucugucu ggaauagccc agucagccuc aguccuuucu uucauggaca aggggauacc    7140
auucaugaag augaauaucu cggucauaau gcugcugguc aguggcugga auucaauaac    7200
agugaugccu cugcucugug gcauagggug cgccaugcuc cacggucuc ucauuuuacc     7260 uggaaucaaa gcgcagcagu caaagcuugc acagagaagg guguuccaug gcguugccga    7320
gaacccugug guugauggga auccaacagu ugacauugag gaagcuccug aaaugccugc    7380
ccuuuaugag aagaaacugg cucuauaucu ccuucuugcu cucagccuag cuucuguugc    7440
caugugcaga acgcccuuuu cauuggcuga aggcauuguc cuagcaucag cugccuuagg    7500
gccgcucaua gagggaaaca ccagccuucu uggaauggga cccauggcug ucuccaugac    7560
aggagucaug aggggggaauc acuaugcuuu gugggaguc auguacaauc uaggaagau     7620 gaaaacugga cgccggggga gcgcgaaugg aaaaacuuug ggugaagucu ggaagaggga    7680
acugaaucug uuggacaagc gacaguuuga guuguauaaa aggaccgaca uugugaggu     7740 ggaucgugau acgcacgca ggcauuuggc cgaaggaag guggacaccg ggguggcggu      7800 cuccagggg accgcaaagu uaaggugguu ccaugagcgu ggcuaugca agcuggaagg      7860 uaggugauu gaccggggu guggccgcgg aggcuggugu uacuacgcug cugcgcaaaa      7920
ggaagugagu ggggucaaag gauuuacucu uggaagagac ggccaugaga acccaugaa     7980 ugugcaaagu cugggaugga acaucaucac cuucaaggaa aaaacugaua uccaccgccu    8040
agaaccagug aaaugugaca cccuuuugug ugacauugga gagucaucau cgucaucggu    8100 cacagaggg gaaaggaccg ugagaguucu ugauacugua gaaaaauggc uggcuugugg     8160
gguugacaac uucguguga aggguuagc uccauacaug ccagauguuc ucgagaaacu      8220
ggaauugcuc caaaggaggu uuggcggaac agugaucagg aacccucucu ccaggaauuc    8280
cacucaugaa auguacuacg ugucuggagc ccgcagcaau gucacauuua cugugaacca    8340
aacaucccgc cuccgauga ggagaauga gcgucccaacu ggaaaaguga cccuggagc      8400 ugacgucauc cucccaauug ggacacgcag uguugagaca gacaagggac cccuggacaa    8460
agaggccaua gaagaaggg uugagaggau aaaucgag uacaugaccu cuugguuua       8520 ugacaaugac aaccccuaca ggaccuggca cuacugggc uccaugca caaaaaccuc       8580 aggaagugcg gcgagcaugg uaaaugugu uauuaaaauu cugacauauc caugggacag    8640
gauagaggag gucacaagaa uggcaaugac ugacacaacc cccuuuggac agcaaagagu    8700
guuuaaagaa aaaguugaca ccagagcaaa ggauccacca gcgggaacua ggaagaucau    8760
gaaaguuguc aacaggugc uguuccgcca ccuggccaga gaaaagaacc ccagacugug    8820
cacaaaggaa gaauuauug caaaaguccg aagucaugca gccauggag cuuaccggga      8880 agaacaagaa caguggaaga cugccaauga ggcuguccaa gacccaaagu ucugggaacu    8940
```

-continued

```
gguggaugaa gaaaggaagc ugcaccaaca aggcaggugu cggacuugug uguacaacau      9000 gaugggaaa agagagaaga agcugucaga guuuggaaa gcaaagggaa gccgugccau        9060
augguauaug uggcugggag cgcgguaucu ugaguuugag gcccugggau uccugaauga      9120
ggaccauugg gcuuccaggg aaaacucagg aggaggagug gaaggcauug gcuuacaaua      9180
ccuaggauau gugaucagag accuggcugc aauggauggu ggguggauucu acgcggauga    9240 caccgcugga ugggacacgc gcaucacaga ggcagaccuu gaugaugaac aggagaucuu     9300
gaacuacaug agcccacauc acaaaaaacu ggcacaagca gugauggaaa ugacauacaa     9360
gaacaaagug gugaaagugu ugagaccagc cccaggaggg aaagccuaca uggaugucau     9420
aagucgacga gaccagagag gauccgggca gguagugacu uaugcucuga acaccaucac    9480
caacuugaaa guccaauuga ucagaauggc agaagcagag augguagauac auccaccaaca   9540 uguucaagau gugaugaauu caguucugac caggcuggag gcauggcuca cugagcacgg    9600
augugacaga cugaagagga uggcggugag uggagacgac ugugugggucc ggcccaucga   9660 ugacagguuc ggccuggccc ugucccaucu caacgccaug uccaagguua aaaggacau     9720 aucugaaugg cagccaucaa aagggguggaa ugauugggga aaugugcccu ucuguucccca  9780 ccacuuccau gaacuacagc ugaaggaugg caggaggauu guggugccuu gccgagaaca    9840
ggacgagcuc auugggagag aaggggguguc uccaggaaac ggcuggauga ucaaggaaac   9900
agcuugccuc agcaaagccu augccaacau gguucacug auguauuuuc acaaaaggga     9960
caugaggcua cugucauugg cuguuuccuc agcuguuccc accucauggg uuccacaagg    10020
acgcacaaca uggucgauuc augggaaagg ggaguggaug accacggaag acaugcuuga    10080 ggugggaac agaguaugga uaaccaacaa cccacacaug caggacaaga caauggugaa     10140 aaauggaga gaugucccuu aucuaaccaa gagacaagac aagcugugcg gaucacugau    10200
uggaaugacc aauagggcca ccugggcccuc ccacauccau uuagucaucc aucguauccg   10260
aacgcugauu ggacaggaga aauacacuga cuaccuaaca gucauggaca gguauucugu    10320
ggaugcugac cugcaacugg gugagcuuau cugaaacacc aucuaacagg aauaaccggg    10380
auacaaacca cgggugggaga accggacucc ccacaaccug aaaccgggau auaaaccacg    10440
gcuggagaac cgggcuccgc acuuaaaaug aaacagaaac cgggauaaaa acuacggaug    10500
gagaaccgga cuccacacau ugagacagaa gaaguguca gcccagaacc ccacacgagu    10560
uuugccacug cuaagcugug aggcagugca ggcugggaca gccgaccucc agguugcgaa   10620
aaaccugguu ucuggggaccu cccacccag aguaaaaaga acggagccuc cgcuaccacc    10680
cucccacgug gugguagaaa gacggggucu agagguuaga ggagacccuc cagggaacaa    10740
auagugggac cauauugacg ccagggaaag accggagugg uucucugcuu uccuccaga    10800 ggucugugag cacaguuugc ucaagaauaa gcagaccuuu ggaugacaaa cacaaaacca   10860
cu                                                                  10862
```

<210> SEQ ID NO 2
<211> LENGTH: 10862
<212> TYPE: RNA
<213> ORGANISM: Yellow fever virus
<220> FEATURE:
<221> NAME/KEY: misc_feature
<223> OTHER INFORMATION: RNA sequence of the YFV YF-Vax. strain

<400> SEQUENCE: 2
aguaaauccu gugugcuaau ugaggugcau uggucugcaa aucgaguugc uaggcaauaa       60

```
acacauuugg auuaauuuua aucguucguu gagcgauuag cagagaacug accagaacau      120
gucuggucgu aaagcucagg gaaaaacccu gggcgucaau augguacgac gaggaguucg      180
cuccuuguca aacaaaauaa aacaaaaaac aaaacaaauu ggaaacagac cuggaccuuc      240
aagaggyguu caaggauuua ucuuuuucuu uuuguucaac auuuugacug gaaaaaagau      300
```
(Note: replaced one above line mistake — see image.)

```
acacauuugg auuaauuuua aucguucguu gagcgauuag cagagaacug accagaacau      120
gucuggucgu aaagcucagg gaaaaacccu gggcgucaau augguacgac gaggaguucg      180
cuccuuguca aacaaaauaa aacaaaaaac aaaacaaauu ggaaacagac cuggaccuuc      240
aagaggyguu caaggauuua ucuuuuucuu uuuguucaac auuuugacug gaaaaaagau      300
cacagcccac cuaaagaggu gyuggaaaau gcuggaccca agacaaggcu uggcuguucu      360
aaggaaaguc aagagagugg uggccaguuu gaugagagga uuguccucaa ggaaacgccg      420
uucccaugau guucugacug ugcaauuccu aauuuuggga augcuguuga ugacgggugg      480
agugaccuug gugcggaaaa acagaugguu gcuccuaaau ugacaucug aggaccucgg      540
gaaaacauuc ucuggggca caggcaacug cacaacaaac auuuuggaag ccaaguacug      600
gugcccagac ucaauggaau acaacugucc caaucucagu ccaagagagg agccagauga      660
cauugauugc uggugcuaug ggguggaaaa cguuagaguc gcauauggua agugugacuc      720
agcaggcagg ucuaggaggu caagaagggc cauugacuug ccuacgcaug aaaaccaugg      780
uuugaagacc cggcaagaaa aauggaugac uggaagaaug ggugaaaggc aacuccaaaa      840
gauugagaga ugguucguga ggaacccccuu uuuugcagug acggcucuga ccauugccua      900
ccuugggga agcaacauga cgcaacgagu cgugauugcc cuacggucu uggcuguugg      960
uccggccuac ucagcucacu gcauuggaau uacugacagg gauuucauug aggggugca     1020
uggaggaacu ugggunucag cuacccugga gcaagacaag ugugucacug uuauggcccc     1080
ugacaagccu ucauuggaca cucucacuaga gacaguagcc auugauagac cugcugaggu     1140
gaggaaagug uguuacaaug caguucucac ucaugugaag auuaaugaca gugccccag      1200
cacuggagag gcccaccuag cugaagagaa cgaaggggac aaugcgugca agcgcacuua     1260
uucugauaga ggcugggca auggcugugg ccuauuuggg aaagggagca uuguggcaug     1320
cgccaaauuc acuugugcca aauccaugag uuuguuugag guuugaucaga ccaaaauuca     1380
guaugucauc agagcacaau ugcauguagg ggccaagcag gaaaauugga cuaccgacau     1440
uaagacucuc aaguuugaug cccugucagg cucccaggaa gucgaguuca uuggguaugg     1500
aaaagcuaca cuggaaugcc aggugcaaac ugcgguggac uuugguaaca guuacaucgc     1560
ugagauggaa acagagagcu ggauaguga cagacagugg gcccaggacu ugacccugcc     1620
auggcagagu ggaaguggcg ggugguggag agagaugcau caucuugucg aauuugaacc     1680
uccgcaugcc gccacuauca gaguacuggc ccugggaaac caggaaggcu ccuugaaaac     1740
agcucuuacu ggcgcaauga ggguuacaaa ggacacaaau gacaacaacc uuuacaaacu     1800
acauggugga caugnuucuu gcagagugaa auugucagcu uugacacuca agggggcauc     1860
cuacaaaaua ugcacugaca aaauguuuuu ugucaagaac ccaacugaca cuggccauugg     1920
cacuguugug augcagguga aagucaaa aggagccccc ugcaggauuc cagugauagu     1980
agcugaugau cuuacagcgg caaucaauaa aggcauuuug guuacaguua ccccaucgc     2040
cucaaccaau gauggaugaag ugcugauuga ggugaaaccca ccuuuuggag acagcuacau     2100
uaucguuggg agaggagauu cacgucucac uuaccaguggg cacaaagagg gaagcucaau     2160
aggaaaguug uucacucaga ccaugaaagg cguggaacgc cuggccguca ugggagacac     2220
cgccugggau ucagcucccg cuggaggguu cuucacuucg guugggaaag gaauucauac     2280
gguguuggc cucugccuuuc agggggcuauu uggcggcuug aacuggauaa caaaggucau     2340
caugggggcg guacuuauau ggguuggcau caacacaaga aacaugacaa uguccaugag     2400
```

-continued

```
caugaucuug guaggaguga ucaugauguu uuugucucua ggaguugggg cggaucaagg 2460
augcgccauc aacuuuggca agagagagcu caagugcgga gaugguaucu ucauauuuag 2520
agacucugau gacuggcuga acaaguacuc auacuaucca gaagauccug ugaagcuugc 2580
aucaauagug aaagccucuu uugaagaagg gaagugugge cuaaauucag uugacucccu 2640
ugagcaugag auguggagaa gcagggcaga ugagaucaau gccauuuuug aggaaaacga 2700
gguggacauu ucuguugucg ugcaggaucc aaagaauguu uaccagagag gaacucaucc 2760

auuuuccaga auucgggaug gucugcagua ugguuggaag acuuggggua agaaccuugu 2820
guucucccca gggaggaaga auggaagcuu caucauagau ggaaagucca ggaaagaaug 2880
cccguuuuca aaccgggucu ggaauucuuu ccagauagag gaguuuggga cgggagugu 2940
caccacacgc guguacaugg acgcagucuu ugaauacacc auagacugcg auggaucuau 3000
cuugggugca gcggugaacg gaaaaaagag ugcccauggc ucuccaacau uuuggauggg 3060
aagucaugaa guaaauggga cauggaugau ccacaccuug gaggcauuag auuacaagga 3120
gugugagugg ccacugacac auacgauugg aacaucaguu gaagagagug aaauguucau 3180
gccgagauca aucggaggcc caguuagcuc ucacaaucau aucccuggau acaagguuca 3240
gacgaacgga ccuuggaugc agguaccacu agaagugaag agagaagcuu gcccagggac 3300
uagcgugauc auugauggca acugugaugg acggggaaaa ucaaccagau ccaccacgga 3360
uagcgggaaa guuauuccug aauggugug ccgcuccugc acaaugccgc cugugagcuu 3420
ccaugguagu gaugggugu gguaucccau ggaaauuagg ccaaggaaaa cgcaugaaag 3480
ccaucuggug cgcuccuggg uuacagcugg agaaauacau gcugucccuu uugguuuggu 3540
gagcaugaug auagcaaugg aaguggucu aaggaaaaga cagggaccaa agcaaauguu 3600
gguuggagga guagugcucu ugggagcaau gcuggucggg caaguaacuc uccuugauuu 3660
gcugaaacuc acaguggcug ugggauugca uuuccaugag augaacaaug gaggagacgc 3720
cauguauaug gcguugauug cugccuuuuc aaucagacca gggcugcuca ucggcuuugg 3780
gcucaggacc cuauggagcc cucgggaacg ccuugugcug acccuaggag cagccauggu 3840
ggagauugcc uuggguggcg ugaugggcgg ccuguggaag uaucuaaaug caguuucucu 3900
cugcauccug acaauaaaug cuguugcuuc uaggaaagca ucaaauacca ucuugcccu 3960
cauggcucug uugacaccug ucacuauggc ugaggugaga cuugccgcaa uguucuuuug 4020
ugccguggu aucauagggg uccuucacca gaauuucaag gacaccucca ugcagaagac 4080
uauaccucug guggcccuca cacucacauc uuaccugggc uugacacaac cuuuuuuggg 4140
ccugugugca uuucuggcaa cccgcauauu ugggcgaagg aguaucccag ugaaugaggc 4200
acucgcagca gcuggucuag ugggagugcu ggcaggacug gcuuuucagg agauggagaa 4260
cuuccuuggu ccgauugcag uuggaggacu ccugaugaug cugguuagcg uggcugggag 4320
gguggauggg cuagagcuca agaagcuugg ugaaguuuca ugggaagagg aggcggagau 4380
cagcgggagu uccgcccgcu augaugugge acucagugaa caaggggagu ucaagcugcu 4440
uucugaagag aaagugccau gggaccaggu ugugaugacc ucgcuggccu ugguuggggc 4500
ugcccuccau ccauuugcuc uucugcuggu ccuugcuggg uggcuguuuc augucagggg 4560
agcuaggaga aguggggaug ucuuguggga uauucccacu ccuaagauca ucgaggaaug 4620
ugaacaucug gaggauggga uuuauggcau auuccaguca accuucuugg gggccuccca 4680
gcgaggagug ggaguggcac agggaggggu guuccacaca auguggcaug ucacaagagg 4740
agcuuuccuu gucaggaaug gcaagaaguu gauuccaucu ugggcuucag uaaaggaaga 4800
```

```
ccuugucgcc uaugguggcu cauggaaguu ggaaggcaga ugggauggag aggaagaggu    4860
ccaguugauc gcggcuguuc caggaaagaa cguggucaac guccagacaa aaccgagcuu    4920
guucaaagug aggauggggg gagaaaucgg ggcugucgcu cuugacuauc cgaguggcac    4980
uucaggaucu ccuauuguua acaggaacgg agaggugauu gggcuuacg gcaauggcau    5040 ccuugucggu gacaacuccu ucguguccgc cauaucccag acugagguga aggaagaagg    5100
aaaggaggag cuccaagaga ucccgacaau gcuaaagaaa ggaaugacaa cugcccuuga    5160
uuuucauccu ggagcuggga agacaagacg uuccuccca cagaucuugg ccgagugcgc    5220
acggagacgc uugcgcacuc uugucuuggc cccaccagg guuguucuuu cugaaaugaa    5280
ggaggcuuuu cacggccugg acgugaaauu ccacacacag gcuuuuccg cucacggcag    5340 cgggagagaa gucauugaug cuaugugcca ugccacccua acuuacagga uguuggaacc    5400
aacuaggguu guuacuggg aagugaucau uauggaugaa gcccauuuuu uggauccagc    5460
uagcauagcc gcuagagguu gggcagcgca cagagcuagg gcaaaugaaa gugcaacaau    5520
cuugaugaca gccacaccgc cugggacuag ugaugaauuu ccacaucaa augguguggaaau 5580 agaagauguu caaacggaca uacccaguga gcccuggaac acagggcaug acuggauccu    5640
ggcugacaaa aggcccacgg cauguuccu uccauccauc agagcugcaa augucauggc    5700
ugccucuuug cguaaggcug gaaagagugu gguguccug aacaggaaaa ccuugagag    5760 agaauacccc acgauaaagc agaagaaacc ugacuuuaua uuggccacug acauagcuga    5820
aaugggagcc aaccuuugcg uggagcgagu gcuggauugc aggacggcuu uuaagccugu    5880
gcuuguggau gaagggagga aggugguguggcaau aaaagggcca cucgauauucu ccgcaucccuc    5940 ugcugcucaa aggaggggc gcauugggag aaaucccaac agaauggag acucauacua    6000 cuauucugag ccuacaagug aaaauaaugc ccaccacguc ugcugguugg aggccucaau    6060
gcucuuggac aacaauggagg ugaggggugg aauggucgcc ccacucuaug gcguugaagg    6120
aacuaaaaca ccaguuuccc cugguguaaaau gagaucugagg gaugaccaga ggaaagucuu    6180
cagagaacua gugaggaauu gugaccugcc cguuuggcuu ucguggcaag uggccaaggc    6240
ugguuugaag acgaaugauc guaagugguggu uuuugaaggc ccugaggaac augagaucuu    6300
gaaugacagc ggugaaacag ugaagugcag ggcuccugga ggagcaaaga agccucugcg    6360 cccaagguggu ugugaugaaa gggugucauc ugaccagagu gcgcucugug aauuuauuuaa    6420 guuugcugaa gguaggaggg gagcugcuga agugcuaguu gugcugagug aacucccuga    6480
uuuccuggcu aaaaaggug gagaggcaau ggauaccauc agugguguuuc uccacucuga    6540 ggaaggcucu agggcuuacc gcaaugcacu aucaaugaug ccugaggcaa ugacaauagu    6600
caugcuguuu auacuggcug acuacugac aucgggaaug ucaucuuuu caugucucc    6660 caaaggcauc aguagaaugu cuaggcgau gggcacaaug gccggcugug gauaucucau    6720 guccuugga ggcgucaaac ccacucacau uccccauauc augcucauau ucuuugcccu    6780
gauguggguu gugaucccecg agccagggca acaaaggucc auccaagaca accaaguggc    6840 auaccecauu auuggcaucc ugacgcgguu ucagccggug gcagccaacg agcuaggcau    6900
gcuggagaaa accaaagagg acccucuugg gaagaagaac uuaauccau cuagugcuuc    6960 acccggggagu uggccggauc uugaccugaa gccaggagcu gccuggacag uguacguugg    7020
cauuguuaca augcucucuc caaguuugca ccacuggauc aaagucgaau auggcaaccu    7080
gucucugucu ggaauagccc agucagccuc aguccuuucu uucauggaca agggggauacc    7140
```

```
auucaugaag augaauaucu cggucauaau gcugcugguc aguggcugga auucaauaac   7200
agugaugccu cugcucugug gcauagggug cgccaugcuc cacugucuc ucauuuuacc   7260 uggaaucaaa gcgcagcagu caaagcuugc acagagaagg guguuccaug gcguugccaa   7320
gaacccugug guugauggga auccaacagu ugacauugag gaagcuccug aaaugccugc   7380
ccuuuaugag aagaaacugg cucuauaucu ccuucuugcu cucagccuag cuucuguugc   7440
caugugcaga acgcccuuuu cauuggcuga aggcauugc cuagcaucag cugcccuagg    7500
gccgcucaua gagggaaaca ccagccuucu uuggaaugga cccauggcug ucuccaugac   7560
aggagucaug agggggaauc acuaugcuuu ugugggaguc auguacaauc uauggaagau   7620
gaaaacugga cgccggggga gcgcgaaugg aaaaacuuug ggugaagucu ggaagaggga   7680
acugaaucug uuggacaagc gacaguuuga guuguauaaa aggaccgaca uuguggaggu   7740
ggaucgugau acggcacgca ggcauuuggc cgaagggaag guggacaccg gguggcggu    7800 cuccaggggg accgcaaagu uaaggugguu ccaugagcgu ggcuaugca agcuggaagg    7860 uagggugauu gaccugggu guggccgcgg aggcuggugu uacuacgcug cugcgcaaaa    7920
ggaagugagu gggucaaag gauuuacucu uggaagagac ggccaugaga aacccaugaa    7980
ugugcaaagu cugggaugga acaucaucac cuucaaggac aaaacugaua uccaccgccu   8040
agaaccagug aaaugugaca cccuuuugug ugacauugga gagucaucau cgucaucggu   8100
cacagagggg gaaaggaccg ugagaguucu ugauacugua gaaaaauggc uggcuugugg   8160
gguugacaac uucugugugga gguguuagc uccauacaug ccagauguuc ucgagaaacu   8220
ggaauugcuc caaaggaggu uggcggaac agugaucagg aacccucucu ccaggaauuc    8280
cacucaugaa auguacuacg ugucuggagc ccgcagcaau gucacauuua cugugaacca   8340
aacaucccgc cuccugauga ggagaauga gcguccaacu ggaaaaguga cccuggaggc    8400
ugacgucauc cucccaauug ggacacgcag uguugagaca gacaagggac cccuggacaa   8460
agaggccaua aagaaaggg uugagaggau aaaaucugag uacaugaccu cuugguuua    8520 ugacaaugac aaccccuaca ggaccuggca cuacugggc uccuauguca caaaaccuc   8580 aggaagugcg gcgagcaugg uaaauggugu uauuaaaau cugacauauc caugggacag   8640
gauagaggag gucacaagaa uggcaaugac ugacacaacc ccuuuuggac agcaaagagu   8700
guuuaaagaa aaaguugaca ccagagcaaa ggauccacca gcgggaacua ggaagaucau   8760
gaaaguuguc aacaggugc uguuccgcca ccuggccaga gaaaagaacc ccagacugug    8820
cacaaaggaa gaauuuaug caaaaguccg aagucaugca gccauggag cuuaccgga    8880 agaacaagaa caguggaaga cugccaauga ggcugguccaa gacccaaagu ucugggaacu   8940 ggugaugaa gaaaggaagc ugcaccaaca aggcaggugu cggacuugug uacaaacau    9000 gauggggaaa agagagaaga agcugucaga guuugggaaa gcaagggaa gccgugccau    9060 augguauaug uggcugggag cgcgguaucu ugaguuugag gcccugggau uccgaaauga   9120
ggaccauugg gcuccaggg aaaacucagg aggagagug gaaggcauug gcuuacaaua    9180
ccuaggauau gugaucagag accuggcugc aauggaugu ggugauucu acgcggauga    9240 caccgcugga uggacacgc gcaucacaga ggcagaccuu gaugaugaac aggagaucuu   9300
gaacuacaug agcccacauc acaaaaacu ggcacaagca gugauggaaa ugacauacaa   9360
gaacaaagug gugaagugu ugagaccagc cccaggaggg aaagccuaca uggaugucaa    9420
aagucgacga gaccagagag gauccgggca gguagugacu uaugcucuga acaccauac    9480 caacuugaaa guccaauuga ucagaauggc agaagcagag augguagauac aucaccaaca   9540
```

```
uguucaagau ugugaugaau caguucugac caggcuggag gcauggcuca cugagcacgg      9600
auguaacaga cugaagagga uggcggugag uggagacgac ugugguggucc ggcccaucga     9660 ugacagguuc ggccuggccc ugucccaucu caacgccaug uccaagguua gaaaggacau      9720
aucugaaugg cagccaucaa aagggguggaa ugauugggga aaugcccuu ucuguuccca      9780 ccacuuccau gaacuacagc ugaaggaugg caggaggauu ggugugccuu gccgagaaca      9840
ggacgagcuc auugggagag aagggugguc uccaggaaac ggcuggauga ucaaggaaac      9900
agcuugccuc agcaaagccu augccaacau ggucacug auguauuuuc acaaaaggga       9960
caugaggcua cugucauugg cuguuuccuc agcuguuccc accucauggg uuccacaagg     10020
acgcacaaca uggucgauuc auggaaagg ggaguggaug accacggaag acaugcuuga     10080 ggugugggaac agaguaugga uaaccaacaa cccacacaug caggacaaga caauggugaa    10140
aaaauggaga gaugucccuu aucuaaccaa gagacaagac aagcugugcg gaucacugau    10200
uggaaugacc aauagggcca ccugggccuc ccacauccau uggucauucc aucguauccg    10260
aacgcugauu ggacaggaga aauacacuga cuaccuaaca gucauggaca gguauucugu    10320
ggaugcugac cugcaacugg gugagcuuau cugaaacacc aucuaacagg aauaaccggg    10380 auacaaaacca cgguguggaga accggacucc ccacaaccug aaaccgggau auaaaccacg   10440
gcuggagaac cggacuccgc acuuaaaaug aaacagaaac cgggauaaa acuacggau       10500 gagaaccgga cuccacacau ugagacagaa gaaguuguca gcccagaacc ccacacgagu    10560
uuugccacug cuaagcugug aggcagugca ggcuggaca gccgaccucc agguugcgaa     10620 aaaccuggu ucggggaccu cccacccccag aguaaaaaga acggagccuc cgcuaccacc     10680
cucccacgug gguguagaaa gacggggucu agagguuaga ggagaccccuc cagggaacaa    10740 auagugggac cauauugacg ccagggaaag accggagugg uucucugcuu uccuccaga     10800 ggucugugag cacaguuugc ucaagaauaa gcagaccuuu ggaugacaaa cacaaaacca     10860
cu                                                                   10862
```

<210> SEQ ID NO 3
<211> LENGTH: 10862
<212> TYPE: RNA
<213> ORGANISM: Yellow fever virus
<220> FEATURE:
<221> NAME/KEY: misc_feature
<223> OTHER INFORMATION: RNA sequence of the YFV Stamaril. strain

<400> SEQUENCE: 3

```
aguaaauccu gugugcuaau ugaggugcau uggucugcaa aucgaguugc uaggcaauaa       60
acacauuugg auuaauuuua aucguucguu gagcgauuag cagagaacug accagaacau      120
gucuggucgu aaagcucagg gaaaaacccu gggcgucaau augguacgac gaggaguucg      180
cuccuuguca aacaaaauaa aacaaaaaac aaaacaaauu ggaaacagac cuggaccuuc      240 aagaggguguu caaggauuua ucuuuuucuu uuuguucaac auuuugacug aaaaaagau      300 cacagcccac cuaaagaggu gugaaaau gcuggaccca agacaaggcu uggcuguucu       360 aaggaaaaguc aagagagugg uggcaguuu gaugagagga uuguccucaa ggaaacgccg     420
uucccaugau guucugacug ugcaauuccu aauuugggga augcuguuga ugacgggugg    480
agugaccuug guguggaaaa acagauggu gcuccaaaau gugacaucug aggaccucgg     540
gaaaacauuc ucuguggggca caggcaacug cacaacaaac auuuuggaag ccaaguacug    600
gugcccagac ucaauggaau acaacugucc caaucucagu ccaagagagg agccagauga    660
```

-continued

```
cauugauugc uggugcuaug ggguggaaaa cguuagaguc gcauauggua agugugacuc      720
agcaggcagg ucuaggaggu caagaagggc cauugacuug ccuacgcaug aaaaccaugg      780
uuugaagacc cggcaagaaa aauggaugac uggaagaaug ggugaaaggc aacuccaaaa      840
gauugagaga ugguucguga ggaaccccuu uuuugcagug acggcucuga ccauugccua      900
ccuuguggga agcaacauga cgcaacgagu cgugauugcc cuacuggucu ggcuguugg       960 uccggccuac ucagcucacu gcauggaauu acugacagg gauucauug aggggugca       1020 uggaggaacu uggguuucag cuacccugga gcaagacaag ugugucacug uuauggcccc     1080
ugacaagccu ucauuggaca ucucacuaga gacaguagcc auugauagac cugcugaggu     1140
gaggaaagug uguuacaaug caguucucac ucaugugaag auuaaugaca gugccccag      1200 cacuggagag gcccaccuag cugaagagaa cgaaggggac aaugcgugca agcgcacuua     1260
uucugauaga ggcuggggca auggcugugg ccauuuggg aaagggagca uguggcaug      1320 cgccaaauuc acuugugcca aaccaugag uuuguugag guugaucaga ccaaaauuca      1380
guaugucauc agagcacaau ugcauguagg ggccaagcag aaaauugga uaccgacau      1440 uaagacucuc aaguuugaug cccugucagg ucccaggaa gucgaguuca uuggguaugg     1500
aaaagcuaca cuggaaugcc aggugcaaac ugcgguggac uuugguaaca guuacaucgc     1560
ugagauggaa acagagagcu ggauaggga cagacagugg gcccaggacu ugacccugcc      1620
auggcagagu ggaaguggcg gggugaggag agagaugcau caucuugucg aauuugaacc    1680
uccgcaugcc gccacuauca gaguacuggc ccugggaaac caggaaggcu ccuugaaaac    1740
agcucuuacu ggcgcaauga ggguuacaaa ggacacaaau gacaacaacc uuuacaaacu    1800
acauggugga cauguuucuu gcagagagaa auugucagcu uugacacuca agggacauc     1860 cuacaaaaua ugcacugaca aaauguuuuu ugucaagaac ccaacugaca cuggccaugg    1920
cacuguugug augcaggaga aagugucaaa aggagccccc ugcaggauuc agugauagu     1980 agcugaugau cuuacagcgg caaucaauaa aggcauuuug guuacaguua ccccaucgc     2040 cucaaccaau gaugaugaag ugcugauuga ggugaaccca ccuuuuggag acagcuacau    2100
uaucguuggg agaggagauu cacgucucac uuaccagugg cacaaagagg gaagcucaau    2160
aggaaaguug uucacucaga ccaugaaagg cguggaacgc cuggccguca ugggagacac    2220
cgccugggau uucagcuccg cuggagggu uucacuucg guugggaaag gaauucauac    2280 gguguuggc ucugccuuuc aggggcuauu uggcggcuug aacuggauaa caaaggucau    2340 cauggggcg guacuuauau ggguuggcau caacacaaga aacaugacaa uguccaugag    2400
caugaucuug guaggaguga ucaugauguu uuugucucua ggaguugggg cggaucaagg    2460
augcgccauc aacuuuggca agagagagcu caagugcgga gaugguaucu ucauauuuag    2520
agacucugau gacuggcuga caaguacuc auacuauucca gaagauccug ugaagcuugc    2580
aucaauagag aaagcucucu uugaagaagg gaagugugg cuaaauucag uugacucccu    2640
ugagcaugag auguggagaa gcagggcaga ugagaucaau gccauuuuug aggaaaacga    2700 ggggacauu ucguugucg ugcaggaucc aaagaauguu uaccagagag gaacucaucc     2760 auuuccaga auucgggaug ucucagcagua ugguggaag acuggggua agaaccuugu    2820 guucuccca gggaggaaga auggaagcuu caucauagau ggaaagucca ggaaagaaug    2880
cccguuuuca aaccggggucu ggaauucuuu ccagauagag gaguuuggga cgggagugu    2940 caccacacgc guguacaugg acgcagucuu ugaauacacc auagacugcg auggaucuau    3000
```

-continued

| | | | | | |
|---|---|---|---|---|---|
| cuuggguṣca | gcggugaacg | gaaaaaagag | ugcccauggc | ucuccaacau | uuuggaugggg | 3060 |
| aagucaugaa | guaaaugggga | cauggaugau | ccacaccuug | gaggcauuag | auuacaagga | 3120 |
| gugugagugg | ccacugacac | auacgauugg | aacaucaguu | gaagagagug | aaauguucau | 3180 |
| gccgagauca | aucggaggcc | caguuagcuc | ucacaaucau | aucccuggau | acaagguuca | 3240 |
| gacgaacgga | ccuuggaugc | agguaccacu | agaagugaag | agagaagcuu | gcccagggac | 3300 |
| uagcgugauc | auugauggca | acugugaugg | acggggaaaa | ucaaccagau | ccaccacgga | 3360 |
| uagcgggaaa | guuauuccug | aauggguguu | ccgcuccugc | acaaugccgc | cugugagcuu | 3420 |
| ccauggauagu | gaugggguguu | gguaucccau | ggaaauuagg | ccaaggaaaaa | cgcaugaaag | 3480 |
| ccaucuggug | cgcuccuggg | uuacagcugg | agaaauacau | gcuguccuu | uugguuuggu | 3540 |
| gagcaugaug | auagcaaugg | aagugguccu | aaggaaaaga | cagggaccaa | agcaaaauguu | 3600 |
| gguuggagga | guagugcucu | ugggagcaau | gcuggucggg | caaguaacuc | uccuugauuu | 3660 |
| gcugaaacuc | acaguggcug | ugggauugca | uuuccaugag | augaacaaug | gaggagacgc | 3720 |
| cauguauaug | gcguugauug | cugccuuuuc | aaucagacca | gggcugcuca | ucggcuuugg | 3780 |
| gcucaggacc | cuauggagcc | cucgggaacg | ccuugugcug | acccuaggag | cagccauggu | 3840 |
| ggagauugcc | uuggguggcg | ugaugggcgg | ccugugggaag | uaucuaaaug | caguucucu | 3900 |
| cugcauccug | acaauaaaug | cuguugcuuc | uaggaaagca | ucaaauacca | ucuugcccu | 3960 |
| cauggcucug | uugacaccug | ucacuauggc | ugagguuagaa | cuugccgcaa | uguucuuug | 4020 |
| ugccgugguu | aucauagggg | uccuucacca | gaacuucaag | gacaccucca | ugcagaagac | 4080 |
| uauaccucug | guggcccuca | cacucacauc | uuaccugggc | uugacacaac | cuuuuuuggg | 4140 |
| ccugugugca | uuucuggcaa | cccgcauauu | ugggcgaagg | aguaucccag | ugaaugaggc | 4200 |
| acucgcagca | gcggucuag | ugggagugcu | ggcaggacug | gcuuucagg | agauggagaa | 4260 |
| cuuccuuggu | ccgauugcag | uuggaggacu | ccugaugaug | cugguuagcg | uggcugggag | 4320 |
| ggugauggg | cuagagcuca | agaagcuugg | ugaaguuuca | ugggaagagg | aggcggagau | 4380 |
| cagcgggagu | uccgcccgcu | augaugggc | acucagugaa | caagggagu | caagcugcu | 4440 |
| uucugaagag | aaaagugccau | gggaccaggu | ugugaugacc | ucgcuggccu | ugguuggggc | 4500 |
| ugccccuccau | ccauuugcuc | uucugcuggu | ccuugcuggg | uggcuguuuc | augucagggg | 4560 |
| agcuaggaga | aguggggaug | ucuuguggga | uauucccacu | ccuaagauca | ucgaggaaug | 4620 |
| ugaacaucug | gaggauggga | uuuauggcau | auuccaguca | accuucuugg | gggccuccca | 4680 |
| gcgaggagug | ggaguggcac | agggaggggu | guuccacaca | auguggcaug | ucacaagagg | 4740 |
| agcuuuccuu | gucaggaaug | gcaagaaguu | gauuccaucu | ugggcuucag | uaaaggaaga | 4800 |
| ccuugucgcc | uauggugguc | uauggaaguu | ggaaggcaga | ugggauggag | aggaagaggu | 4860 |
| ccaguugauc | gcggcuguuc | caggaaagaa | cguggucaac | guccagacaa | aaccgagcuu | 4920 |
| guucaaagug | aggaaugggg | gagaaaucgg | ggcugucgcu | cuugacuauc | cgagugcac | 4980 |
| uucaggaucu | ccuauuguua | acaggaacgg | agaggugauu | gggcuguacg | gcaauggcau | 5040 |
| ccuugucggu | gacaacuccu | ucgugccgc | cauauccag | acugaggguga | aggaagaagg | 5100 |
| aaaggaggag | cuccaagaga | ucccgacaau | gcuaaagaaa | ggaaugacaa | cuguccuuga | 5160 |
| uuuucauccu | ggagcuggga | agacaagacg | uuuccuccca | cagaucuugg | ccgagugcgc | 5220 |
| acgagacgc | uugcgcacuc | uuguguuggc | ccccaccagg | guuguucuuu | cugaaaugaa | 5280 |
| ggaggcuuuu | cacggccugg | acgugaaauu | ccacacacag | gcuuuuccg | cucacggcag | 5340 |
| cgggagagaa | gucauugaug | ccaugugcca | ugccacccua | acuuacagga | guuggaacc | 5400 |

```
aacuagggu  guuaacuggg  aagugaucau  uauggaugaa  gcccauuuuu  uggauccagc    5460
uagcauagcc  gcuagaggu  gggcagcgca  cagagcuagg  gcaaaugaaa  gugcaacaau    5520
cuugaugaca  gccacaccgc  cugggacuag  ugaugaauuu  ccacauucaa  auggugaaau    5580
agaagauguu  caaacggaca  uaccaguga  gcccuggaac  acagggcaug  acuggauccu    5640
ggcugacaaa  aggcccacgg  cauguuccu  uccauccauc  agagcugcaa  augucauggc    5700
ugccucuuug  cguaaggcug  gaaagagugu  gguggauccug  aacaggaaaa  ccuuugagag    5760
agaauacccc  acgauaaagc  agaagaaacc  ugacuuuaua  uuggccacug  acauagcuga    5820
aaugggagcc  aaccuuugcg  uggagcgagu  gcuggauugc  aggacggcuu  uuaagccugu    5880
gcuuguggau  gaagggagga  agguggcaau  aaaagggcca  cuucguaucu  ccgcauccuc    5940
ugcugcucaa  aggaggggc  gcauugggag  aaaucccaac  agagauggag  acucauacua    6000
cuauucugag  ccuacaagug  aaaauaaugc  ccaccacguc  ugcugguugg  aggccucaau    6060
gcucuuugac  aacauggagg  ugagggguggu  aauggucgcc  ccacucuaug  gcguugaagg    6120
aacuaaaaca  ccaguuuccc  cuggugaaau  gagacugagg  gaugaccaga  ggaaagucuu    6180
cagagaacua  gugaggaauu  gugaccugcc  cguuuggcuu  ucguggcaag  uggccaaggc    6240
ugguuugaag  acgaaugauc  guaaguggug  uuuugaaggc  ccugaggaac  augagaucuu    6300
gaaugacagc  ggugaaacag  ugaagugcag  ggcccuccugga  ggagcaaaga  agccucugcg    6360
cccaaggugg  ugugaugaaa  gggugucauc  ugaccagagu  gcgcugucug  aauuuauuaa    6420
guuugcugaa  gguaggaggg  gagcugcuga  agucuaguu  gugcugagug  aaccccuga     6480 uuccugggcu  aaaaaaggug  gagaggcaau  ggauaccauc  agugguguuuc  uccacucuga    6540 ggaaggcucu  agggcuuacc  gcaaugcacu  aucaaugaug  ccugaggcaa  ugacaauagu    6600
caugcuguuu  uacuggcug  gacuacugac  aucgggaaug  gucaucuuuu  ucaugucucc    6660
caaaggcauc  aguagaaugu  cuauggcgau  gggcacaaug  gccggcgugu  gauaucucau    6720
guuccuugga  ggcgucaaac  ccacucacau  cuccauauauc  augcucauau  ucuuugaccu    6780
gauggugguu  ugauccccg  agccagggca  acaaaggucc  auccaagaca  accaaguggc    6840
auaccucauu  auuggcaucc  ugacgcuggu  ucagcggug  gcagccaacg  agcuaggcau    6900
gcuggagaaa  accaaagagg  accucuuugg  gaagaagaac  uuaauuccau  cuagugcuuc    6960 accccuggagu  uggccggauc  uugaccgaa  gccaggagcu  gccuggacag  uguacguugg    7020
cauuguuaca  augcucucuc  caauguugca  ccacuggauc  aaagucgaau  auggcaaccu    7080
gucucugucu  ggaauagccc  agucagccuc  aguccuuucu  uucauggaca  aggggauacc    7140
auucaugaag  augaauaucu  cggucauaau  gcugcugguc  aguggcugga  auucaauaac    7200
agugaugccu  cugcucugug  gcauagggug  cgccaugcuc  cacugucuc  ucauuuuacc    7260 uggaaucaaa  gcgcagcagu  caaagcuugc  acagagaagg  guguuccaug  gcguugccaa    7320
gaacccugug  guugauggga  auccaacagu  ugacauugag  gaagcuccug  aaaugccugc    7380
ccuuuaugag  aagaaacugg  cucuauaucu  ccuucuugcu  cucagccuag  cuucuguugc    7440
caugugcaga  acgcccuuuu  cauuggcuga  aggcauugc  cuagcaucag  cugccuuagg    7500
gccgcucaua  gagggaaaca  ccagccucu  uggaauggga  cccauggcug  ucuccaugac    7560
aggagucaug  aggggggaauc  acuaugcuuu  uguggggaguc  auguacaauuc  uauggaagau    7620 gaaaacugga  cgccgggga  gcgcgaaugg  aaaaacuuug  ggugaagucu  ggaagaggga    7680
acugaaucug  uuggacaagc  gacaguuuga  guuguauaaa  aggaccgaca  uuguggagu     7740
```

```
ggaucgugau  acggcacgca  ggcauuuggc  cgaagggaag  gggacaccg   ggguggcggu   7800 cuccagggg   accgcaaagu  uaaggugguu  ccaugagcgu  ggcuauguca  agcuggaagg   7860
uagggugauu  gaccuggggu  guggccgcgg  aggcuggugu  uacuacgcug  cugcgcaaaa   7920
ggaagugagu  gggucaaag   gauuuacucu  uggaagagac  ggccaugaga  aacccaugaa   7980
ugugcaaagu  cugggaugga  acaucaucac  cuucaaggac  aaaacugaua  uccaccgccu   8040
agaaccagug  aaaugugaca  cccuuuugu   ugacauugga  gagucaucau  cgucaucggu   8100
cacagagggg  gaaaggaccg  ugagaguucu  ugauacugua  gaaaaauggc  uggcuugugg   8160
gguugacaac  uucugugug   aggguuuagc  uccauacaug  ccagauguuc  ucgagaaacu   8220
ggaauugcuc  caaggaggu   uggcggaac   agugaucagg  aacccucucu  ccaggaauuc   8280
cacucaugaa  auguacuacg  ugucuggagc  ccgcagcaau  gucacauuua  cugugaacca   8340
aacaucccgc  cuccugauga  ggagaaugag  gcguccaacu  ggaaagugga  cccuggaggc   8400
ugacgucauc  cucccaauug  ggacacgcag  uguugagaca  gacaagggac  cccuggacaa   8460
agaggccaua  gaagaaaggg  uugagaggau  aaaaucugag  uacaugaccu  cuugguuuua   8520
ugacaaugac  aaccccuaca  ggaccuggca  cuacugugc   uccuauguca  caaaaaccuc   8580
aggaagugcg  gcgagcaugg  uaaauggugu  uauuaaaauu  cugacauauc  caugggacag   8640
gauagaggag  gucacaagaa  uggcaaugac  ugacaaacc   ccuuuuggac  agcaaagagu   8700
guuuaaagaa  aaaguugaca  ccagagcaaa  ggauccacca  gcgggaacua  ggaagaucau   8760
gaaaguuguc  aacaggugge  uguuccgcca  ccuggccaga  gaaaagaacc  ccagacugug   8820
cacaaaggaa  gaauuuauug  caaaaguccg  aagucaugca  gccauggaga  cuuaccugga   8880
agaacaagaa  caguggaaga  cugccaauga  ggcuguccaa  gacccaaagu  ucugggaacu   8940
gguggaugaa  gaaaggaagc  ugcaccaaca  aggcagugu   cggacuugug  uguacaacau   9000 gaugggaaa   agagaagaa   agcugucaga  guugggaaa   gcaaagggaa  gccgugccau   9060
augguauaug  uggcugggag  cgcgguaucu  ugaguuugag  gcccugggau  uccugaauga   9120
ggaccauugg  gcuuccaggg  aaaacucagg  aggaggagug  gaaggcauug  gcuuacaaua   9180
ccuaggauau  gugaucagag  accuggcgc   aauggauggu  ggggauucu   acgcggauga   9240 caccgcugga  ugggacacgc  gcaucacaga  ggcagaccuu  gaugaugaac  aggagaucuu   9300
gaacuacaug  agcccacauc  acaaaaaacu  ggcacaagca  gugauggaaa  ugacauacaa   9360
gaacaaagug  gugaaagugu  ugagaccagc  cccaggaggg  aaagccuaca  uggaugucau   9420
aagucgacga  gaccagagag  gauccgggca  gguagacu    uaugcucuga  acaccaucac   9480
caacuugaaa  guccaauuga  ucagaauggc  agaagcagag  auggugauac  aucaccaaca   9540
uguucaagau  ugugaugaau  caguucgac   caggcuggag  gcauggcuca  cugagcacgg   9600
auguaacaga  cugaagagga  uggcgguga   uggagacgac  ugugguggcc  ggcccaucga   9660
ugacagguuc  ggccuggccc  ugucccaucu  caacgccaug  uccaagguua  aaaggacau   9720 aucugaaugg  cagccaucaa  aaggguggaa  ugauggag    aaugugcccu  ucuguuccca   9780
ccacuuccau  gaacuacagc  ugaaggaugg  caggaggauu  guggugccuu  gccgagaaca   9840
ggacgagcuc  auuggagag   aagggguc    uccaggaaac  ggcuggauga  ucaaggaaac   9900
agcuugccuc  agcaaagccu  augccaacau  ggggucacug  auguauuuuc  acaaaaggga   9960
caugaggcua  cugucauugg  cuguuuccuc  agcuguuccc  accucauggg  uuccacaagg   10020
acgcacaaca  uggucgauuc  augggaaagg  ggaguggaug  accacggaag  acaugcuuga   10080 ggugggaac   agaguaugga  uaaccaacaa  cccacacaug  caggacaaga  caauggugaa   10140
```

```
aaaauggaga gaugucccuu aucuaaccaa gagacaagac aagcugugcg gaucacugau    10200
uggaaugacc aauagggcca ccugggccuc ccacauccau uggucaucc aucguauccg     10260 aacgcugauu ggacaggaga aauacacuga cuaccuaaca gucauggaca gguauucugu    10320
ggaugcugac cugcaacugg gugagcuuau cugaaacacc aucuaacagg aauaaccggg    10380
auacaaacca cggguggaga accggacucc ccacaaccug aaaccgggau auaaaccacg    10440
gcuggagaac cggacuccgc acuuaaaaug aaacagaaac cgggauaaaa acuacggaug    10500
gagaaccgga cuccacacau ugagacagaa gaaguuguca gcccagaacc cacacgagu     10560 uuugccacug cuaagcugug aggcagugca ggcuggaca gccgaccucc agguugcgaa     10620
aaaccugguu ucugggaccu cccaccccag aguaaaaaga acggagccuc cgcuaccacc    10680
cucccacgug gugguagaaa gacggggucu agagguuaga ggagacccuc cagggaacaa    10740
auagugggac cauauugacg ccagggaaag accggagugg uucucugcuu uccuccaga    10800 ggucugugag cacaguuugc ucaagaauaa gcagaccuuu ggaugacaaa cacaaaacca    10860
cu                                                                   10862

<210> SEQ ID NO 4
<211> LENGTH: 10862
<212> TYPE: RNA
<213> ORGANISM: Yellow fever virus
<220> FEATURE:
<221> NAME/KEY: misc_feature
<223> OTHER INFORMATION: RNA sequence of the YFV 17D-213 strain

<400> SEQUENCE: 4
aguaaauccu gugugcuaau ugaggugcau uggucugcaa aucgaguugc uaggcaauaa      60
acacauuugg auuaauuuua aucguucguu gagcgauuag cagagaacug accagaacau     120
gucuggucgu aaagcucagg gaaaaacccu gggcgucaau augguacgac gaggaguucg     180
cuccuuguca aacaaaauaa aacaaaaaac aaaacaaauu ggaaacagac cuggaccuuc     240 aagaggguguu caaggauuua ucuuuuucuu uuguucaac auuuugacug gaaaaaagau     300
cacagcccac cuaaagaggu gugaaaau gcuggaccca agacaaggcu uggcuguucu     360
aaggaaaguc aagagagugg uggccaguuu gaugagagga uugccucaa ggaaacgccg     420 uucccaugau guucgacug ugcaauuccu aauuuggga augcuguuga ugacggguggg     480 agugaccuug gugcggaaaa acagauggu gcuccuaaau gugacaucug aggaccucgg    540
gaaaacauuc ucugugggca caggcaacug cacaacaaac auuuuggaag ccaaguacug     600
gugcccagac ucaauggaau acaacugucc caaucucagu ccaagagagg agccagauga    660
cauugauugc uggugcuaug ggguggaaaa cguuagaguc gcauugguua agugugacuc    720
agcaggcagg ucuaggaggu caagaagggc cauugacuug ccuacgcaug aaaaccaugg    780
uuugaagacc cggcaagaaa aauggaugac uggaagaaug ggugaaaggc aacuccaaaa    840
gauugagaga ugguucguga ggaaccccuu uuugcagug acggcucuga ccauugccua    900 ccuugugggga agcaacauga cgcaacgagu cgugauugcc cuacuggucu uggcuguugg    960
uccggccuac ucagcucacu gcauuggaau uacugacagg gauuucauug aggggugca    1020 uggaggaacu ugggguuucag cuacccugga gcaagacaag ugugucacug uuauggcccc    1080
ugacaagccu ucauuggaca ucucacuaga cagcuagcc auugauac ugcugaggu      1140 gaggaaagug uguuacaaug caguucucac ucaugugaag auuaaugaca guccccag      1200 cacuggagag gcccaccuag cugaagagaa cgaaggggac aaugcgugca gcgcacuua    1260
```

-continued

```
uucugauaga ggcuggggca auggcugugg ccuauuuggg aaaggagca uuguggcaug    1320 cgccaaauuc acuugugcca aauccaugag uuuguugau guugaucaga ccaaaauuca    1380
guaugucauc agagcacaau ugcauguagg ggccaagcag gaaaauugga cuaccgacau   1440
uaagacucuc aaguuugaug cccgucagg cucccaggaa gucgaguuca uuggguaugg    1500
aaaagcuaca cuggaaugcc aggugcaaac ugcgguggac uuugguaaca guuacaucgc   1560
ugagauggaa acagagagcu ggauagugga cagacagugg gcccaggacu ugacccugcc   1620
auggcagagu ggaaguggcg ggguguggag agagaugcau caucuugucg aauuugaacc   1680
uccgcaugcc gccacuauca gaguacuggc ccugggaaac caggaaggcu ccuugaaaac   1740
agcucuuacu ggcgcaauga ggguuacaaa ggacacaaau gacaacaacc uuuacaaacu   1800
acauggugga cauguuucuu gcagagugaa auugucagcu uugacacuca aggggacauc   1860
cuacaaaaua ugcacugaca aaauguuuuu ugucaagaac ccaacugaca cuggccaugg   1920
cacugugugu augcaggugu aaguucaaa aggagccccc ugcaggauuc cagugauagu    1980
agcugaugau cuuacagcgg caaucaauaa aggcauuuug guuacaguua ccccaucgc    2040 cucaaccaau gaugaugaag ugcugauuga ggugaaccca ccuuuuggag acagcuacau   2100
uaucguuggg agaggagauu cacgucucac uuaccagugg cacaaagagg gaagcucaau   2160
aggaaaguug uucacucaga ccaugaaagg cguggaacgc cuggccguca ugggagacac   2220
cgccugggau uucagcuccg cuggaggguu cuucacuucg guugggaaag gaauucauac   2280
ggguguuggc ucugccuuuc aggggcuauu uggcggcuug aacuggauaa caaaggucau   2340 cauggggcg guacuuauau ggguuggcau caacacaaga aacaugacaa uguccaugag   2400
caugaucuug guaggaguga ucaugauguu uuugucucua ggaguugggg cggaucaagg   2460
augcgccauc aacuuuggca agagagcu caagugcgga gauggauaucu ucauauuuag   2520 agacucugau gacuggcuga acaaguacuc auacuauca gaagauccug ugaagcuugc   2580
aucaauagug aaagccucuu uugaagaagg gaagugggc cuaaaauucag uugacuccu   2640 ugagcaugag auguggagaa gcagggcaga ugaaucaau gccauuuuug aggaaaacga   2700
gguggacauu ucguugucg ugcaggaucc aaagaauguu uaccagagag gaacucaucc   2760
auuuuccaga auucgggaug gucugcagua ugguuggaag acuuggggua gaaccuugu   2820 guucuccca gggaggaaga augggaagcuu caucauagau ggaaaguccca ggaaaagaaug  2880 cccguuuuca aaccgggucu ggaauucuu ccagauagag gaguuuggga cgggagugu   2940 caccacacgc guguacaugg acgcagucu ugaauacacc auagacugcg auggaucuau   3000
cuugggugca gcggugaacg gaaaaaagag ugcccauggc ucuccaacau uuggaugg    3060 aagucaugaa guaaauggga cauggaugau ccaccccuug gaggcauuag auuacaagga   3120
gugugagugg ccacugacac auacgauugg aacaucaguu gaagagagug aaauguucau   3180
gccgagauca aucggaggcc caguuagcuc ucacaaucau auccuggau acaaggucua   3240 gacgaacgga ccuuggaugc agguaccacu agaagugaag agagaagcuu gccacaggggac  3300 uagcgugauc auugauggca acugugaugg acgggggaaa ucaaccagau ccaccacgga   3360
uagcgggaaa guuauuccug aaugguguug ccgucccugc acaaugccgc cugugagcuu   3420
ccauggaugu gaugggugu gguaucccau ggaaauuagg ccaaggaaaa cgcaugaaag   3480
ccaucuggug cgcuccuggg uuacagcugg agaaauacau gcugucccuu uugguuuggu   3540
gagcaugaug auagcaaugg aaguggguccu aaggaaaaga cagggaccaa agcaaauguu   3600
```

```
gguuggagga guagugcucu ugggagcaau gcuggucggg caaguaacuc uccuugauuu    3660
gcugaaacuc acaguggcug ugggauugca uuuccaugag augaacaaug gaggagacgc    3720
cauguauaug gcguugauug cugccuuuuc aaucagacca gggcugcuca ucggcuuugg    3780
gcucaggacc cuauggagcc cucgggaacg ccuugugcug acccuaggag cagccauggu    3840
ggagauugcc uuggguggcg ugaugggcgg ccugugaag uaucuaaaug caguuucucu    3900
cugcauccug acaauaaaug cuguugcuuc uaggaaagca ucaaauacca ucuugccccu    3960
cauggcucug uugacaccug ucacuauggc ugaggugaga cuugccgcaa uguucuuuug    4020 ugccguggu aucauagggg uccuucacca gaauuucaag gacaccucca ugcagaagac    4080
uauaccucug guggcccuca cacucacauc uuaccugggc uugacacaac cuuuuuggg    4140 ccugugugca uuucuggcaa cccgcauauu gggcgaagg aguaucccag ugaaugaggc    4200
acucgcagca gcggucuag ugggagugcu ggcaggacug gcuuucagg agauggagaa    4260 cuuccuuggu ccgauugcag uuggaggacu ccugaugaug cugguuagcg uggcugggag    4320 ggugaugg cuagagcuca agaagcuugg ugaaguuuca ugggaagagg aggcggagau    4380
cagcgggagu uccgcccgcu augaugggc acucagugaa caagggagu caagcugcu    4440 uucugaagag aaagugccau gggaccaggu ugugaugacc ucgcuggccu ugguuggggc    4500 ugccccuccau ccauuugcuc uucgcuggu ccugcuggg uggcuguuuc augucagggg    4560
agcuaggaga agugggaug ucuugugga uauucccacu ccaagauca ucgaggaaug    4620 ugaacaucug gaggauggga uuuauggcau auuccagcu accuucuugg gggccucca    4680 gcgaggagug gaguggcac agggaggggu guuccacaca auguggcaug ucacaagagg    4740
agcuuuccuu gucaggaaug gcaagaaguu gauccaucu ugggcuucag uaaaggaaga    4800
ccuugucgcc uaugugggcu caugguaaguu ggaaggcaga ugggauggag aggaagaggu    4860
ccaguugauc gcggcuguuc caggaaagaa cguggucaac guccagacaa aaccgagcuu    4920
guucaaagug aggaauggg gagaaaucgg ggcugucgcu cuugacuauc cgaguggcac    4980
uucaggaucu ccuauuguua acaggaacgg agaggugauu gggcuguacg gcaauggcau    5040
ccuugucggu gacaacuccu ucgugccgc cauaucccag acugagguga aggaagaagg    5100
aaaggaggag cuccaagaga ucccgacaau gcuaagaaa ggaaugacaa cugccuuga    5160 uuuucauccu ggagcuggga agacaagacg uuuccccca cagaucuugg ccgagugcgc    5220
acggagacgc uugcgcacuc uuguguuggc ccccaccagg guuguccuuu cugaaaugaa    5280
ggaggcuuuu cacggccugg acgugaaauu ccacacacag gcuuuuccg cucacggcag    5340 cgggagagaa gucauugaug cuaugugcca ugccacccua acuuacagga uguuggaacc    5400
aacuaggguu guuaacuggg aagugaucau uauggaugaa gcccauuuuu uggauccagc    5460
uagcauagcc gcuagagguu gggcagcgca cagagcuagg gcaaaugaaa gugcaacaau    5520
cuugaugaca gccacaccgc cugggacuag ugaugaauuu ccacauucaa auggugaaau    5580
agaagauguu caaacggaca uacccagugg gcccuggaac acagggcaug acuggauccu    5640
ggcugacaaa aggcccacgg cauguuccu uccauccauc agagcugcaa augucauggc    5700
ugccucuuug cguaaggcug gaaagagugu ggugguccug aacaggaaaa ccuuugagag    5760
agaauacccc acgauaaagc agaagaaacc ugacuuuaua uuggccacug acauagcuga    5820 aauggggagcc aaccuuugcg uggagcgagu gcuggauugc aggacggcuu uuaagccugu    5880
gcuuguggau gaagggagga aggugcaau aaaagggcca cuucguaucu ccgcauccuc    5940
ugcugcucaa aggagggggc gcauugggag aaaucccaac agagauggag acucauacua    6000
```

| | |
|---|---|
| cuauucugag ccuacaagug aaaauaaugc ccaccacguc ugcugguugg aggccucaau | 6060 |
| gcucuuggac aacauggagg ugaggggugg aauggucgcc ccacucuaug gcguugaagg | 6120 |
| aacuaaaaca ccaguuuccc cuggugaaau gagacugagg gaugaccaga ggaaagucuu | 6180 |
| cagagaacua gugaggaauu ugaccugcc cguuggcuu ucguugcaag uggccaaggc | 6240 |
| ugguuugaag acgaaugauc guaaguggug uuuugaaggc ccugaggaac augagaucuu | 6300 |
| gaaugacagc ggugaaacag ugaagugcag ggccuccugga ggagcaaaga agccucugcg | 6360 |
| cccaaggugg ugugaugaaa ggggucauc ugaccagagu gcgcugucug aauuuauuaa | 6420 |
| guuugcugaa gguaggaggg gagcugcuga agugcuaguu gugcugagug aacucccuga | 6480 |
| uuccuggcu aaaaaggug gagaggcaau ggauaccauc agugguuc uccacucuga | 6540 |
| ggaaggcucu agggcuuacc gcaaugcacu aucaaugaug ccugaggcaa ugacaauagu | 6600 |
| caugcuguuu uacuggcug gacuccugac aucgggaaug gucaucuuuu ucaugucucc | 6660 |
| caaaggcauc aguagaaugu cuauggcgau gggcacaaug gccggcgugu gauaucucau | 6720 |
| guuccuugga ggcgucaaac ccacucacau cucccauauc augcucauau ucuuugugccu | 6780 |
| gauggugguu ugaucccccg agccagggca acaaaggucc auccaagaca accaaguggc | 6840 |
| auaccucauu auuggcaucc ugacgcuggu uucagcggug gcagccaacg agcuaggcau | 6900 |
| gcuggagaaa accaagagg accucuuugg gaagaagaac uuaauuccau cuagugcuuc | 6960 |
| acccuggagu uggccggauc uugaccugaa gccaggagcu gccuggacag uguacguugg | 7020 |
| cauuguuaca augcucucuc caauguugca ccacuggauc aaagucgaau auggcaaccu | 7080 |
| gucucugucu ggaauagccc agucagccuc agccuuucu uucauggaca aggggauacc | 7140 |
| auucaugaag augaauaucu cggucauaau gcugcugguc aguggcugga uucaauaac | 7200 |
| agugaugccu cugcucugug gcauagggug cgccaugcuc cacgucuc ucauuuuacc | 7260 |
| uggaaucaaa gcgcagcagu caaagcuugc acagagaagg guguuccaug gcguugccaa | 7320 |
| gaacccugug guugauggga auccaacagu ugacauugag gaagcuccug aaaugccugc | 7380 |
| ccuuuaugag aagaaacugg cucuauaucu ccuucuugcu cucagccuag cuucuguugc | 7440 |
| caugugcaga acgcccuuuu cauuggcuga aggcauugcc cuagcaucag cugccucagg | 7500 |
| gccgcucaua gagggaaaca ccagccuucu uuggaaugga cccauggcug ucuccaugac | 7560 |
| aggagucaug aggggaauc acuaugcuuu uguggagguc auguacaauc uaggaagau | 7620 |
| gaaaacugga cgccggggga gcgcgaaugg aaaaacuuug gugaagucu ggaagaggga | 7680 |
| acugaaucug uuggacaagc gacaguuuga guuguauaaa aggaccgaca uuguggaggu | 7740 |
| ggaucgugau acggcacgca ggcauuuggc cgaaggaag guggacaccg ggguggcggu | 7800 |
| cuccagggg accgcaaagu uaaggugguu ccaugagcgu ggcuauguca agcuggaagg | 7860 |
| uagggugauu gaccuggggu guggccgcgg aggcuggugu acuacgcug cugcgcaaaa | 7920 |
| ggaagugagu ggggucaaag gauuuacucu uggaagagac ggccaugaga aacccaugaa | 7980 |
| ugugcaaagu cugggaugga caucaucac cuucaaggac aaaacugaua uccaccgccu | 8040 |
| agaaccagug aaaugugaca cccuuuugug ugacauugga gagucaucau cgucaucggu | 8100 |
| cacagagggg gaaaggaccg ugagagucu ugauacugua gaaaaauggc uggcuugugg | 8160 |
| gguugacaac uucugugugga aggguuagc uccauacaug ccagauguuc gagaaaacu | 8220 |
| ggaauugcuc caaggaggu uuggcggaac agugaucagg aacccucucu ccaggaauuc | 8280 |
| cacucaugaa auguacuacg ugucuggagc ccgcagcaau gucacauuua cugugaacca | 8340 |

| | |
|---|---|
| aacaucccgc cuccugauga ggagaaugag gcguccaacu ggaaaaguga cccuggaggc | 8400 |
| ugacgucauc cucccaauug ggacacgcag uguugagaca gacaagggac cccuggacaa | 8460 |
| agaggccaua gaagaaaggg uugagaggau aaaaucugag uacaugaccu cuugguuuua | 8520 |
| ugacaaugac aaccccuaca ggaccuggca cuacuguggc uccuaugauca caaaaaccuc | 8580 |
| aggaagugcg gcgagcaugg uaaaugugu uauuaaaauu cugacauauc caugggacag | 8640 |
| gauagaggag gucacaagaa uggcaaugac ugacacaacc ccuuuuggac agcaaagagu | 8700 |
| guuuaaagaa aaaguugaca ccagagcaaa ggauccacca gcgggaacua ggaagaucau | 8760 |
| gaaaguuguc aacaggugge uguuccgcca ccuggccaga gaaagaaacc ccagacugug | 8820 |
| cacaaaggaa gaauuuauug caaaaguccg aagucaugca gccauggag cuuaccugga | 8880 |
| agaacaagaa caguggaaga cugccaauga ggcugcccaa gacccaaagu ucugggaacu | 8940 |
| ggugaaugaa gaaaggaagc ugcaccaaca aggcagugu cggacuugug uguacaacau | 9000 |
| gauggggaaa agagagaaga agcugucaga guuuggaaaa gcaaagggaa gccgugccau | 9060 |
| auggauaug uggcugggag cgcgguaucu ugaguuugac gcccugggau uccugaauga | 9120 |
| ggaccauugg gcuuccaggg aaaaacucagg aggaggagug gaaggcauug gcuuacaaua | 9180 |
| ccuaggauau gugaucagag accugcgc aauggauggu ggggauucu acgcggauga | 9240 |
| caccgcugga ugggacacgc gcaucacaga ggcagaccuu gaugaugaac aggagaucuu | 9300 |
| gaacuacaug agcccacauc acaaaaaacu ggcacaagca gugaugggaaa ugacauacaa | 9360 |
| gaacaaagug gugaaagugu ugagaccagc ccaggagggg aaagccuaca ggaugucau | 9420 |
| aagucgacga gaccagagag gauccgggca gguagugacu uaugcucuga acaccaucac | 9480 |
| caacuugaaa guccaauuga ucagaaugge agaagcagag auggugauac aucaccaaca | 9540 |
| uguucaagau gugaugaauu caguucgac caggcuggag gcaugcuca cugagcacgg | 9600 |
| auguaacaga cugaagagga uggcggugag uggagacgac ugugugguce ggcccaucga | 9660 |
| ugacagguuc ggccuggccc ugucccaucu caacgccaug uccaagguua aaggacau | 9720 |
| aucugaaugg cagccaucaa aagguggaa ugauuggag aaugugcccu ucuguuccca | 9780 |
| ccacuuccau gaacuacagc ugaaggaugg caggaggauu gguggugccuu gccgagaaca | 9840 |
| ggacgagcuc auugggagag gaagggugue uccaggaaac ggcuggauga ucaaggaaac | 9900 |
| agcuugcccu agcaaagccu augccaacau ggucacugu auguauuuuc acaaagggga | 9960 |
| caugaggcua cugucauugg cuguuuccuc agcuguuccc accaugggg uuccacaagg | 10020 |
| acgcacaaca uggucgauuc auggaaagg ggaguggaug accacggaag acaugccuuga | 10080 |
| ggguggaaac agaguaugga uaaccaacaa cccacacaug caggacaaga caauggugaa | 10140 |
| aaaauggaga gauguccuu aucuaaccaa gagacaagac aagcugugcg gaucacugau | 10200 |
| uggaaugacc aauaggggcca ccugggccuc ccacauccau uuaguauccc aucguauccg | 10260 |
| aacgcugauu ggacaggaga aauacacuga cuaccaaca gucauggaca gguauucugu | 10320 |
| ggaugcugac cugcaacugg gugagcuuau cugaaacacc aucaacagg aauaaccggg | 10380 |
| auacaaaacca cggguggaga accggacucc ccacaaccug aaaccgggau auaaaccacg | 10440 |
| gcuggagaac cggacuccgc acuuaaaaug aaacagaaac cgggauaaaa acuacgaug | 10500 |
| gagaaccgga cuccacacau ugagacagaa gaaguuguca gcccagaacc ccacacgagu | 10560 |
| uuugccacug cuaagcugug aggcagugca ggcugggaca gccgaccucc agguugcgaa | 10620 |
| aaaccugguu ucugggaccu cccaccccag aguaaaaaga acggagccuc cgcuaccacc | 10680 |
| cucccacgug guguagaaaa gacggggucu agagguuaga ggagacccuc cagggaacaa | 10740 |

-continued

```
auagugggac cauauugacg ccagggaaag accggagugg uucucugcuu uuccuccaga    10800
ggucugugag cacaguuugc ucaagaauaa gcagaccuuu ggaugacaaa cacaaaacca    10860
cu                                                                   10862
```

<210> SEQ ID NO 5
<211> LENGTH: 10862
<212> TYPE: RNA
<213> ORGANISM: Yellow fever virus
<220> FEATURE:
<221> NAME/KEY: misc_feature
<223> OTHER INFORMATION: RNA sequence of the YFV 17DD strain

<400> SEQUENCE: 5

```
aguaaauccu gugugcuaau ugaggugcau uggucugcaa aucgaguugc uaggcaauaa      60
acacauuugg auuaauuuua aucguucguu gagcgauuag cagagaacug accagaacau     120
gucuggucgu aaagcucagg gaaaacccu gggcgucaau augguacgac gaggagaucg      180
cuccuuguca aacaaaauaa aacaaaaaac aaaacaaauu ggaaacagac cuggaccuuc     240 aagaggguguu caaggauuua ucuuuuucuu uuuguucaac auuuugacug gaaaaaagau     300
cacagcccac cuaaagaggu gugggaaaau gcuggaccca agacaaggcu uggcuguucu     360
aaggaaaguu aagagagugg uggccaguuu gaugagagga uuguccucaa ggaaacgccg     420
uucccaugau guucuacug ugcaauuccu aauuuuggga augcuguuga ugacggguggg     480 agugaccuug gugcggaaaa acagauggu gcuccuaaau ugacaucug aggaccucgg      540 gaaaacauuc ucugugggca caggcaacug cacaacaaac auuuuggaag ccaaguacug     600
gugcccagac ucaauggaau acaacugucc caaucucagu ccgagagagg agccagauga    660 cauugauuugc uggugcuaug gguggaaaaa cguauagaguc gcaauggua agugugacuc     720 agcaggcagg ucuaggaggu caagaagggc cauugacuug ccuacgcaug aaaaccaugg     780
uuugaagacc cggcaagaaa aauggaugac uggaagaaug ggugaaagg aacuccaaaa      840 gauugagaga ugguucguga ggaaccccuu uuuugcagug acagcucuga ccauugccua      900
ccuuguggga agcaacauga cgcaacgagu cgugauugcc cuacggucu uggucuguugg    960 uccggccuac ucagcucacu gcauuggau uacugacagg gauucauug aggggugca     1020 uggaggaacu ugggguucag cuacccugga gcaagacaag ugucacacug uuauggccc     1080 ugacaagccu ucauuggca ucucacuaga gacaguagcc auugauagac cugcugaggc    1140 gaggaaaagug uguacaaug caguucucac ucaugugaag auuaaugaca agugcccccag   1200 cacuggagag gcccaccuag cugaagagaa cgaagggggac aaugcgugca agcgcacuua    1260
uucugauaga ggcuggggca auggcugugg ccuauuuggg aaaggagca uguggcaug     1320 cgccaaauc acuugugcca aauccaugag uuuguugag guugaucaga ccaaaaauca     1380
guaugucauc agagcacaau ugcauguagg ggccaagcag aaaaauugga auaccagcau    1440
uaagacucuc aaguuugaug ccgucagg cuccaggaa gucgaguuca uugggguaugg     1500 aaaagcuaca cuggaaugcc aggugcaaac ugcgguggac uuugguaaca guuacauagc    1560
ugagauggaa acagagagcu ggaauaggga cagacagugg gcccaggacu ugacccugcc    1620
auggcagagu ggaaguggcg ggugugggag agaaaugcau caucuugucg aauuugaacc    1680
uccgcaugcc gccacuauca gaguacuggc ccugggaaac caggaaggcu ccuugaaaac    1740
agcucuuaca ggcgcaauga ggguuacaaa ggacacaaau gacaacaacc uuuacaaacu    1800 acaugggugga cauguucuu gcagaguaa auugucagcu uugacacuca agggggacauc    1860
```

-continued

```
cuacaaaaua ugcacugaca aaauguuuuu ugucaagaac ccaacugaca cuggccaugg   1920
cacuguugug augcagguga aagugccaaa aggagccccc ugcaggauuc cagugauagu   1980
agcugaugau cuuacagcgg caaucaauaa aggcauuuug guuacaguua accccaucgc   2040
cucaaccaau gaugaugaag ugcugauuga ggugaaccca ccuuuuggag acagcuacau   2100
uaucguugga agaggagauu cacgucucac uuaccagugg cacaaagagg gaagcucaau   2160
aggaaaguug uucacucaga ccaugaaagg cguggaacgc cuggccguca ugggagacgu   2220
cgccugggau uucagcuccg cuggaggguu cuucacuucg guugggaaag gaauucauac   2280 gguguuggc ucugccuuuc aggggcuauu uggcggcuug aacuggauaa caaaggucau   2340
caugggggcg guacuuauau ggguuggcau caacacaaga aacaugacaa uguccaugag   2400
caugaucuug guaggaguga ucaugauguu uuugucucua ggaguugggg cggaucaagg   2460
augcgccauc aacuuuggca agagagagcu caagugcgga gaugguaucu ucauauuuag   2520
agacucugau gacuggcuga acaaguacuc auacuaucca gaagauccug ugaagcuugc   2580
aucaauagug aaagccucuu ugaagaagg gaaguguggc cuaaauucag uugacucccu   2640
ugagcaugag auguggagaa gcagggcaga ugagaucaau gccauuuuug aggaaaacga   2700 ggugacauu ucuguugucg ugcaggaucc aaagaauguu uaccagagag gaacucaucc   2760
auuuuccaga auucgggaug gucugcagua ugguugaag acuuggggua agaaccuugu   2820
guucucccca ggaggaagaa auggaagcuu caucauagau ggaaagucca ggaaagaaug   2880
cccguuuuca aaccggggucu ggaauucuuu ccagauagag gaguuuggga cgggagoguu   2940 caccacacgc guguacaugg acgcagucuu ugaauacacc auagacugcg auggaucuau   3000 cuuggggugca gcggugaacg gaaaaaagag ugcccauggc ucccaacau uuuggauggg   3060 aagucaugaa guaaaugggga caugugaugau ccacaccuug gaggcauuag auuacaagga   3120
gugugagugg ccacugacac auacgauugg aacaucaguu gaagagagug aaauguucau   3180
gccgagauca aucggaggcc caguuagcuc ucacaaucau aucccuggau acaagguuca   3240
gacgaacgga ccuuggaugc agguaccacu agaagugaag agagaagcuu gcccagggac   3300
uagcgugauc auugauggca acugugaugg acgggaaaa ucaaccagau ccaccacgga   3360
uagcgggaaa guuauuccug aauggugung ccgcuccugc acaaugccgc cugugagcuu   3420 ccauggguagu gaugggguguu gguaucccau ggaaauuagg ccaaggaaaa cgcaugaaag   3480 ccaucugguug cgcuccuggg uuacagcugg agaaauacau gcugucccuu ugguuuggu   3540 gagcaugaug auagcaaugg aaguuguccu aaggaaaaga cagggaccaa agcaaaugcu   3600
gguuggagga guagugcucu ugggagcaau gcugguuggg caaguaacuc uccuugauuu   3660
gcugaaacuc acagggcug ugggauugca uuuccaugag augaacaaug gaggagacgc   3720 caugguauaug gcguugauug cugccuuuuc aaucagacca gggcugcuca ucggcuuugg   3780
gcucaggacc cuauggagcc ucgggaacg ccuugccug acccuaggag cagccauggu   3840
ggagauugcc uugggguggcg ugaugggcgg ccuguggaag uaucuaaaug caguuucucu   3900
cugcauccug acaauaaaug cuguugcuuc uaggaaagca ucaaauaccA uccuugcCccu   3960 caugGcucug uugacaccug ucacuauggc ugaggugaga cuugccgcaa ugcucuuuug   4020 ugccguggu aucauagggg uccuucacca gaacuucaag gacaccuccA ugcagaagac   4080
uauaccucug guggcccuca cacucacauc uuaccuggc uugacacaac cuuuuuuggg   4140
ccugugugca uuucuggcaa cccgcauauu ugggcgaagg aguaucccag ugaaugaggc   4200
```

```
acuugcagca gcuggucuag ugggagugcu ggcaggacug gcuuuucagg agauggagaa   4260
cuuccuuggu ccgauugcag uuggaggacu ccugaugaug cugguuagcg uggcugggag   4320 ggugggauggg cuagagcuca agaagcuugg ugaaguuuca ugggaagagg aggcggagau   4380
```

```
ggugggauggg cuagagcuca agaagcuugg ugaaguuuca ugggaagagg aggcggagau   4380
cagcggggagu ccgcccgcu augaugugggc acucagugaa caaggggagu caagcugcu   4440
uucugaagag aaagugccau ggaccaggu ugugaugacc ucgcuggccu ugguuggggc   4500
ugcccuccau ccauuugcuc uucugcuggu ccugcuggg uggcuguuuc augucagggg   4560
agcuaggaga agugggaug ucuugugggu uauucccacu ccaagauca uugaggaaug   4620
ugaacaucug gaggaugggga uuuauaggcau auuccagucu accuucuugg gggcccccca   4680
gcgaggagug ggaguggcac agggaggggu guuccacaca augugggcaug ucacaagagg   4740
agcuuuccuu gucaggaaug gcaagaaguu gauccaucu ugggcuucag uaaaggaaga   4800
ccuugucgcc uaugguggcu cauggaaguu ggaaggcaga uggaugggag aggaagaggu   4860
ccaguugauc gcugcuguuc caggaaagaa cguggucaac guccagacaa aaccgagcuu   4920
guucaaagug aggaaugggg gggaaaucgg ggcuguugcu cuugacuauc caagugggcac   4980
uucaggaucu ccuauuguua acaggaacgg agaggugauu gggcuguacg gcaauggcau   5040
ccuugucggu gacaacuccu ucgugucccgc cauauccag acugaggguga aggaagaagg   5100
aaaggaggag cuccgagaga ucccgacaau gcuaaagaaa ggaaugacaa cuauccuuga   5160
uuuucauccu ggagcuggga agacaagacg uuucccuccca cagaucuugg ccgagugcgc   5220
acggcgacgc uugcgcacuc uuguguuggc ccccaccagg guuguucuuu cugaaaugaa   5280
ggaggcuuuu cacggccugg acgugaaauu ccacacacag gcuuuuuccg cucacggcag   5340
cggggagagaa ucauugaug caaugugccaa ugccacccuua acuuacagga uguuggaacc   5400
aacuaggguu guuaacuggg aagugaucau uauggaugaa gcccauuuuu ugggauccagc   5460
uagcauagcc gcugagaggu gggcagcgca cagagcuagg gcaaugaaaa gugcaacaau   5520
cuugaugaca gccacaccgc cugggacuag ugaugaauuu ccacauucaa augugugaaau   5580
agaagauguu caaacggaca uacccagugaa gcccuggaac acagggcaug acuggauccu   5640
ggcugacaaaa aggcccacggg cauggguuccu uccauccauc agagcugcaa augucauggc   5700
ugccucuuug cguaaggcug gaaagagugu ggugguccug aacaggaaaaa ccuuugagag   5760
agaauaccccc acgauaaagc agaagaaacc ugacuuuuaua uuggccacug acauagcuga   5820
aaugggggagcc aaccuuugcg uggagcgagu gcuggauugc aggacggcuu uuaagccugu   5880
gcuuguggau gaagggagga aggugggcaau aaaagggcca cuucguaucu ccgcauccuc   5940
ugcugcucaa aggaggggggc gcauugggag aaaucccaac agagauggag acucauacua   6000
cuauucugag ccuacaagug aaaauaaugc ccaccgguc ugcugguugg aggccucaau   6060
gcucuugggau aacauggagg ugaggggugg aauggucggcc ccacucuaug gcguugaagg   6120
aacuaaaaca ccaguuuccc cuggugaaaau gagacugagg gaugaccaga ggaaagucuu   6180
cagagaacua gugaggaauu gugaccugcc gcuuuggcuu ucguggcaag uggccaaggc   6240
ugguuugaag acgaaugauc guaagugggug uuuugaaggc ccugaggaac augagaucuu   6300
gaaugacagc gggugaaacag ugaagugcag ggcuccugga ggagcaaaga agccucugcg   6360
cccaagguggg ugugaugaaa ggguggucauc ugaccagagu gcgcugucug aauuuuauuaa   6420
guuugcugaa gguaggaggg gagcugcuga agugcuaguu gugcugagug aacucccuga   6480
uuuccuggcu aaaaaggug gagaggcaau ggacaccauc agugugguu uccacucuga   6540
ggaaggcucu agggcuuacc gcaaugcacu aucaaugaug ccugaggcaa ugacaauagu   6600
```

```
caugcuguuu auacuggcug gacuccugac aucgggaaug gcaucuuuu ucaugucucc    6660
caaaggcauc aguagaaugu cuauggcgau gggcacaaug gccggcugug gauaucucau    6720
guuccuugga ggcgucaaac ccacucacau cuccuauauc augcucauau ucuuugcccu    6780
gauggugguu gugaucccg agccagggca acaaaggucc auccaagaca accaaguggc    6840
auaccucauu auuggcaucc ugcgcugguu uucagcgguc gcagccaacg agcuaggcau    6900
gcuggagaaa accaaagagg accucuuugg gaagaagaac uuaauuccau cuagugcuuc    6960
acccuggagu uggccggauc uugaccugaa gccaggagcu gccuggacag uguacguugg    7020
cauuguuaca augcucucuc caauguugca ccacuggauc aaagucgaau auggcaaccu    7080
gucucugucu ggaauagccc agucagccuc agccuuucu uucauggaca aggggauacc    7140
auucaugaag augaauaucu cggucauaau gcugcugguc aguggcugga auucaauaac    7200
agugaugccu cugcucugug gcauagggug cgccaugcuc cacggucuc ucauuuuacc    7260
uggaaucaaa gcgcagcagu caaagcuugc acagagaagg guguuccaug gcguugccaa    7320
gaacccugug guugaugggga auccaacagu ugacauugag gaagcuccug aaaugccugc    7380
ccuuuaugag aagaaacugg cucuauaucu ccuucuugcu cucagccuag cuucuguugc    7440
caugugcaga acgcccuuuu cauuggcuga aggcauuguc cuagcaucag cugccuuagg    7500
gccgcucaua gagggaaaca ccagccuucu uggaauggga cccauggcug ucuccaugac    7560
aggagucaug cgggggaauc acauagcuuu ugugggaguc auguacaauc uauggaagau    7620
gaaaacugga cgccggggga gcgcgaaugg aaaaacuuug ggugaagucu ggaagaggga    7680
acugaaucug uuggacaagc aacaguuuga guuguauaaa aggaccgaca uuguggaggu    7740
ggaucgugau acggcacgca ggcauuuggc cgaagggaag guggacaccg ggugggcggu    7800
cuccaggggg accgcaaagu uaaggugguu ccaugagcgu ggcuauguca agcuggaagg    7860
uagggugauu gaccuggggu guggccgcgg aggcuggugu uacuacgcug cugcgcaaaa    7920
ggaagugagu ggggucaaag gauuuacucu uggaagagac ggccaugaga aaccaugaa    7980
ugugcaaagu cugggauggga acaucaucac cuucaaggac aaaacugaca uccaccgccu    8040
agaaccagug aaaugugaca cccuuuugug ugacauugga gagucaucau cgucaucggu    8100
cacagagggg gaaaggaccg ugagaguucu ugauacugua gaaaaauggc uggcuugugg    8160
gguugacaac uucugugug aggugunuagc uccauacaug ccagauguuc cgagaaaacu    8220
ggaauugcuc caaaggaggu uggcggaac agugaucagg aacccucucu ccaggaauuc    8280
cacucaugaa auguacuacg ugucuggagc ccgcagcaau gucacauuua cugugaacca    8340
aacaucccgc cuccugauga ggagaaugag gcguccaacu ggaaaaguga cccuggaggc    8400
ugacgucauc cucccaauug gacacgcag uguugacaca gacaagggac cccuggacaa    8460
agaggccauu aagaaagggg uugagaggau aaaaucugag uacaugaccu cuugguuuua    8520
ugacaaugac aaccccuaca ggaccuggca cuacugggc uccauguca aaaaccuc    8580
aggaaguugcg gcgagcaugg uaaauggugu uauuaaauu cugacauauc cauggacag    8640
gauagaggag gucacaagaa uggcaaugac ugacacaacc ccuuuggac agcaaagagu    8700
guuuaaagaa aaaguugaca ccagagcaaa ggaucacca gcgggaacua ggaagaucau    8760
gaaaguuguc aacaggugge uguuccgcca ccuggccaga gaaaagagcc ccagacugug    8820
cacaaaggaa gaauuuauug caaaaguccg aagucaugca gccauggag cuuaccggga    8880
agaacaagaa caguggaaga cugccaauga ggcuguccaa gacccaaagu ucuggggacu    8940
```

```
gguggaugaa gaaaggaagc ugcaccaaca aggcaggugu cggacuugug uguacaacau    9000
gauggggaaa agagagaaga agcugucaga guuugggaaa gcaaagggaa gccgugccau    9060
augguauaug uggcuggag cgcgguaucu ugaguuugag gcccugggau uccugaauga     9120
ggaccauugg gcuuccaggg aaaacucagg aggaggagug gaaggcauug gcuuacaaua    9180
ccuaggauau gugaucagag accuggcugc aauggauggu ggaggauucu acgcggauga    9240
caccgcugga ugggacacgc gcaucacaga ggcagaccuu gaugaugaac aggagaucuu    9300
gaacuacaug agcccacauc acaaaaaacu ggcacaagca gugauggaaa ugacauacaa    9360
gaacaaagug gugaaagugu ugagaccagc cccagggggg aaagccuaca uggaugucau    9420
aagucgacga gaccagagag gauccgggca gguagugacu uaugcucuga acaccaucac    9480
caacuugaaa guccaauuga ucagaauggc agaagcagag augguagauac auccaccaaca   9540 uguucaagau ugugaugaau caguucugac caggcuggag gcauggcuca cugagcacgg    9600
auguaacaga cugaagagga uggcggugag uggagacgac ugugugggucc ggcccaucga   9660 ugacagguuc ggccuggccc ugucccaucu caacgccaug uccaagguua gaaaggacau    9720
aucugaaugg cagccaucaa aagggugggaa ugauugggag aaugugcccu ucuguuccca   9780
ccacuuccau gaacuacagc ugaaggaugg caggaggauu gugugccuu gccgagaaca    9840 ggacgagcuc auugggagag aagggugguc uccaggaaac ggcuggauga ucaaggaaac    9900
agcuugccuc agcaaagccu augccaacau guggucacug auguauuuuc acaaagggga   9960
caugaggcua cugucauugg cuguuccuc agcuguuccc accucauggg uuccacaagg    10020
acgcacaaca uggucgauuc auggaaaagg ggaguggaug accacggaag acaugcuuga    10080 ggugggaac agaguaugga uaaccaacaa cccacacaug caggacaaga caauggugaa    10140
aaaauggaga gauguccccuu aucuaaccaa gagacaagac aagcugugcg gaucacugau   10200
uggaaugacc aauagggcca ccugggccuc ccacauccau uuagucaucc aucguauccg    10260
aacgcugauu ggacaggaga aauacacuga cuaccuaaca gucauggaca gguauucugu    10320
ggaugcugac cugcaacugg gugagcuuau cugaaacacc aucuaacagg aauaaccggg    10380 auacaaaacca cggguggaga accggacucc ccacaaccug aaaccgggau auaaaccacg    10440
gcuggagaac cggacuccgc acuuaaaaug aaacagaaac cgggauaaaa acuacggaug    10500
gagaaccgga cuccacacau ugagacagaa gaaguugucca gcccagaacu ccacacgagu     10560
uuugccacug cuaagcugug aggcagugca ggcugggaca gccgaccucc agguugcgaa    10620
aaaccugguu ucugggaccu cccaccccag aguaaaaaga acggagccuc cgcuaccacc    10680
cucccacgug gugguagaaa gacggggucu agagguuaga ggagacccuc cagggaacaa    10740
auagugggac cauauugacg ccaggggaaag accggagugg uucucugcuu uccuccaga    10800 ggucugugag cacaguuugc ucaagaauaa gcagaccuuu ggaugacaaa cacaaaacca    10860
cu                                                                  10862
```

<210> SEQ ID NO 6
<211> LENGTH: 10833
<212> TYPE: RNA
<213> ORGANISM: Yellow fever virus
<220> FEATURE:
<221> NAME/KEY: misc_feature
<223> OTHER INFORMATION: RNA sequence of the YFV Asibi strain

<400> SEQUENCE: 6

```
gugugcuaau ugaggugcau uggucugcaa aucgaguugc uaggcaauaa acacauuugg      60
```

|  |  |  |  |  |  |
|---|---|---|---|---|---|
| auuaauuuua | aucguucguu | gagcgauuag | cagagaacug | accagaacau | gucuggucgu | 120 |
| aaagcucagg | gaaaaacccu | gggcgucaau | augguacgac | gaggaguucg | cuccuuguca | 180 |
| aacaaaauaa | aacaaaaaac | aaaacaaauu | ggaaacagac | cuggaccuuc | aagaggyguu | 240 |
| caaggauuua | ucuuuuucuu | uuuguucaac | auuuugacgu | gaaaaagau | cacggcccac | 300 |
| cuaagaggu | uguggaaaau | gcuggaccca | agacaaggcu | uggcuguucu | aaggaaaguu | 360 |
| aagagaguigg | uggccaguuu | gaugagagga | uugccucaa | ggaaacgccg | uucccaugau | 420 |
| guucugacug | ugcaauuccu | aauuuuggga | augcuguuga | ugacggguigg | agugaccuug | 480 |
| gugcggaaaa | acagaugguu | gcuccuaaau | gugacaucug | aggacccgg | gaaaacauuc | 540 |
| ucugugggca | caggcaacug | cacaacaaac | auuuuggaag | ccaaguacug | ugcccagac | 600 |
| ucaauggaau | acaacugucc | caaucucagu | ccaagagagg | agccagauga | cauugauugc | 660 |
| uggugcuaug | ggguggaaaa | cguuagaguc | gcauaugguia | agugugacuc | agcaggcagg | 720 |
| ucuaggaggu | caagaagggc | cauugacuug | ccuacgcaug | aaaaccaugg | uuugaagacc | 780 |
| cggcaagaaa | aauggaugac | uggaagaaug | ggugaaaggc | aacccaaaa | gauugagaga | 840 |
| uggcucguga | ggaacccccuu | uuuugcagug | acagcucuga | ccauugccua | ccuguggga | 900 |
| agcaacauga | cgcaacgagu | cgugauugcc | cuacuggucu | uggcuguuigg | uccggccuac | 960 |
| ucagcucacu | gcauuggaau | uacugacagg | gauuucauug | aggggguigca | uggaggaacu | 1020 |
| uggguuucag | cuacccugga | gcaagacaag | uguugucacug | uuauggcccc | ugacaagccu | 1080 |
| ucauuggaca | ucucacuaga | gacaguagcc | auugauggac | cugcugaggc | gaggaaaguig | 1140 |
|

```
aacuuggca agagagagcu caagugcgga gaugguaucu ucauauuuag agacucugau    2520
gacuggcuga acaaguacuc auacuaucca gaagauccug ugaagcuugc aucaauagug    2580
aaagccucuu uugaagaagg gaaguguggc cuaaauucag uugacucccu ugagcaugag    2640
auguggagaa gcagggcaga ugagaucaau gccauucuug aggaaaacga gguggacauu    2700
ucuguugucg ugcaggaucc aaagaauguu uaccagagag gaacucaucc auuuuccaga    2760
auucgggaug gucugcagua ugguuggaag acuuggggua agaaccuugu guucccca     2820 gggaggaaga auggaagcuu caucauagau ggaaagucca ggaaagaaug cccguuuuca    2880
aaccgggucu ggaauucuuu ccagauagag gaguuuggga cgggagugu caccacacgc    2940 guguacaugg acgcagucuu ugaauacacc auagacugcg auggaucuau cuugggugca    3000
gcggugaacg gaaaaaagag ugcccauggc ucuccaacau uuuggauggg aagucaugaa    3060
guaaauggga cauggaugau ccacaccuug gaggcauuag auuacaagga gugugagugg    3120
ccacugacac auacgauugg aacaucaguu gaagagagug aaauguucau gccgagauca    3180
aucggaggcc caguuagcuc ucacaaucau aucccuggau acaagguuca gacgaacgga    3240
ccuuggaugc agguaccacu agaagugaag agagaagcuu gcccagggac uagcgugauc    3300
auugauggca acgugaugg acggggaaaa ucaaccagau ccaccacgga uagcgggaaa    3360
auuauuccug aauggguug ccgcuccugc acaaugccgc cugugagcuu ccauggugagu    3420 gaugggguguu gguaucccau ggaaauuagg ccaaggaaaa cgcaugaaag ccaucggug    3480 cgcuccuggg uuacagcugg agaaauacau gcugucccuu uugguuuggu gagcaugaug    3540
auagcaaugg aaguggcuu aaggaaaaga cagggaccaa agcaaauguu gguuggagga    3600
guggugcucu ugggagcaau gcuggucggg caaguaacuc uccuugauuu gcugaaacuc    3660
acaguggcug ugggauugca uuccaugag augaacaaug gaggagacgc cauguauaug    3720 gcguugauu cugccuuuuc aaucagacca gggcugcuca ucggcuuugg gcucaggacc    3780
cuauggagcc cucgggaacg ccuuguacug acccuaggag cagccauggu ggagauugcc    3840 uugggguggca ugaugggcgg ccuguggaag uaucuaaaug caguuucucu cugcauccug    3900
acaauaaaug cuguagcuuc uaggaaagca ucaaauacca ucuugccccu cauggcucug    3960
uugacaccug ucacuauggc ugaggugaga cuugccacaa ugcucuuuug uaccguggu    4020 aucauagggg uccuucacca gaacuccaag gacaccucca ugcagaagac uauaccucug    4080
guggcccuca cacucacauc uuaccugggc uugacacaac cuuuuuuggg ccugugugca    4140
uuucuggcaa cccgcauauu ugggcgaagg aguaucccag ugaaugaggc acucgcagca    4200
gcuggucuag ugggagugcu ggcaggacug gcuuuucagg auggagaa cuuccuuggu    4260 ccgauugcag uuggaggaau ccugaugaug cgguuagcg uggcugggag gguggauggg    4320
cuagagcuca agaagcuugg ugaaguuuca uggaagagg aggcggagau cagcggaagu    4380
uccgcccgcu augaugugc cacucaguaa caagggagu caagcugcu uucugaagag    4440 aaagugccau gggaccaggu ugugaugacc ucgcuggccu ugguugggc ugccauucau    4500 ccauuugcuc uucugcuggu ccuugcuggg uggcuguuuc augucaggg agcuaggaga    4560 agugggggaug ucuugggga uauucccacu ccuaagauca uugaggaaug ugaacacugu    4620
gaggauggga uuuauggcau auuccaguca accuucuugg gggccuccca gcgaggagug    4680
ggaguggcac agggaggggu guuccacaca augugggcauc ucacaagagg agcuuuccuu    4740
gucaggaaug gcaagaaguu gauuccaucu ugggcuucag uaaaggaaga ccuugucgcc    4800
```

-continued

| | |
|---|---|
| uaugguggcu cauggaaguu ggaaggcaga uggggauggag aggaagaggu ccaauugauc | 4860 |
| gcugcuguuc caggaaagaa cguggucaac guccagacaa aaccgagcuu guucaaagug | 4920 |
| aggaaugggg gagaaaucgg ggcugucgcu cuugacuauc cgaguggcac uucaggaucu | 4980 |
| ccuauuguua acaggaacgg agaggugauu gggcuguacg gcaauggcau ccuugucggu | 5040 |
| gacaacuccu ucgugugccgc cauaucccag acugaggug aggaagaagg aaaggaggag | 5100 |
| cuccaagaga ucccgacaau gcuaaagaaa ggaaugacaa cuauccuuga uuucauccu | 5160 |
| ggagcuggga agacaagacg uuuucucccca cagaucuugg ccgagugcgc acggagacgc | 5220 |
| uugcgcacuc uuguguuggc ccccaccagg guuguucuuu cugaaaugaa ggaggcuuuu | 5280 |
| cacggccugg acgugaaauu ccacacacag gcuuuuccg cucacggcag cgggagagaa | 5340 |
| gucauugaug ccaugugcca ugccacccua acuuacagga guuggaacc aacuaggguu | 5400 |
| guuaacuggg aagugaucau cauggaugaa gcccauuuuu uggauccagc uagcauagcc | 5460 |
| gccagaggu gggcagcgca cagagcuagg gcaaaugaaa gugcaacaau cuugaugaca | 5520 |
| gccacaccgc cugggacuag ugaugaauuu ccacauucaa augugaaau agaagauguu | 5580 |
| caaacggaca uacccagug gcccuggaac acagggcaug acuggauccu ggcugacaaa | 5640 |
| aggcccacgg caugguuccu uccauccauc agagcugcaa augucauggc ugccucuuug | 5700 |
| cguaaggcug gaaagagugu ggugguccug aacaggaaaa ccuuugagag agaauacccc | 5760 |
| acgauaaagc agaagaaacc ugacuuuaua uuggccacug acauagcuga aaugggagcc | 5820 |
| aaccuuugcg uggagcgagu gcuggauugc aggacggcuu uaagccugu gcuguggau | 5880 |
| gaagggagga aggugguaau aaaagggcca cuucgcaucu ccgcauccuc ugcugcucaa | 5940 |
| aggaggggc gcauugggag aaaucccaac agaauggag acucauacua cuauucugag | 6000 |
| ccuacaagug aagauaaugc ccaccacguc ugcgguuggg aggccucaau gcucuuggac | 6060 |
| aacauggagg ugagggugg aauggucgcc ccacucuaug gcguugaagg aacuaaaaca | 6120 |
| ccaguuuccc cuggugaaau gagacugagg gaugaccaga ggaaagucuu cagagaacua | 6180 |
| gugaggaauu gugaccugcc cguuuggcuu ucguggcaag uggccaaggc ugguugaag | 6240 |
| acgaaugauc guaaggggug uuuugaaggc ccugaggaac augagaucuu gaaugacagc | 6300 |
| ggugaaacag ugaagugcag ggcuccugga ggagcaaaga agccucugcg cccaaggugg | 6360 |
| ugugaugaaa gggugucauc ugaccagagu gcgcugucug aauuuauuaa guuugcugaa | 6420 |
| gguaggaggg gagcugcgga agugcuaguu gugcugagug aacucccuga uuccuggcu | 6480 |
| aaaaaaggug gagaggcaau ggauaccauc agugugmuuc uccacucuga ggaaggcucu | 6540 |
| agggcuuacc gcaaugcacu aucaaugaug ccugaggcaa ugacaauagu caugcuguuu | 6600 |
| auacuggcug acuacugac aucgggaaug gucaucuuuu ucaugucucc caaaggcauc | 6660 |
| aguagaaugu cuauggcgau gggcacaaug gccggcugug gauaucucau guccuugga | 6720 |
| ggcgucaaac ccacucacau cuccauauac augcucauau ucuuugcccu gauggugguu | 6780 |
| gugaucccg agccagggca acaaaggucc auccaagaca accaaguggc auaccucauu | 6840 |
| auuggcaucc ugacgcuggu uucaguggug gcagccaacg agcuaggcau gcuggagaaa | 6900 |
| accaaagagg accucuuugg gaagaagaac uuaauuccau cuagugcuuc acccuggagu | 6960 |
| uggccggauc uugaccugaa gccaggagcu gccuggacag uguacguugg cauuguuaca | 7020 |
| augcucucuc caaugguugca ccacuggauc aaagucgaau auggcaaccu gucucugucu | 7080 |
| ggaauagccc agcagccuc agccuuucu uucauggaca agggauacc auucaugaag | 7140 |
| augaauaucu cggucauaau acugcugguc agugcugga auucaauaac agugaugccu | 7200 |

```
cugcucugug gcauagggug cgccaugcuc cacuggucuc ucauuuuacc uggaaucaaa    7260
gcgcagcagu caaagcuugc acagagaagg guguuccaug gcguugccaa gaacccugug    7320
guugauggga auccaacagu ugacauuagg gaagcuccug aaaugccugc ccuuuaugag    7380
aagaaacugg cucuauaucu ccuucuugcu cucagccuag cuucguugc caugugcaga    7440 acgcccuuuu cauggcuga aggcauuguc cuagcaucag cugccuuagg gccgcucaua    7500
gagggaaaca ccagccuucu uuggaaugga cccauggcgcu cuccaugac aggaucaug    7560 cgggggaauu acuaugcuuu gugggaguc auacaauc uauggaagau gaaaacugga    7620
cgccggggga gugcgaaugg aaaaacuuug ggugaaguvcu ggaagaggga acugaaucug    7680
uuggacaagc aacaguuuga guuguauaaa aggaccgaca uuguggaggu ggaucgugau    7740
acggcacgca gcauuuggc cgaagggaag guggacaccg ggguggcggu uccaggggg    7800 accgcaaagu uaaggugguu ccaugagcgu ggcuaugauca agcuggaagg uagggugauu    7860 gaccugggu guggccgcgg aggcuggugu uacuacgcug cugcgcaaaa ggaagugagu    7920
ggggucaaag gauucacucu uggaagagac ggccaugaga aacccaugaa ugugcaaagu    7980
cuggauggua acaucauuac cuucaaggac aaaacugaua uccaccgccu agaaccagug    8040
aaaugugaca cccuuuugug ugacauugga gagucaucau cgucaucggu cacagagggg    8100
gaaaggaccg ugagaguucu ugauacugua gaaaaauggc uggcuugugg gguugacaac    8160 uucugugua aggguguuagc uccauacaug ccagauguuc ucgagaaacu ggaauugcuc    8220
caaaggaggu uggcggaac agugaucagg aacccucucu ccaggaauuc cacucaugaa    8280
auguacuacg ugucuggagc ccgcagcaau gucacauuua cugugaacca aacaucccgc    8340
cuccugauga ggagaaugag gcguccaacu ggaaaaguga cccggaggc ugacgucauc    8400 cucccaauug ggacacgcag uguugagaca gacaagggac cccuggacaa agaggccaua    8460
gaagaaaggg uugagaggau aaaaucgag uacaugaccu cuugguuuua ugacaaugac    8520
aaccccuaca ggaccuggca cuacugggc uccuaugca caaaaaccuc aggaagugcg    8580
gcgagcaugg uaaauggugu uauuaaaauu cugacauacc cauggacag gauagaggag    8640 gucacaagaa uggcaaugac ugacacaacc ccuuuggac agcaaagagu guuuaaagaa    8700
aaaguugaca ccagagcaaa ggauccacca gcgggaacua ggaagaucau gaaaguuguc    8760 aacaggugc uguccgcca ccuggccaga gaaaagaacc ccagacugug cacaaaggaa    8820 gaauuuaug caaaguccg aagucaugca gccauggag cuuaccugga gaacaagaa    8880 caguggaaga cugccaauga ggcuguccaa gacccaaagu cugggaacu gguggaugaa    8940 gaaaggaagc ugcaccaaca aggcagcugu cggacuugug uacaacau gaugggaaa    9000 agagagaaga agcugucaga guuugggaaa gcaaagggaa gccgugccau augguauaug    9060
uggcugggag cgcgguaucu ugaguuugaag gcccuggau uccgaauga ggaccauugg    9120 gcuuccaggg aaaacucagg aggagagug gaaggcauug gcuuacauuga ccuaggauau    9180 gugaucagag accggcugc aauggauggu ggggauucu acgcggauga caccgcugga    9240
ugggacacgc gcaucacaga ggcagaccu gaugaugaac aggagaucuu gaacuacaug    9300
agcccacauc acaaaaaacu ggcacaagca gugauggaaa ugcauacaa gaacaaagug    9360 gugaaagugu ugagaccagc cccaggaggg aaagccuaca uggaugucau aagucgacga    9420
gaccagagag gauccggca gguagugacu uaugcucuga acaccauca caacuugaa    9480 guccaauuga ucagaauggc agaagcagag auggugauac aucaccaaca uguucaagau    9540
```

| | | | | | |
|---|---|---|---|---|---|
| ugugaugaau | caguucugac | caggcuggag | gcauggcuca | cugagcacgg | auguaacaga | 9600 |
| cugaagagga | uggcggugag | uggagacgac | uguguggucc | ggcccaucga | ugacagguuc | 9660 |
| ggccuggccc | ugucccaucu | caacgccaug | uccaagguua | gaaaggacau | aucugaaugg | 9720 |
| cagccaucaa | aaggguggaa | ugauuggag | aaugugcccu | ucuguuccca | ccacuuccau | 9780 |
| gaacuacagc | ugaaggaugg | caggaggauu | guggugccuu | gccgagaaca | ggacgagcuc | 9840 |
| auugggagag | gaagggguguc | uccaggaaac | ggcuggauga | ucaaggaaac | agcuugccuc | 9900 |
| agcaaagccu | augccaacau | ggguucacug | auguauuuuc | acaaaaggga | caugaggcua | 9960 |
| cgucauugg | cuguuccuc | agcuguuccc | accucauggg | uuccacaagg | acgcacaaca | 10020 |
| uggucgauuc | augggaaagg | ggaguggaug | accacggaag | acaugcuuga | gguguggaac | 10080 |
| agaguaugga | uaaccaacaa | cccacacaug | caggacaaga | caauggugaa | agaauggaga | 10140 |
| gaugucccuu | aucuaaccaa | gagacaagac | aagcugugcg | gaucacugau | uggaaugacc | 10200 |
| aauagggcca | ccugggccuc | ccacauccau | uggucaucc | aucguauccg | aacgcugauu | 10260 |
| ggacaggaga | aauauacuga | cuaccuaaca | gucauggaca | gauauucugu | ggaugcugac | 10320 |
| cugcaaccgg | gugagcuuau | cugaaacacc | aucuaauagg | aauaaccggg | auacaaacca | 10380 |
| cggguggaga | accggacucc | ccacaacuug | aaaccgggau | auaaaccacg | gcuggagaac | 10440 |
| cggacuccgc | acuuaaaaug | aaacagaaac | cgggauaaaa | acuacggaug | gagaaccgga | 10500 |
| cuccacacau | ugagacagaa | gaaguuguca | gcccagaacu | ccacacgagu | uugccacug | 10560 |
| cuaagcugug | aggcagugca | ggcugggaca | gccgaccucc | agguugcgaa | aaaccugguu | 10620 |
| ucugggaccu | cccaccccag | aguaaaaaga | acggagccuc | cgcuaccacc | cucccacgug | 10680 |
| ggguagaaa | gacggggucu | agagguuaga | ggagacccuc | cagggaacaa | auaguggac | 10740 |
| cauauugacg | ccagggaaag | accggagugg | uucucugcuu | uuccuccagg | ggucugugag | 10800 |
| cacaguuugc | ucaagaauaa | gcagaccuuu | gga | | | 10833 |

<210> SEQ ID NO 7
<211> LENGTH: 10862
<212> TYPE: RNA
<213> ORGANISM: Yellow fever virus
<220> FEATURE:
<221> NAME/KEY: misc_feature
<223> OTHER INFORMATION: RNA sequence of the YFV TV3112 strain

<400> SEQUENCE: 7

| | | | | | |
|---|---|---|---|---|---|
| aguaaauccu | gugugcuaau | ugaggugcau | uggucugcaa | aucgaguugc | uaggcaauaa | 60 |
| acacauuugg | auuaauuuua | aucguucguu | gagcgauuag | cagagaacug | accagaacau | 120 |
| gucuggucgu | aaagcucagg | gaaaacccu | gggcgucaau | augguacgac | gaggaguucg | 180 |
| cuccuuguca | aacaaaauaa | aacaaaaaac | aaaacaaauu | ggaaacagac | cuggaccuuc | 240 |
| aagaggguuu | caaggauuua | ucuuuuucuu | uuuguucaac | auuuugacug | gaaaaaagau | 300 |
| cacagcccac | cuaagaggu | gugaaaaau | gcuggaccca | agacaaggcu | uggcuguucu | 360 |
| aaggaaaguc | aagagagugg | uggccaguuu | gaugagagga | uuguccucaa | ggaaacgccg | 420 |
| uucccaugau | guucugacug | ugcaauuccu | aauuuuggga | augcuguuga | ugacggggug | 480 |
| agugaccuug | gugcggaaaa | acagaugguu | gcuccuaaau | ugacaucug | aggaccucgg | 540 |
| gaaaacauuc | ucuguggca | caggcaacug | cacaacaaac | auuuggaag | ccaaguacug | 600 |
| gugcccagac | ucaauggaau | acaacugucc | caaucucagu | ccaagagagg | agccagauga | 660 |
| cauugauugc | uggugcuaug | ggguggaaaa | cguuagaguc | gcauauggua | agugugacuc | 720 |

```
agcaggcagg ucuaggaggu caagaagggc cauugacuug ccuacgcaug aaaaccaugg    780
uuugaagacc cggcaagaaa aauggaugac uggaagaaug ggugaaaggc aacuccaaaa    840
gauugagaga ugguucguga ggaaccccuu uuuugcagug acggcucuga ccauugccua    900
ccuuguggga agcaacauga cgcaacgagu cgugauugcc cuacugguou uggcuguugg    960 uccggccuac ucagcucacu gcauuggaau uacugacagg gauuucauug aggggggugca   1020 uggaggaacu ugggguuucag cuacccugga gcaagacaag ugugucacug uuauggcccc   1080
ugacaagccu ucauuggaca ucucacuaga gacaguagcc auugauagac cugcugaggu   1140
gaggaaagug uguuacaaug caguucucac ucaugugaag auuaaugaca agugccccag   1200
cacuggagag gcccaccuag cugaagagaa cgaaggggac aaugcgugca agcgcacuua   1260
uucugauaga ggcuggggca auggcugugg ccuauuuggg aaaggagca uuguggcaug   1320 cgccaaauuc acuugugcca aauccaugag uuuguuugag guugaucaga ccaaaauuca   1380
guaugucauc agagcacaau ugcauguugg ggccaagcag gaaaauugga cuaccgacau   1440
uaagacucuc aaguuugaug cccugucagg cucccaggaa gucgaguuca uugggguaugg   1500 aaaagcuaca cuggaaugcc aggugcaaac ucgcguggac uuugguaaca guuacaucgc   1560
ugagauggaa acagagagcu ggauaguggga cagacagugg gcccaggacu ugacccugcc   1620
auggcagagu ggaaguggcg gggugugggag agagaugcau caucuugucg aauuugaacc   1680
uccgcaugcc gccacuauca gaguacuggc ccugggaaac caggaaggcu ccuugaaaac   1740
agcucuuacu ggcgcaauga ggguuacaaa ggacacaaau gacaacaacc uuuacaaacu   1800
acauggugga cauguuucuu gcagagugaa auugucagcu uugacacuca aggggacauc   1860
cuacaaaaua ugcacugaca aauguuuuu ugucaagaac ccaacugaca cuggccaugg   1920
cacuguugug augcagguga aagucaaaa ggagccccc ugcaggauuc cagugauagu   1980
agcugaugau cuuacagcgg caaucaauaa aggcauuuug guuacaguua ccccaucgc   2040 cucaaccaau gaugaugaag ugcugauuga ggugaaccca ccuuuuggag acagcuacau   2100
uaucguuggg agaggagauu cacgucucac uuaccagugg cacaaagagg gaagcucaau   2160
aggaaaguug uucacucaga ccaugaaagg cguggaacgc cuggccguca ugggagacac   2220
cgccugggau uucagcuccg cuggagggu cuucacuucg guugggaaag gaauucauac   2280
gguguuuggc ucugccuuuc aggggcuauu uggcggcuug aacugauaa caaaggucau   2340 caugggggcg guacuuauau ggguuggcau caacacaaga aacaugacaa uguccaugag   2400
caugaucuug uuaggaguga ucaugauguu uuugucucua ggaguugggg cggaucaagg   2460
augcgccauc aacuuuggca agagagagcu caagugcgga gauggauaucu ucauauuuag   2520 agacucugau gacuggcuga acaaguacuc auacuauccaa gaagaccucug ugaagcuugc   2580 aucaauagug aaagccucuu uugaagaagg gaagugugge cuaaauucag uugaccccu   2640 ugagcaugag auguggagaa gcagggcaga ugagaucaau gccauuuuug aggaaaacga   2700 ggugacauu ucguugucg ugcaggaucc aaagaauguu uaccagagag gaacucaucc   2760
auuuuccaga auucgggaug gucugcagua ugguuggaag acuggggua agaaccuugu   2820 guucuccca ggggaggaaga auggaagcuu caucauagau ggaaagucca ggaaagaaug   2880
cccguuuuca aaccgggucu ggaauucuuu ccagauagag gaguuuggga cgggagughu   2940
caccacacgc guguacaugg acgcagucuu ugaauacacc auagacugcg auggaucuau   3000 cuuggggca gcgguggaacg gaaaaaagag ugcccauggc ucccaacau uuggauggg   3060 aagucaugaa guaaauggga cauggaugau ccacaccuug gaggcauuag auuacaagga   3120
```

-continued

```
gugugagugg ccacugacac auacgauugg aacaucaguu gaagagagug aaauguucau   3180
gccgagauca aucggaggcc caguuagcuc ucacaaucau aucccuggau acaagguuca   3240
gacgaacgga ccuuggaugc agguaccacu agaagugaag agagaagcuu gcccagggac   3300
uagcgugauc auugauggca acugugaugg acggggaaaa ucaaccagau ccaccacgga   3360
uagcgggaaa guuauccug aauggguguug ccgcuccugc acaaugccgc cugugagcuu   3420 ccauggduagu gaugggugduu gguaucccau ggaaauuagg ccaaggaaaa cgcaugaaag   3480 ccaucggguug cgcuccuggg uuacagcugg agaaauacau gcugucccuu uugguuuggu   3540
gagcaugaug auagcaaugg aaguggguccu aaggaaaaga cagggaccaa agcaaauguu   3600
gguuggagga guagugcucu ugggagcaau gcugguucggg caaguaacuc uccuugauuu   3660
gcugaaacuc acaggggcug ugggauugca uuccaugag gugaacaaug gaggagacgc   3720
cauguauaug gcguugauug cugccuuuuc aaucagacca gggcugcuca ucggcuuugg   3780
gcucaggacc cuauggagcc cucgggaacg ccuugugcug acccuaggag cagccauggu   3840
ggagauugcc uuggguggcg ugaugggcgg ccuguggaag uaucuaaaug caguuucucu   3900
cugcauccug acaauaaaug cuguugcuuc uaggaaagca ucaaauacca ucuugcccccu   3960 cauggcucug uugacaccug ucacuauggc ugaggugaga cuugccgcaa uguucuuuug   4020
ugccgugguu aucauagggg uccuucacca gaauuucaag gacaccucca ugcagaagac   4080
uauaccucug gugggcccuca cacucacauc uuaccugggc uugacacaac cuuuuuuggg   4140
ccugugugca uuucuggcaa cccgcauauu ugggcgaagg aguaucccag ugaaugaggc   4200
acucgcagca gcuggucuag ugggagugcu ggcaggacug gcuuuucagg agauggagaa   4260
cuuccuuggu ccgauugcag uuggaggacu ccugaugaug cugguuagcg uggcugggag   4320
gguggauggg cuagagcuca agaagcuugg ugaaguuuca ugggaagagg aggcggagau   4380 cagcggagagu uccgcccgcu augauggguggc acucagugaa caaggggagu ucaagcugcu   4440
uucugaagag aaagugccau gggaccaggu ugugaugacc ucgcuggccu ugguugggggc   4500 ugccccuccau ccauuugcuc uucgcuggu ccugcuggdg ugg cuguuuc augucagggg   4560 agcuaggaga agugggggaug ucuugugggga uauucccacu ccuaagauca ucgaggaaug   4620
ugaacaucug gaggaauggga uuuauggcau auuccaguca accuucuugg gggccuccca   4680
gcgaggagug ggaguggcac agggagggggu guuccacaca auguggcaug ucacaagagg   4740
agcuucccuu gucaggaaug gcaagaaguu gauccaucu ugggcuucag uaaaggaaga   4800
ccuugucgcc uauggggcu cauggaaguu ggaaggcaga ugggauggag aggaagaggug   4860 ccaguugauc gcggcuguuc caggaaagaa cguggucaac guccagacaa aaccgagcuu   4920
guucaaagug aggaaugggg agaaaaucgg ggcugucgcu cuugacuauc cgagugggcac   4980 uucaggaucu ccuauuguua acaggaacgg agaggugauu gggcuguacg gcaauggcau   5040
ccuugucggu gacaacuccu ucgucccgc cauaucccag acugaggugga aggaagaagg   5100 aaaggaggag cuccaagaga ucccgacaau gcuaaagaaa ggaaugacaa cuguccuuga   5160
uuuucauccu ggagcuggga agacaagacg uuuccucccca caogaucuugg ccgagugcgc   5220 acggagacgc uugcgcacuc uuguguugcc ccccaccagg guugucuuu cugaaaugaa   5280 ggaggcuuuu cacggccugg acgugaaauu ccacacacag cuuuuuccgu cucacggcag   5340
cgggagagaa gucauugaug cuaugugcca ugccacccua acuuacagga guuggaaac   5400 aacuagggguu guuaacuggg aagugaucau uauggaugaa gcccauuuuu uggauccagc   5460
```

```
uagcauagcc gcuagagguu gggcagcgca cagagcuagg gcaaaugaaa gugcaacaau   5520
cuugaugaca gccacaccgc cugggacuag ugaugaauuu ccacauucaa auggugaaau   5580
agaagauguu caaacggaca uacccaguga gcccuggaac acagggcaug acuggauccu   5640
ggcugacaaa aggcccacgg caugguuccu uccauccauc agagcugcaa augucauggc   5700
ugccucuuug cguaaggcug gaaagagugu ggugguccug aacaggaaaa ccuuugagag   5760
agaauacccc acgauaaagc agaagaaacc ugacuuuaua uuggccacug acauagcuga   5820
aaugggagcc aaccuuugcg uggagcgagu gcuggauugc aggacggcuu uuaagccugu   5880
gcuugggau gaaggagga aaggugggcaau aaaaggggcca cuucguaucu ccgcauccuc   5940
```

```
uagggugauu gaccuggggu guggccgcgg aggcuggugu uacuacgcug cugcgcaaaa   7920
ggaagugagu ggggucaaag gauuuacucu uggaagagac ggccaugaga aacccaugaa   7980
ugugcaaagu cugggaugga acaucaucac cuucaaggac aaaacugaua uccaccgccu   8040
agaaccagug aaaugugaca cccuuuugug ugacauugga gagucaucau cgucaucggu   8100
cacagagggg gaaaggaccg ugagaguucu ugauacugua gaaaaauggc uggcuugugg   8160
gguugacaac uucugugugu aggguguuagc uccauacaug ccagauguuc ugagaaacu   8220 ggaauugcuc caaaggaggu uuggcggaac agugaucagg aacccucucu ccaggaauuc   8280
cacucaugaa auguacuacg ugucuggagc ccgcagcaau gucacauuua cugugaacca   8340
aacaucccgc cuccugauga ggagaaugag gcguccaacu ggaaaaguga cccuggaggc   8400
ugacgucauc cucccaauug ggacacgcag uguugagaca gacaagggac cccuggacaa   8460
agaggccaua aaagaaaggg uugagaggau aaaaucugag uacaugaccu cuugguuuua   8520
ugacaaugac aaccccuaca ggaccuggca cuacugugc uccauguca caaaaaccuc   8580 aggaagugcg gcgagcaugg uaaauggugu uauuaaaauu cugacauauc caugggacag   8640
gauagaggag gucacaagaa uggcaaugac ugacacaacc ccuuuuggac agcaaagagu   8700
guuuaaagaa aaaguugaca ccagagcaaa ggauccacca gcgggaacua ggaagaucau   8760
gaaaguuguc aacagguggc uguuccgcca ccuggccaga gaaaagaacc ccagacugug   8820
cacaaaggaa gaauuuauug caaaaguccg aagucaugca gccauggagg cuuaccugga   8880
agaacaagaa caguggaaga cugccaauga ggcuguccaa gacccaaagu ucugggaacu   8940
gguggaugaa gaaaggaagc ugcaccaaca aggcaggugu cggacuugug uguacaacau   9000
gauggggaaa agagagaaga agcugucaga guuugggaaa gcaaagggaa gccgugccau   9060 auggauaug uggcugggag cgcgguaucu ugaguuugag gcccugggau uccgaaugaa   9120
ggaccauugg gcuuccaggg aaaacucagg aggaggagug gaaggcauug gcuuacaaua   9180
ccuaggauau gugaucagag accuggcugc aauggauggu ggugauucu acgcggauga   9240 caccgcugga ugggacacgc gcaucacaga ggcagaccuu gaugaugaac aggagaucuu   9300
gaacuacaug agcccacauc acaaaaaacu ggcacaagca gugauggaaa ugacauacaa   9360
gaacaaagug gugaaagugu ugagaccagc cccaggaggg aaagccuaca uggaugucau   9420
aagucgacga gaccagagag gauccgggca gguagugacu uaugcucuga acaccaucac   9480
caacuugaaa guccaauuga ucagaauggc agaagcagag auggugauac aucaccaaca   9540
uguucaagau gugaugaau caguucgac caggcuggga gcauggcuca cugagcacgg   9600
auguaacaga cugaagagga uggcggugag uggagacgac ugugugguc ggcccaucga   9660 ugacagguuc ggccuggccc uguccaucu caacgccaug uccaagguua aaggacau   9720 aucugaaugg cagccaucaa aaggguggaa ugauggggag aaugugcccu ucuguuccca   9780
ccacuuccau gaacuacagc ugaaggaugg caggaggauu gguggccuu gccgagaaca   9840 ggacgagcuc auugggagag gaaggugguc uccaggaaac ggcuggauga ucaaggaaac   9900
agcuugccuc agcaaagccu augccaacau ggucacug auguauuuuc acaaagggaa   9960
caugaggcua cugucauugg cuguuccuc agcuguccc accucaugg uuccacaagg   10020 acgcacaaca uggucgauuc augggaaagg ggaguggaug accacggaag acaugcuuga   10080 ggugugggaac agaguaugga uaaccaacaa cccacacaug caggacaaga caauggaaa   10140 aaaauggaga gaugucccuu aucuaaccaa gagacaagac aagcugugcg gaucacugau   10200
```

| | |
|---|---|
| uggaaugacc aauagggcca ccugggccuc ccacauccau uuggucaucc aucguauccg | 10260 |
| aacgcugauu ggacaggaga aauacacuga cuaccuaaca gucauggaca gguauucugu | 10320 |
| ggaugcugac cugcaacugg gugagcuuau cugaaacacc aucuaacagg aauaaccggg | 10380 |
| auacaaacca cggguggaga accggacucc cacaaccug aaaccgggau auaaaccacg | 10440 |
| gcuggagaac cggacuccgc acuuaaaaug aaacagaaac cgggauaaaa acuacggaug | 10500 |
| gagaaccgga cuccacacau ugagacagaa gaaguuguca gcccagaacc ccacacgagu | 10560 |
| uuugccacug cuaagcugug aggcagugca ggcugggaca gccgaccucc agguugcgaa | 10620 |
| aaaccugguu ucugggaccu cccaccccag aguaaaaaga acggagccuc cgcuaccacc | 10680 |
| cucccacgug gugguagaaa gacggggucu agagguuaga ggagacccuc cagggaacaa | 10740 |
| auagugggac cauauugacg ccagggaaag accggagugg uucucugcuu uccuccaga | 10800 |
| ggucugugag cacaguuugc ucaagaauaa gcagaccuuu ggaugacaaa cacaaaacca | 10860 |
| cu | 10862 |

<210> SEQ ID NO 8
<211> LENGTH: 10862
<212> TYPE: RNA
<213> ORGANISM: Yellow fever virus
<220> FEATURE:
<221> NAME/KEY: misc_feature
<223> OTHER INFORMATION: RNA sequence of the YFV TV3111 strain

<400> SEQUENCE: 8

| | |
|---|---|
| aguaaauccu gugugcuaau ugaggugcau uggucugcaa aucgaguugc uaggcaauaa | 60 |
| acacauuugg auuaauuuua aucguucguu gagcgauuag cagagaacug accagaacau | 120 |
| gucuggucgu aaagcucagg gaaaaacccu gggcgucaau augguacgac gaggagaucg | 180 |
| cuccuuguca aacaaaauaa aacaaaaaac aaaacaaauu ggaaacagac cuggaccuuc | 240 |
| aagaggguguu caaggauuua ucuuuuucuu uuuguucaac auuuugacug gaaaaaagau | 300 |
| cacagcccac cuaaagaggu guggaaaau gcuggaccca agacaaggcu ggcuguucu | 360 |
| aaggaaaguc aagagagugg uggccaguuu gaugagagga uuguccucaa ggaaacgccg | 420 |
| uucccaugau guucugacug ugcaauuccu aauuugggga augcuguuga uacggguga | 480 |
| agugaccuug gugcggaaaa acagauggu gcuccuaaau ugacaucug aggaccucgg | 540 |
| gaaaacauuc ucugugggca caggcaacug cacaacaaac auuuuggaag ccaaguacug | 600 |
| gugcccagac ucaauggaau acaacugucc caaucucagu ccaagagagg agccagauga | 660 |
| cauugauugc uggugcuaug ggguggaaaa cguuagaguc gcauggguua agugugacuc | 720 |
| agcaggcagg ucuaggaggu caagaagggc cauugacuug ccuacgcaug aaaaccaugg | 780 |
| uuugaagacc cggcaagaaa aauggaugac uggaagaaug ggugaaaggc aacuccaaaa | 840 |
| gauugagaga ugguucguga ggaaccccuu uuuugcagug acggcucuga ccauugccua | 900 |
| ccuugugga agcaacauga cgcaacgagu cgugauugcc cuacggucu ggcucuuugg | 960 |
| uccggccuac ucagcucacu gcauuggaau uacugacagg gauuucauug aggggugca | 1020 |
| uggaggaacu uggguuucag cuacccugga gcaagacaag ugucacacug uuauggcccc | 1080 |
| ugacaagccu ucauuggaca ucucacuaga gacaguagcc auugauagac cugcugaggu | 1140 |
| gaggaaaagug uguuacaaug caguucucac ucaugugaag auuaaugaca gugccccag | 1200 |
| cacuggagag gcccaccuag cugaagagaa cgaaggggac aaugcugcag agcgcacuua | 1260 |
| uucugauaga ggcuggggca augguugg ccuauugggg aaagggagca uguggcaug | 1320 |

```
cgccaaauuc acuugugcca aauccaugag uuuguuugag guugaucaga ccaaaauuca    1380
guaugucauc agagcacaau ugcauguagg ggccaagcag gaaaauugga cuaccgacau    1440
uaagacucuc aaguuugaug cccugucagg cucccaggaa gucgaguuca uuggguaugg    1500
aaaagcuaca cuggaaugcc aggugcaaac ugcgguggac uuugguaaca guuacaucgc    1560
ugagauggaa acagagagcu ggauagugga cagacagugg gcccaggacu ugacccugcc    1620
auggcagagu ggaaguggcg ggguguggag agagaugcau caucuugucg aauuugaacc    1680
uccgcaugcc gccacuauca gaguacuggc ccugggaaac caggaaggcu ccugaaaac     1740
agcucuuacu ggcgcaauga ggguuacaaa ggacacaaau gacaacaacc uuuacaaacu    1800
acauggugga cauguuucuu gcagagugaa auugucagcu uugacacuca aggggacauc    1860
cuacaaaaua ugcacugaca aaauguuuuu ugucaagaac ccaacugaca cuggccaugg    1920
cacuguugug augcagguga aagugucaaa aggagccccc ugcaggauuc cagugauagu    1980
agcugaugau cuuacagcgg caaucaauaa aggcauuuug guuacaguua accccaucgc    2040
cucaaccaau gaugaugaag ugcugauuga ggugaaccca ccuuuuggag acagcuacau    2100
uaucguuggg agaggagauu cacgucucac uuaccagugg cacaaagagg gaagcucaau    2160
aggaaaguug uucacucaga ccaugaaagg cguggaacgc cuggccguca ugggagacac    2220
cgccugggau uucagcuccg cuggaggguu cuucacuucg guugggaaag gaauucauac    2280
ggguguuggc ucugccuuuc aggggcuauu uggcggcuug aacugauaa caaaggucau    2340
cauggggcg guacuuauau ggguuggcau caacacaaga aacaugacaa uguccaugag    2400
caugaucuug uuaggaguga ucaugauguu uuugucucua ggaguugggg cggaucaagg    2460
augcgccauc aacuuuggca agagagagcu caagucgga gaugguaucu ucauauuuag    2520
agacucugau gacuggcuga acaaguacuc auacuauuca gaagauccug ugaagcuugc    2580
aucaauagug aaagccucuu ugaagaagg gaagugugc cuaaauucag uugacucccu     2640
ugagcaugag auguggagaa gcagggcaga ugagaucaau gccauuuug aggaaaacga     2700
gguggacauu ucuguugucg ugcaggaucc aaagaauguu uaccagagag gaacucaucc    2760
auuuuccaga auucgggaug gucugcagua ugguuggaag acuuggggua agaaccuugu    2820
guucuccccca gggaggaaga augagagcuu caucauagau ggaaagucca ggaaagaaug    2880
cccguuuuca aaccgggucu ggaauucuuu ccagauagag gaguuuggga cgggagguguu   2940
caccacacgc guguacaugg acgcagucuu ugaauacacc auagacugcg auggaucuau    3000
cuugggugca gcggugaacg gaaaaaagag ugcccauggc ucuccaacau uuuggaugggg   3060
aagucaugaa guaauggga cauggaugau ccacaccuug gaggcauuag auuacaagga     3120
gugugagugg ccacugacac auacgauugg aacaucaguu gaagagagug aaauguucau    3180
gccgagauca aucggaggcc caguuagcuc ucacaaucau aucccuggau acaagguuca    3240
gacgaacgga ccuuggaugc agguaccacu agaagugaag agagaagcuu gcccagggac    3300
uagcgugauc auugauggca cugaugga cgggaaaau caaccagau ccaccacgga         3360
uagcgggaaa guuauuccug aauggugutug ccgcuccugc acaaugccgc cugugagcuu    3420
ccauggauguag gaugguguu gguaucccau ggaaauuagg ccaaggaaaa cgcaugaaag    3480
ccaucugguc cgcuccuggg uuacagcugg agaaauacau gcugucccuu uugguuuggu    3540
gagcaugaug auagcaaugg aaguggccuu aaggaaaaga cagggaccaa agcaaauguu    3600
gguuggagga guagugcucu ugggagcaau gcuguucggg caaguaacuc uccuugauuu    3660
gcugaaacuc acaguggcug ugggauugca uuuccaugag gugaacaaug aggagacgc     3720
```

-continued

```
cauguauaug gcguugauug cugccuuuuc aaucagacca gggcugcuca ucggcuuugg   3780
gcucaggacc cuauggagcc cucgggaacg ccuugugcug acccuaggag cagccauggu   3840
ggagauugcc uuggguggcg ugaugggcgg ccuguggaag uaucuaaaug caguuucucu   3900
cugcauccug acaauaaaug cuguugcuuc uaggaaagca ucaaauacca ucuugccccu   3960
cauggcucug uugacaccug ucacuauggc ugaggugaga cuugccgcaa uguucuuuug   4020
ugccgugguu aucauagggg uccuucacca gaauuucaag gacaccucca ugcagaagac   4080
uauaccucug guggcccuca cacucacauc uuaccugggc uugacacaac cuuuuuggg    4140 ccugugugca uuucuggcaa cccgcauauu ugggcgaagg aguaucccag ugaaugaggc   4200
acucgcagca gcggucuag ugggagugcu ggcaggacug gcuuucagg agauggagaa     4260 cuuccuuggu ccgaugcag uuggaggacu ccugaugaug cugguuagcg uggcuggag     4320 ggugauggg cuagagcuca agaagcuugg ugaaguuuca ugggaagagg aggcggagau    4380
cagcgggagu ccgcccgcu augaugugcc acucagugaa caaggggagu caagcugcu    4440 uucugaagag aaagugccau gggaccaggu ugugaugacc ucgcuggccu uggguggggc   4500
ugccccccau ccauuugcuc uucgccuggu ccugcuggg uggcuguuuc augcagggg    4560 agcuaggaga agugggaug ucuuguggga uauucccacu ccaagauca ucgaggaaug    4620 ugaacaucug gaggauggga uuuauggcau auuccaguca accuucuugg gggccuccca   4680
gcgaggagug ggaguggcac agggagggu guccacaca augugcaug ucacaagagg     4740 agcuuuccuu gucaggaaug gcaagaaguu gauccaucu ugggcuucag uaaaggaaga   4800
ccuugucgcc uaugguggcu cauggaaguu ggaaggcaga ugggauggag aggaagaggu   4860
ccaguugauc gcggcuguuc caggaaagaa cguggucaac guccagacaa aaccgagcuu   4920
guucaaagug aggaaugggg gagaaaucgg ggcugucgcu cuugacuauc cgaguggcac   4980
uucaggaucu ccuauuguua acaggaacgg agaggugauu gggcuguacg gcaauggcau   5040
ccuugucggu gacaacuccu ucgugccgc cauauccag acugaggga aggaagagg     5100 aaaggaggag cuccaagaga ucccgacaau gcuaaagaaa ggaaugacaa cugaccuuga   5160
uuuucauccu ggagcuggga agacaagacg uuucccucca cagaucuugg ccgagugcgc   5220
acggagacgc uugcgcacuc uuguguuggc ccccaccagg guuguucuuu cugaaaugaa   5280
ggaggcuuuu cacggccugg acgugaaauu ccacacacag gcuuuuccg cucacggcag   5340 cgggagagaa ucauugaug cuaugugcca ugccacccua acuuacagga uguuggaacc   5400
aacuaggguu guuaacuggg aaugaucau uauggaugaa gcccauuuu uggauccagc   5460 uagcauagcc gcuagagguu gggcagcgca cagagcuagg gcaaaugaaa gugcaacaau   5520
cuugaugaca gccacaccgc cugggacuag ugaugaauuu ccacauucaa auggugaaau   5580
agaagauguu caaacggaca uacccaguga gcccuggaac acagggcaug acuggauccu   5640
ggcugacaaa aggcccacgg caugguuccu uccauccauc agagcugcaa augucauggc   5700
ugccucuuug cguaaggcug gaaagagugu ggugguccug aacaggaaaa ccuuugagag   5760
agaauacccc acgauaaagc agaagaaacc ugacuuuaua uuggccacug acauagcuga   5820 aauggggagcc aaccuuugcg uggagcgagu gcuggauugc aggacggcuu uuaagccugu   5880
gcuuguggau gaaggggagga aguggcaauu aaaagggcca cuucguaucu ccgcauccuc   5940
ugcugcucaa aggaggggc gcauggggag aaacccaac agagauggag acucauacua    6000
cuauucugag ccuacaagug aaaauaaugc ccaccacguc ugcuggunugg aggccucaau   6060
```

```
gcucuuggac aacauggagg ugaggggugg aauggucgcc ccacucuaug gcguugaagg     6120
aacuaaaaca ccaguuuccc cuggugaaau gagacugagg gaugaccaga ggaaagucuu     6180
cagagaacua gugaggaauu gugaccugcc cguuuggcuu ucguggcaag uggccaaggc     6240
ugguuugaag acgaaugauc guaaguggug uuuugaaggc ccugaggaac augagaucuu     6300
gaaugacagc ggugaaacag ugaagugcag ggcuccugga ggagcaaaga agccucugcg     6360
cccaaggugg uguggaugaaa gggugucauc ugaccagagu gcgcugucug aauuuauuaa     6420
guuugcugaa gguaggaggg gagcugcuga agugcuaguu gugcugagug aacucccuga     6480
uuuccuggcu aaaaagggug gagaggcaau ggauaccauc agugguuuc uccacucuga     6540 ggaaggcucu agggcuuacc gcaaugcacu aucaaugaug ccugaggcaa ugacaauagu     6600
caugcuguuu auacuggcug gacuacugac aucgggaaug ucacucuuuu ucaugucucc     6660
caaaggcauc aguagaaugu cuauggcgau gggcacaaug gccggcugug gauaucucau     6720
guuccuugga ggcgucaaac ccacucacau ucccuauauc augcucauau ucuuugccu      6780 gauggugguu gugauccccg agccagggca acaaaggucc auccaagaca accaaguggc     6840
auaccauauu auuggcaucc ugacgcuggu uucagcggug gcagccaacg agcuaggcau     6900
gcuggagaaa accaaagagg accucuuugg gaagaagaac uuaauuccau cuagugcuuc     6960
acccuggagu uggccggauc uugaccugaa gccaggagcu gccuggacag uuacguugg     7020 cauuguuaca augcucucuc caauuugca ccacuggauc aaagucgaau auggcaaccu      7080
gucucugucu ggaauagccc agucagccuc aguccuuucu uucauggaca aggggauacc     7140
auucaugaag augaauaucu cggucauaau gcugcgguc aguggcugga auucaauaac      7200
agugaugccu cugcucugug gcauagggug cgccaugcuc cacuggucuc ucauuuuacc     7260
uggaaucaaa gcgcagcagu caaagcuugc acagagaagg uguuccaug gcguugccaa      7320 gaacccugug guugauggga auccaacagu ugacauugag gaagcuccug aaaugccugc     7380
ccuuuaugag aagaaacugg cucuauaucu ccuucuugcu cucagccuag cuucuguugc     7440
caugugcaga acgcccuuuu cauuggcuga aggcauuguc cuagcaucag cugcccuagg     7500
gccgcucaua gagggaaaca ccagccuucu uggaauggga cccauggcug ucuccaugac     7560
aggagucaug agggggaauc acuaugcuuu gugggaguc auguacaauc uauggaagau      7620
gaaaacugga cgccggggga gcgcgaaugg aaaaacuuug ggugaagucu ggaagaggga     7680
acugaaucug uuggacaagc gacaguuuga guuguauaaa aggaccgaca uugguaggau     7740
ggaucgugau acggcacgca ggcauuuggc cgaagggaag guggacaccg ggguggcggu     7800 cuccagggg accgcaaagu uaaggugguu ccaugagcgu ggcuauguca agcuggaagg     7860 uaggugauu gaccuggggu guggccgcgg aggcuggugu uacuacgcug cugcgcaaaa       7920
ggaagugagu ggggucaaag gauuuacucu uggaagagac ggccaugaga aacccaugaa     7980
ugugcaaagu cugggauggaa acaucaucac cuucaaggac aaaacugaua uccaccgccu    8040
agaaccagug aaaugugaca cccuuuugug ugacauugga gagucaucau cgucaucggu    8100
cacagagggg gaaaggaccg ugagaguucu ugauacugua gaaaaauggc uggcuugugg     8160
gguugacaac uucugugaga gguguuagc uccauacaug ccagauguuc ucgagaaacu     8220
ggaauugcuc caaaggaggu uggcggaac agaucagg aaccucucu ccaggaauuc         8280 cacucaugaa auguacuacg ugucuggagc ccgcagcaau gucacauuua cuguaaccca     8340
aacaucccgc cuccugauga ggagaaugag gcguccaacu ggaaaaguga cccugggagc     8400
ugacgucauc cucccaauug ggacacgcag uguugagaca gacaagggac cccuggacaa     8460
```

```
agaggccaua gaagaaaggg uugagaggau aaaaucugag uacaugaccu cuugguuuua    8520
ugacaaugac aaccccuaca ggaccuggca cuacuguggc uccuauguca caaaaaccuc    8580
aggaagugcg gcgagcaugg uaaauggugu uauuaaaauu cugacauauc caugggacag    8640
gauagaggag gucacaagaa uggcaaugac ugacacaacc ccuuuggac agcaaagagu     8700 guuuaaagaa aaaguugaca ccagagcaaa ggauccacca gcgggaacua ggaagaucau    8760 gaaaguguc aacaggnggc uguuccgcca ccuggccaga gaaagaacc ccagacugug      8820 cacaaaggaa gaauuuauug caaaagnccg aagucaugca gccauggag cuuaccugga    8880 agaacaagaa cagnggaaga cugccaauga ggcugnccaa gacccaaagu ucugggaacu    8940
ggnggaugaa gaaaggaagc ugcaccaaca aggcaggngn cggacuugug uguacaacau    9000 gangggaaa agagagaaga agcugncaga guugggaaa gcaaagggaa gccgugccau     9060
augguauaug uggcugggag cgcggnaucu ugaguugag gcccugggau uccugaauga    9120
ggaccaungg gcuuccaggg aaaacucagg aggaggagug gaaggcauug gcuuacaaua    9180
ccuaggauau gugaucagag accuggcugc aauggaugnu ggnggauucu acgcggauga    9240
caccgcngga uggnacacgc gcaucacaga ggcagaccuu gaugaugaac aggagaucuu    9300
gaacuacaug agcccacauc acaaaaaacu ggcacaagca gugauggaaa ugacauacaa    9360
gaacaaagng gugaaagngu ugagaccagc cccaggaggg aaagccuaca uggaugncau    9420
aagucgacga gaccagagag gauccgggca ggnagugacu uaugcucuga acaccaucac    9480
caacungaaa guccaauuga ucagaauggc agaagcagag auggngauac aucaccaaca    9540
uguucaagau ugngaugaau caguucugac caggcuggag gcaugngcuca cugagcacgg    9600 auguaacaga cugaagagga uggcggngag uggagacgac ugugnggucc ggcccaucga   9660
ugacaggnuc ggccuggccc ugucccaucu caacgccaug uccaagguna gaaaggacau    9720
aucugaaugg cagccaucaa aagggnggaa ugauugggag aaugcccu ucuguuccca     9780 ccacuuccau gaacuacagc ugaaggaugg caggaggauu gngugngccuu gccgagaaca    9840 ggacgagcuc auugggagag gaagggnguc uccaggaaac ggcuggauga ucaaggaaac    9900
agcuugccuc agcaaagccu augccaacau gnggucacug augnauuuuc acaaagggga    9960
caugaggcua cugncauugg cuguuuccuc agcuguuccc accucauggg uuccacaagg   10020
acgcacaaca ugncgauuc augggaaagg ggagungaug accacggaag acaugcnuga   10080 ggngngggaac agaguaugga uaaccaacaa cccacacaug caggacaaga caaugngngaa    10140 aaaauggaga gangucccuu aucuaaccaa gagacaagac aagcugngcg gaucacugau    10200
uggaaugacc aauagggcca ccgggccuc ccacaucccau uuggucaucc aucguauccg    10260
aacgcugauu ggacaggaga aauacacuga cuaccuaaca gncauggaca ggnauucugu    10320
ggaugcugac cugcaacugg gngagcuuau cugaaacacc aucuaacagg aauaaccggg    10380
auacaaacca cggngnggaga accggacucc ccacaaccug aaaccgggau auaaaccacg    10440
gcuggagaac cggacuccgc acuuaaaaug aaacagaaac cgggauaaaa acuacggnaug    10500 gagaaccgga cuccacacau ugagacagaa gaagungnca gcccagaacc ccacacgagu    10560
uuugccacgc cuaagcugng aggcagngca ggcugggaca gccgaccucc agguugcgaa    10620
aaaccuggnu ucugggnaccu cccacccag agnaaaaaga acggagccuc cgcuaccacc    10680
cucccacgng gnggnaagnaa gacgggngucu agagguuaga ggagcccuc cagggaacaa    10740 auaugggac cauaungacg ccagggaaag accggagugg uucucugcuu uuccuccaga    10800
```

```
ggucugugag cacaguuugc ucaagaauaa gcagaccuuu ggaugacaaa cacaaaacca    10860
cu                                                                   10862
```

<210> SEQ ID NO 9
<211> LENGTH: 23
<212> TYPE: DNA
<213> ORGANISM: Artificial Sequence
<220> FEATURE:
<223> OTHER INFORMATION: DNA primer

<400> SEQUENCE: 9

```
gctaggcaat aaacacattt gga                                            23
```

<210> SEQ ID NO 10
<211> LENGTH: 21
<212> TYPE: DNA
<213> ORGANISM: Artificial Sequence
<220> FEATURE:
<223> OTHER INFORMATION: DNA primer

<400> SEQUENCE: 10

```
ttcactggga tactccttcg c                                              21
```

<210> SEQ ID NO 11
<211> LENGTH: 22
<212> TYPE: DNA
<213> ORGANISM: Artificial Sequence
<220> FEATURE:
<223> OTHER INFORMATION: DNA primer

<400> SEQUENCE: 11

```
atcaaatacc atcttgcccc tc                                             22
```

<210> SEQ ID NO 12
<211> LENGTH: 21
<212> TYPE: DNA
<213> ORGANISM: Artificial Sequence
<220> FEATURE:
<223> OTHER INFORMATION: DNA primer

<400> SEQUENCE: 12

```
agtaaatcct ttgacccccac t                                             21
```

<210> SEQ ID NO 13
<211> LENGTH: 18
<212> TYPE: DNA
<213> ORGANISM: Artificial Sequence
<220> FEATURE:
<223> OTHER INFORMATION: DNA primer

<400> SEQUENCE: 13

```
ggcttaccgc aatgcact                                                  18
```

<210> SEQ ID NO 14
<211> LENGTH: 18
<212> TYPE: DNA
<213> ORGANISM: Artificial Sequence
<220> FEATURE:
<223> OTHER INFORMATION: DNA primer

<400> SEQUENCE: 14

```
cagagaacca ctccggtc                                                  18
```

<210> SEQ ID NO 15
<211> LENGTH: 493

```
<212> TYPE: PRT
<213> ORGANISM: Yellow fever virus
<220> FEATURE:
<221> NAME/KEY: MISC_FEATURE
<223> OTHER INFORMATION: Sequence of the envelope protein of the YFV
      TV3111 or TV3112 strains

<400> SEQUENCE: 15
```

| | | | | | | | | | | | | | | |
|---|---|---|---|---|---|---|---|---|---|---|---|---|---|---|
| Ala | His | Cys | Ile | Gly | Ile | Thr | Asp | Arg | Asp | Phe | Ile | Glu | Gly | Val | His |
| 1 | | | | 5 | | | | | 10 | | | | | 15 |
| Gly | Gly | Thr | Trp | Val | Ser | Ala | Thr | Leu | Glu | Gln | Asp | Lys | Cys | Val | Thr |
| | | | 20 | | | | | 25 | | | | | 30 | |
| Val | Met | Ala | Pro | Asp | Lys | Pro | Ser | Leu | Asp | Ile | Ser | Leu | Glu | Thr | Val |
| | | 35 | | | | | 40 | | | | | 45 | | |
| Ala | Ile | Asp | Arg | Pro | Ala | Glu | Val | Arg | Lys | Val | Cys | Tyr | Asn | Ala | Val |
| | 50 | | | | | 55 | | | | | 60 | | | | |
| Leu | Thr | His | Val | Lys | Ile | Asn | Asp | Lys | Cys | Pro | Ser | Thr | Gly | Glu | Ala |
| 65 | | | | | 70 | | | | | 75 | | | | | 80 |
| His | Leu | Ala | Glu | Glu | Asn | Glu | Gly | Asp | Asn | Ala | Cys | Lys | Arg | Thr | Tyr |
| | | | | 85 | | | | | 90 | | | | | 95 | |
| Ser | Asp | Arg | Gly | Trp | Gly | Asn | Gly | Cys | Gly | Leu | Phe | Gly | Lys | Gly | Ser |
| | | | 100 | | | | | 105 | | | | | 110 | | |
| Ile | Val | Ala | Cys | Ala | Lys | Phe | Thr | Cys | Ala | Lys | Ser | Met | Ser | Leu | Phe |
| | | 115 | | | | | 120 | | | | | 125 | | | |
| Glu | Val | Asp | Gln | Thr | Lys | Ile | Gln | Tyr | Val | Ile | Arg | Ala | Gln | Leu | His |
| | 130 | | | | | 135 | | | | | 140 | | | | |
| Val | Gly | Ala | Lys | Gln | Glu | Asn | Trp | Thr | Thr | Asp | Ile | Lys | Thr | Leu | Lys |
| 145 | | | | | 150 | | | | | 155 | | | | | 160 |
| Phe | Asp | Ala | Leu | Ser | Gly | Ser | Gln | Glu | Val | Glu | Phe | Ile | Gly | Tyr | Gly |
| | | | | 165 | | | | | 170 | | | | | 175 | |
| Lys | Ala | Thr | Leu | Glu | Cys | Gln | Val | Gln | Thr | Ala | Val | Asp | Phe | Gly | Asn |
| | | | 180 | | | | | 185 | | | | | 190 | | |
| Ser | Tyr | Ile | Ala | Glu | Met | Glu | Thr | Glu | Ser | Trp | Ile | Val | Asp | Arg | Gln |
| | | 195 | | | | | 200 | | | | | 205 | | | |
| Trp | Ala | Gln | Asp | Leu | Thr | Leu | Pro | Trp | Gln | Ser | Gly | Ser | Gly | Gly | Val |
| | 210 | | | | | 215 | | | | | 220 | | | | |
| Trp | Arg | Glu | Met | His | His | Leu | Val | Glu | Phe | Glu | Pro | Pro | His | Ala | Ala |
| 225 | | | | | 230 | | | | | 235 | | | | | 240 |
| Thr | Ile | Arg | Val | Leu | Ala | Leu | Gly | Asn | Gln | Glu | Gly | Ser | Leu | Lys | Thr |
| | | | | 245 | | | | | 250 | | | | | 255 | |
| Ala | Leu | Thr | Gly | Ala | Met | Arg | Val | Thr | Lys | Asp | Thr | Asn | Asp | Asn | Asn |
| | | | 260 | | | | | 265 | | | | | 270 | | |
| Leu | Tyr | Lys | Leu | His | Gly | Gly | His | Val | Ser | Cys | Arg | Val | Lys | Leu | Ser |
| | | 275 | | | | | 280 | | | | | 285 | | | |
| Ala | Leu | Thr | Leu | Lys | Gly | Thr | Ser | Tyr | Lys | Ile | Cys | Thr | Asp | Lys | Met |
| | 290 | | | | | 295 | | | | | 300 | | | | |
| Phe | Phe | Val | Lys | Asn | Pro | Thr | Asp | Thr | Gly | His | Gly | Thr | Val | Val | Met |
| 305 | | | | | 310 | | | | | 315 | | | | | 320 |
| Gln | Val | Lys | Val | Ser | Lys | Gly | Ala | Pro | Cys | Arg | Ile | Pro | Val | Ile | Val |
| | | | | 325 | | | | | 330 | | | | | 335 | |
| Ala | Asp | Asp | Leu | Thr | Ala | Ala | Ile | Asn | Lys | Gly | Ile | Leu | Val | Thr | Val |
| | | | 340 | | | | | 345 | | | | | 350 | | |
| Asn | Pro | Ile | Ala | Ser | Thr | Asn | Asp | Asp | Glu | Val | Leu | Ile | Glu | Val | Asn |
| | | 355 | | | | | 360 | | | | | 365 | | | |
| Pro | Pro | Phe | Gly | Asp | Ser | Tyr | Ile | Ile | Val | Gly | Arg | Gly | Asp | Ser | Arg |

```
                    370                 375                 380
Leu Thr Tyr Gln Trp His Lys Glu Gly Ser Ser Ile Gly Lys Leu Phe
385                 390                 395                 400

Thr Gln Thr Met Lys Gly Val Glu Arg Leu Ala Val Met Gly Asp Thr
                405                 410                 415

Ala Trp Asp Phe Ser Ser Ala Gly Gly Phe Phe Thr Ser Val Gly Lys
                420                 425                 430

Gly Ile His Thr Val Phe Gly Ser Ala Phe Gln Gly Leu Phe Gly Gly
                435                 440                 445

Leu Asn Trp Ile Thr Lys Val Ile Met Gly Ala Val Leu Ile Trp Val
450                 455                 460

Gly Ile Asn Thr Arg Asn Met Thr Met Ser Met Ser Met Ile Leu Leu
465                 470                 475                 480

Gly Val Ile Met Met Phe Leu Ser Leu Gly Val Gly Ala
                485                 490

<210> SEQ ID NO 16
<211> LENGTH: 224
<212> TYPE: PRT
<213> ORGANISM: Yellow fever virus
<220> FEATURE:
<221> NAME/KEY: MISC_FEATURE
<223> OTHER INFORMATION: Sequence of the NS2a protein of the YFV TV3111
      or TV3112 strains

<400> SEQUENCE: 16

Gly Glu Ile His Ala Val Pro Phe Gly Leu Val Ser Met Met Ile Ala
1               5                   10                  15

Met Glu Val Val Leu Arg Lys Arg Gln Gly Pro Lys Gln Met Leu Val
                20                  25                  30

Gly Gly Val Val Leu Leu Gly Ala Met Leu Val Gly Gln Val Thr Leu
                35                  40                  45

Leu Asp Leu Leu Lys Leu Thr Val Ala Val Gly Leu His Phe His Glu
50                  55                  60

Val Asn Asn Gly Gly Asp Ala Met Tyr Met Ala Leu Ile Ala Ala Phe
65                  70                  75                  80

Ser Ile Arg Pro Gly Leu Leu Ile Gly Phe Gly Leu Arg Thr Leu Trp
                85                  90                  95

Ser Pro Arg Glu Arg Leu Val Leu Thr Leu Gly Ala Ala Met Val Glu
                100                 105                 110

Ile Ala Leu Gly Gly Val Met Gly Gly Leu Trp Lys Tyr Leu Asn Ala
                115                 120                 125

Val Ser Leu Cys Ile Leu Thr Ile Asn Ala Val Ala Ser Arg Lys Ala
130                 135                 140

Ser Asn Thr Ile Leu Pro Leu Met Ala Leu Leu Thr Pro Val Thr Met
145                 150                 155                 160

Ala Glu Val Arg Leu Ala Ala Met Phe Phe Cys Ala Val Val Ile Ile
                165                 170                 175

Gly Val Leu His Gln Asn Phe Lys Asp Thr Ser Met Gln Lys Thr Ile
                180                 185                 190

Pro Leu Val Ala Leu Thr Leu Thr Ser Tyr Leu Gly Leu Thr Gln Pro
                195                 200                 205

Phe Leu Gly Leu Cys Ala Phe Leu Ala Thr Arg Ile Phe Gly Arg Arg
                210                 215                 220

<210> SEQ ID NO 17
```

```
<211> LENGTH: 378
<212> TYPE: RNA
<213> ORGANISM: Yellow fever virus
<220> FEATURE:
<221> NAME/KEY: misc_feature
<223> OTHER INFORMATION: RNA Sequence coding for the NS4a protein of the
      YFV TV3112 strain

<400> SEQUENCE: 17
ggagcugcug aagugcuagu ugugcugagu gaacucccug auuccuggc uaaaaagggu      60 ggagaggcaa uggauaccau cagugguguu cuccacucug aggaaggcuc uagggcuuac     120
cgcaaugcac uaucaaugau gccugaggca augacaauag ucaugcuguu uauacuggcu    180
ggacuacuga caucgggaau ggucaucuuu ucaugcucuc ccaaaggcau caguagaaug    240
ucuauggcga ugggcacaau ggccggcugu ggauaucuca uguccuugg aggcgucaaa    300 cccacucaca ucuccuauau caugcucaua uucuuugucc ugauggugu ugugauccccc   360 gagccagggc aacaaagg                                                   378

<210> SEQ ID NO 18
<211> LENGTH: 1479
<212> TYPE: RNA
<213> ORGANISM: Yellow fever virus
<220> FEATURE:
<221> NAME/KEY: misc_feature
<223> OTHER INFORMATION: RNA Sequence coding for the envelope protein of
      the YFV TV3112 strain

<400> SEQUENCE: 18
gcucacugca uuggaauuac ugacagggau uucauugagg gggugcaugg aggaacuugg     60
guuucagcua cccuggagca agacaagugu gucacuguua uggcccccuga caagccuuca   120 uuggacaucu cacuagagac aguagccauu gauagaccug cugaggugag gaaagugugu   180 acaaugcag uucucacuca ugugaagauu aaugacaagu gccccagcac uggagaggcc    240
caccuagcug aagagaacga aggggacaau gcgugcaagc gcacuuauuc ugauagaggc    300
uggggcaaug gcuguggccu auugggaaa gggagcauug uggcaugcgc caaauucacu   360
ugugccaaau ccaugagcuu uguugagguu gaucagacca aaauucagua ugucaucaga    420
gcacaauugc auguuggggc caagcaggaa aauuggacua ccgacauuaa gacucucaag    480
uuugaugccc cugucaggcuc ccaggaaguc gaguucauug gguaggaaa agcuacacug    540 gaaugccagg ugcaaacugc gguggacuuu gguaacaguu acaucgcuga augaaaaca    600 gagagcugga uagugacag acagugggcc caggacuuga cccugccaug gcagagugga    660
aguggcgggg ugugagaga gaugcaucau cuugucgaau ugaaccuucc gcaugccgcc    720
acuaucagag uacuggcccu gggaaaccag gaaggcuccu ugaaaacagc ucuuacuggc   780
gcaaugaggg uuacaaagga cacaaaugac aacaaccuuu acaaacuaca ugguggacau   840
guuucuugca gagugaaauu gucagcuuug cacucaagg ggacauccua caaauaugc     900 acugacaaaa uguuuuuugu caagaacccaa cugacacug gccauggcac uguugugaug    960
caggugaaag uguucaaagg agcccccugc aggauccag ugauaguagc ugaugaucuu   1020
acagcggcaa ucaauaaagg cauuuugguu acaguuaacc ccaucgccuc aaccaaugau   1080
gaugaagugc ugauugaggu gaacccaccu uuuggagaca gcuacauuau cguugggaga   1140
ggagauucac gucucacuua ccaguggcac aaagagggaa gcucaauagg aaaguuguuc   1200
acucagacca ugaaggcgu ggaacgcccug gccgucaugg agacaccgcg cuggauuuuc   1260
agcuccgcug gaggguucuu cacuucggu gggaaaggaa uucauacggu guuggcucu   1320
```

```
gccuuucagg ggcuauuugg cggcuugaac uggauaacaa aggucaucau gggggcggua    1380
cuuauauggg uuggcaucaa cacaagaaac augacaaugu ccaugagcau gaucuuguua    1440
ggagugauca ugauguuuuu gucucuagga guuggggcg                          1479
```